(12) United States Patent
Charles et al.

(10) Patent No.: US 10,702,608 B2
(45) Date of Patent: Jul. 7, 2020

(54) FACTOR VIII ZWITTERIONIC POLYMER CONJUGATES

(71) Applicant: Kodiak Sciences Inc., Palo Alto, CA (US)

(72) Inventors: Stephen A. Charles, Ravenna, OH (US); D. Victor Perlroth, Palo Alto, CA (US); Li Song, Cupertino, CA (US); Martin Linsell, San Mateo, CA (US); Wayne To, San Mateo, CA (US); Didier Benoit, San Jose, CA (US); James Aggen, Westwood, MA (US)

(73) Assignee: KODIAK SCIENCES INC., Palo Alto, CA (US)

( * ) Notice: Subject to any disclaimer, the term of this patent is extended or adjusted under 35 U.S.C. 154(b) by 104 days.

(21) Appl. No.: 14/916,180

(22) PCT Filed: Sep. 8, 2014

(86) PCT No.: PCT/US2014/054622
§ 371 (c)(1),
(2) Date: Mar. 2, 2016

(87) PCT Pub. No.: WO2015/035342
PCT Pub. Date: Mar. 12, 2015

(65) Prior Publication Data
US 2016/0199501 A1    Jul. 14, 2016

Related U.S. Application Data

(60) Provisional application No. 61/875,099, filed on Sep. 8, 2013.

(51) Int. Cl.
A61K 9/00        (2006.01)
A61K 47/48       (2006.01)
(Continued)

(52) U.S. Cl.
CPC ........ A61K 47/48176 (2013.01); A61K 38/37 (2013.01); A61K 47/59 (2017.08);
(Continued)

(58) Field of Classification Search
CPC .................................................. A61K 47/48176
See application file for complete search history.

(56) References Cited

U.S. PATENT DOCUMENTS 4,634,664 A    1/1987  Oestberg
4,634,666 A    1/1987  Engleman et al.
(Continued)

FOREIGN PATENT DOCUMENTS

AU    2015207898    8/2015
AU    2017201930    4/2017
(Continued)

OTHER PUBLICATIONS

Written Opinion and International Search Report in PCT Application No. PCT/US2014/054622, dated Feb. 27, 2015 in 7 pages.
(Continued)

Primary Examiner — Paul W Dickinson
(74) Attorney, Agent, or Firm — Knobbe, Martens, Olson & Bear, LLP

(57) ABSTRACT

The present invention provides multi-armed high MW polymers containing hydrophilic groups conjugated to Factor VIII, and methods of preparing such polymers.

20 Claims, 2 Drawing Sheets

Specification includes a Sequence Listing.

(51) Int. Cl.
   *C08G 65/333*     (2006.01)
   *C08F 120/36*    (2006.01)
   *A61K 38/37*     (2006.01)
   *C07K 14/755*    (2006.01)
   *A61K 47/59*     (2017.01)
   *A61K 47/60*     (2017.01)

(52) U.S. Cl.
   CPC ............ *A61K 47/60* (2017.08); *C07K 14/755* (2013.01); *C08F 120/36* (2013.01); *C08G 65/33324* (2013.01)

(56) References Cited

U.S. PATENT DOCUMENTS

| | | |
|---|---|---|
| 4,892,538 A | 1/1990 | Aebischer et al. |
| 5,225,539 A | 7/1993 | Winter |
| 5,283,187 A | 2/1994 | Aebischer et al. |
| 5,336,603 A | 8/1994 | Capon et al. |
| 5,530,101 A | 6/1996 | Queen et al. |
| 5,545,806 A | 8/1996 | Lonberg et al. |
| 5,565,332 A | 10/1996 | Hoogenboom et al. |
| 5,569,825 A | 10/1996 | Lonberg et al. |
| 5,585,089 A | 12/1996 | Queen et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,663,425 A | 9/1997 | Detroit et al. |
| 5,681,746 A | 10/1997 | Bodner et al. |
| 5,733,743 A | 3/1998 | Johnson et al. |
| 5,741,923 A | 4/1998 | Driver et al. |
| 5,763,548 A | 6/1998 | Matyjaszewski et al. |
| 5,770,429 A | 6/1998 | Lonberg et al. |
| 5,789,487 A | 8/1998 | Matyjaszewski et al. |
| 5,789,650 A | 8/1998 | Lonberg et al. |
| 5,807,937 A | 9/1998 | Matyjaszewski et al. |
| 5,814,318 A | 9/1998 | Lonberg et al. |
| 5,834,597 A | 11/1998 | Tso et al. |
| 5,837,242 A | 11/1998 | Holliger et al. |
| 5,858,657 A | 1/1999 | Winter et al. |
| 5,859,205 A | 1/1999 | Adair et al. |
| 5,871,907 A | 2/1999 | Winter et al. |
| 5,872,218 A | 2/1999 | Wolf et al. |
| 5,874,299 A | 2/1999 | Lonberg et al. |
| 5,877,218 A | 3/1999 | Herzig et al. |
| 5,877,397 A | 3/1999 | Lonberg et al. |
| 5,882,644 A | 3/1999 | Chang et al. |
| 5,945,491 A | 8/1999 | Matyjaszewski et al. |
| 5,981,786 A | 11/1999 | Kitano et al. |
| 6,111,022 A | 8/2000 | Matyjaszewski et al. |
| 6,121,371 A | 9/2000 | Matyjaszewski et al. |
| 6,124,411 A | 9/2000 | Matyjaszewski et al. |
| 6,162,882 A | 12/2000 | Matyjaszewski et al. |
| 6,407,187 B1 | 6/2002 | Matyjaszewski et al. |
| 6,407,213 B1 | 6/2002 | Carter et al. |
| 6,512,060 B1 | 1/2003 | Matyjaszewski et al. |
| 6,538,091 B1 | 3/2003 | Matyjaszewski et al. |
| 6,541,580 B1 | 4/2003 | Matyjaszewski et al. |
| 6,555,593 B1 | 4/2003 | Hoyle et al. |
| 6,583,272 B1 | 6/2003 | Bailon |
| 6,624,262 B2 | 9/2003 | Matyjaszewski et al. |
| 6,627,314 B2 | 9/2003 | Matyjaszewski et al. |
| 6,759,491 B2 | 7/2004 | Matyjaszewski et al. |
| 6,790,919 B2 | 9/2004 | Matyjaszewski et al. |
| 6,852,816 B2 | 2/2005 | Lewis et al. |
| 6,881,557 B2 | 4/2005 | Foote |
| 6,887,962 B2 | 5/2005 | Matyjaszewski et al. |
| 6,979,556 B2 | 12/2005 | Simmons et al. |
| 7,019,082 B2 | 3/2006 | Matyjaszewski et al. |
| 7,049,373 B2 | 5/2006 | Matyjaszewski et al. |
| 7,056,455 B2 | 6/2006 | Matyjaszewski et al. |
| 7,060,271 B2 | 6/2006 | Ramakrishnan et al. |
| 7,064,166 B2 | 6/2006 | Matyjaszewski et al. |
| 7,125,938 B2 | 10/2006 | Matyjaszewski et al. |
| 7,157,530 B2 | 1/2007 | Matyjaszewski et al. |
| 7,169,901 B2 | 1/2007 | Baca et al. |
| 7,300,990 B2 | 11/2007 | Lewis et al. |
| 7,306,799 B2 | 12/2007 | Wiegand et al. |
| 7,348,424 B2 | 3/2008 | Miyazawa et al. |
| 7,374,757 B2 | 5/2008 | Papadopoulos et al. |
| 7,375,193 B2 | 5/2008 | Baca et al. |
| 7,521,541 B2 | 4/2009 | Eigenbrot et al. |
| 7,569,655 B2 | 8/2009 | Pacetti et al. |
| 7,740,850 B2 | 6/2010 | Zhu et al. |
| 7,754,208 B2 | 7/2010 | Ledbetter et al. |
| 7,754,855 B1 | 7/2010 | Cox, III et al. |
| 7,759,472 B2 | 7/2010 | Shima et al. |
| 7,855,178 B2 | 12/2010 | Alitalo et al. |
| 7,893,173 B2 | 2/2011 | Matyjaszewski et al. |
| 8,003,097 B2 | 8/2011 | Schroeter et al. |
| 8,008,453 B2 | 8/2011 | Gegg et al. |
| 8,187,597 B2 | 5/2012 | Shima et al. |
| 8,206,707 B2 | 6/2012 | Shima et al. |
| 8,273,353 B2 | 9/2012 | Davis-Smyth et al. |
| 8,455,622 B2 | 6/2013 | McDonagh et al. |
| 8,486,397 B2 | 7/2013 | Bagri et al. |
| 8,492,527 B2 | 7/2013 | Fuh et al. |
| 8,512,699 B2 | 8/2013 | Fuh et al. |
| 8,765,432 B2 | 7/2014 | Charles |
| 8,815,236 B2 | 8/2014 | Burke et al. |
| 8,846,021 B2 | 9/2014 | Charles |
| 9,079,953 B2 | 7/2015 | Harding et al. |
| 9,416,210 B2 | 8/2016 | Emrick et al. |
| 9,840,553 B2 | 12/2017 | Perlroth et al. |
| 2003/0143596 A1 | 7/2003 | Bentley et al. |
| 2004/0063881 A1 | 4/2004 | Lewis et al. |
| 2004/0253596 A1 | 12/2004 | Pawlak et al. |
| 2005/0112088 A1 | 5/2005 | Zhao et al. |
| 2005/0118651 A1 | 6/2005 | Basi et al. |
| 2005/0123501 A1 | 6/2005 | Lews |
| 2005/0136049 A1 | 6/2005 | Ledbetter et al. |
| 2005/0159556 A1 | 7/2005 | Lewis et al. |
| 2005/0180945 A1 | 8/2005 | Chaikof et al. |
| 2005/0220880 A1 | 10/2005 | Lewis et al. |
| 2005/0276796 A1 | 12/2005 | Tomatsu et al. |
| 2006/0135714 A1 | 6/2006 | Lewis et al. |
| 2006/0165804 A1 | 7/2006 | Lewis et al. |
| 2006/0167230 A1 | 7/2006 | Koga et al. |
| 2006/0217285 A1 | 9/2006 | Destarac |
| 2006/0234437 A1 | 10/2006 | Harding et al. |
| 2007/0041967 A1 | 2/2007 | Jung et al. |
| 2007/0111279 A1 | 5/2007 | Rosenberg |
| 2007/0141104 A1 | 6/2007 | Hauenstein |
| 2008/0008736 A1 | 1/2008 | Glauser |
| 2008/0124450 A1 | 5/2008 | Pacetti |
| 2008/0147178 A1 | 6/2008 | Pacetti et al. |
| 2008/0199464 A1 | 8/2008 | Plowman et al. |
| 2009/0060906 A1 | 3/2009 | Barry et al. |
| 2009/0061533 A1 | 3/2009 | Minami |
| 2009/0117103 A1 | 7/2009 | Devalaraja et al. |
| 2009/0324679 A1 | 12/2009 | Ippoliti et al. |
| 2010/0111942 A1 | 5/2010 | Shima et al. |
| 2010/0158850 A1 | 6/2010 | Baker, Jr. et al. |
| 2010/0166700 A1 | 7/2010 | Charles |
| 2010/0322931 A1 | 12/2010 | Harding et al. |
| 2011/0033378 A1 | 2/2011 | Dimasi et al. |
| 2011/0165648 A1 | 7/2011 | Campange et al. |
| 2012/0100136 A1 | 4/2012 | Patel et al. |
| 2012/0213705 A1 | 8/2012 | Dimasi et al. |
| 2012/0282211 A1 | 11/2012 | Washburn et al. |
| 2012/0322738 A1 | 12/2012 | Behrens et al. |
| 2013/0034517 A1 | 2/2013 | Charles et al. |
| 2013/0040889 A1 | 2/2013 | Bolt et al. |
| 2013/0045522 A1 | 2/2013 | Charles et al. |
| 2013/0071394 A1 | 3/2013 | Troyer et al. |
| 2013/0259881 A1 | 10/2013 | Fandl et al. |
| 2013/0337534 A1 | 12/2013 | Charles |
| 2014/0024776 A1 | 1/2014 | Charles et al. |
| 2014/0170140 A1 | 2/2014 | Bennett et al. |
| 2014/0242082 A1 | 8/2014 | Shima et al. |
| 2015/0004128 A1 | 1/2015 | Charles et al. |
| 2015/0050714 A1 | 2/2015 | Charles |
| 2015/0071861 A1 | 3/2015 | Kondo et al. |
| 2015/0093390 A1 | 4/2015 | Bansal |
| 2015/0158952 A1 | 6/2015 | Mao et al. |

(56) References Cited

U.S. PATENT DOCUMENTS

| | | |
|---|---|---|
| 2015/0376271 A1 | 12/2015 | Perlroth et al. |
| 2016/0008485 A1 | 1/2016 | Marquette et al. |
| 2016/0184445 A1 | 6/2016 | Perlroth et al. |
| 2016/0287715 A1 | 10/2016 | Charles et al. |
| 2016/0346400 A1 | 12/2016 | Emrick et al. |
| 2016/0369005 A1 | 12/2016 | Lippincott et al. |
| 2017/0007710 A1 | 1/2017 | Charles et al. |
| 2017/0143841 A1 | 5/2017 | Charles et al. |
| 2017/0190766 A1 | 7/2017 | Perlroth et al. |
| 2018/0244762 A1 | 8/2018 | Perlroth et al. |
| 2018/0334496 A1 | 11/2018 | Perlroth et al. |

FOREIGN PATENT DOCUMENTS

| | | | | |
|---|---|---|---|---|
| CN | 101389690 | 3/2009 | | |
| CN | 102811713 | 12/2012 | | |
| CN | 103193819 | 7/2013 | | |
| CN | 103421039 | 12/2013 | | |
| CN | 103492489 | 1/2014 | | |
| CN | 106075466 | 11/2016 | | |
| CN | 106432557 | 2/2017 | | |
| CN | 107428824 | 12/2017 | | |
| CN | 108712911 A | 10/2018 | | |
| CO | 12119310 | 12/2012 | | |
| CO | 12203725 | 2/2013 | | |
| EP | 1465933 | 8/2007 | | |
| EP | 1592719 | 3/2008 | | |
| EP | 1988910 | 11/2008 | | |
| EP | 1732621 | 12/2009 | | |
| EP | 2260873 | 12/2010 | | |
| EP | 2512462 | 10/2012 | | |
| EP | 2203180 | 11/2012 | | |
| EP | 3222142 | 9/2017 | | |
| EP | 3254678 | 12/2017 | | |
| JP | H10 139832 | 5/1998 | | |
| JP | H11 217588 | 8/1999 | | |
| JP | 2003-064132 | 3/2003 | | |
| JP | 2005-239989 | 9/2005 | | |
| JP | 2005-255969 | 9/2005 | | |
| JP | 2006-503549 | 2/2006 | | |
| JP | 2007-263935 | 10/2007 | | |
| JP | 2008-133434 | 6/2008 | | |
| JP | 2008-524247 | 7/2008 | | |
| JP | 2009-042617 | 2/2009 | | |
| JP | 2009-532330 | 9/2009 | | |
| JP | 2009-533519 | 9/2009 | | |
| JP | 2009-542862 | 12/2009 | | |
| JP | 2009-543895 | 12/2009 | | |
| JP | 2010-117189 | 5/2010 | | |
| JP | 2012-025820 | 2/2012 | | |
| JP | 2013-515099 | 5/2013 | | |
| JP | 2013-534931 | 9/2013 | | |
| JP | 2014-043456 | 3/2014 | | |
| JP | 5760007 | 6/2015 | | |
| JP | 5745009 | 7/2015 | | |
| JP | 2016-14015 | 1/2016 | | |
| JP | 5846044 | 1/2016 | | |
| JP | 2016-040371 | 3/2016 | | |
| JP | 2016-530302 | 9/2016 | | |
| JP | 2017-31410 | 2/2017 | | |
| JP | 2018-87330 | 6/2018 | | |
| KR | 10-0808116 | 3/2008 | | |
| KR | 20120123340 | 11/2012 | | |
| KR | 2013-0097636 | 9/2013 | | |
| KR | 10-1852044 | 4/2018 | | |
| MX | 2012006970 | 10/2012 | | |
| MX | 2012011876 | 11/2012 | | |
| MX | 346423 | 3/2017 | | |
| MX | 2016017290 | 8/2017 | | |
| WO | WO 91/10741 | 7/1991 | | |
| WO | WO 91/17271 | 11/1991 | | |
| WO | WO 92/01047 | 1/1992 | | |
| WO | WO 93/12227 | 6/1993 | | |
| WO | WO 93/25673 | 12/1993 | | |
| WO | WO 1994/016748 | 8/1994 | | |
| WO | WO 97/14702 | 4/1997 | | |
| WO | WO 97/14703 | 4/1997 | | |
| WO | WO 98/45331 | 10/1998 | | |
| WO | WO 2000/059968 | 10/2000 | | |
| WO | WO 0141827 | 6/2001 | | |
| WO | WO 2002/028929 | 4/2002 | | |
| WO | WO 2003/062290 | 7/2003 | | |
| WO | WO 2003/074026 | 9/2003 | | |
| WO | WO 2003/074090 | 9/2003 | | |
| WO | WO 2004/020405 | 3/2004 | | |
| WO | WO 2004/063237 | 7/2004 | | |
| WO | WO 2004/091494 | 10/2004 | | |
| WO | WO 2004/113394 | 12/2004 | | |
| WO | WO 2005/028539 | 3/2005 | | |
| WO | WO 2005/058367 | 6/2005 | | |
| WO | WO 2006/063055 | 6/2006 | | |
| WO | WO 2006/118547 | 11/2006 | | |
| WO | WO 2007/005253 | 1/2007 | | |
| WO | WO 2007/075534 | 7/2007 | | |
| WO | WO 2007/100902 | 9/2007 | | |
| WO | WO 2008/020827 | 2/2008 | | |
| WO | WO 2008/025856 | 3/2008 | | |
| WO | WO 2008/098930 | 8/2008 | | |
| WO | WO 2008/112257 | 9/2008 | | |
| WO | WO 2008/112289 | 9/2008 | | |
| WO | WO 2008/144248 | 11/2008 | | |
| WO | WO 2008/155134 | 12/2008 | | |
| WO | WO 2009/052249 | 4/2009 | | |
| WO | WO 2005/047334 | 5/2009 | | |
| WO | WO 2009/138473 | 11/2009 | | |
| WO | WO 2010/040508 | 4/2010 | | |
| WO | WO 2010/068862 | 6/2010 | | |
| WO | WO 2010/068864 | 6/2010 | | |
| WO | WO 2010/111625 | 9/2010 | | |
| WO | WO 01/18080 | 3/2011 | | |
| WO | WO 2011/075185 | 6/2011 | | |
| WO | WO 2011/075736 | 6/2011 | | |
| WO | WO 2011130694 A2 * | 10/2011 | ............ | C08F 230/02 |
| WO | WO-2013059137 A1 * | 4/2013 | ....... | A61K 47/48176 |
| WO | WO 2013/093809 | 6/2013 | | |
| WO | WO 2014/060401 | 4/2014 | | |
| WO | WO 2014/160507 | 10/2014 | | |
| WO | WO 2015/200905 | 12/2015 | | |
| WO | WO 2017/117464 | 7/2017 | | |
| WO | WO 2018/191548 | 10/2018 | | |

OTHER PUBLICATIONS

Lin, Weifeng et al., "A Novel Zwitterionic Copolymer With a Short Poly(Methyl Acrylic Acid) Block for Improving Both Conjugation and Separation Efficiency of a Protein Without Losing its Bioactivity," Journal of Materialos Chemistry B. May 21, 2013, vol. 1, No. 19, pp. 2482-2488.

Tao, Lei et al., "Branched Polymer-Protein Conjugates Made From Mid-Chain-Functional P (HPMA)", Biomacromolecules, 2009, vol. 10, No. 10, pp. 2487-2851.

Ambati et al., "Mechanisms of age-related macular degeneration," Neuron, vol. 75, No. 1, pp. 26-39, 2012.

Anderson, W.F., "Human gene therapy," Science, vol. 256, No. 5058, pp. 808-813, May 8, 1992.

Andrae et al., "Role of platelet-derived growth factors in physiology and medicine," Genes & Development, vol. 22, pp. 1276-1312, 2008.

Armulik, A. et al., "Endothelial/Pericyte Interactions," Circulation Research, vol. 97, Issue 6, pp. 512-523, Sep. 16, 2005.

Baluk, P. et al., "Cellular abnormalities of blood vessels as targets in cancer," Current Opinion in Genetics & Development, vol. 15, Issue 1, pp. 102-111, Feb. 2005.

Bates, D.O. et al., "Vascular endothelial growth factor increases microvascular permeability via a Ca(2+)-dependent pathway," American Journal of Physiology, vol. 273, No. 2, pp. H687-H694, Aug. 1, 1997.

Berthold, W. et al., "Protein Purification: Aspects of Processes for Pharmaceutical Products," Biologicals, vol. 22, Issue 2, pp. 135-150, Jun. 1994.

(56) References Cited

OTHER PUBLICATIONS

Blong, M. Renee et al., "Tetramerization domain of human butyrylcholinesterase is at the C-terminus," Biochemical Journal, vol. 327, No. 3, pp. 747-757, Nov. 1, 1997.
Bowen-Pope et al., "History of Discovery: Platelet-derived Growth Factor," Arterioscler Thromb Vasc Biol., vol. 31, No. 11, pp. 2397-2401, Nov. 2011.
Bontempo, et al., "Cysteine-Reactive Polymers Synthesized by Atom Transfer Radical Polymerization for Conjugation to Proteins," J. Am. Chem. Soc. (2004), 126, pp. 15372-15373.
Brown, D. et al., "Ranibizumab versus Verteporfin for Neovascular Age-Related Macular Degeneration," The New England Journal of Medicine, vol. 355, No. 14, pp. 1432-1444, Oct. 5, 2006.
Capon, D. et al., "Designing CD4 immunoadhesins for AIDS therapy," Nature, vol. 337, pp. 525-531, 1989.
Carmeliet, P., "Angiogenesis in healt and disease," Nature Medicine, vol. 9, pp. 653-660, (2003).
Carmeliet, P., "Synergism between vascular endothelial growth factor and placental growth factor contributes to angiogenesis and plasma extravasation in pathological conditions," Nature Medicine, vol. 7, No. 5, pp. 575-583, May 2001.
Carmeliet, "Mechanisms of angiogenesis and arteriogenesis," Nature Medicine, vol. 6, No. 3, pp. 389-395, 2000.
Casset, F. et al. A Peptide Mimetic of an Anti0CD4 Monoclonal Antibody by Rational Design, Biochemical and Biophysical Research Communications, vol. 307, pp. 198-205, (2003).
Chen et al., "Factors affecting endotoxin removal from recombinant therapeutic proteins by anion exchange chromatography," Protein Expression and Purification, vol. 64, pp. 76-81, 2009.
Chen, et al., "Lubrication at Physiological Pressures by Polyzwitterionic Brushes," Science, (2009), 323, pp. 1698-1701.
Chen, et al., "Polymeric Phosphorylcholine-Camptothecin Conjugates Prepared by Controlled Free Radical Polymerizationand Click Chemistry," Bioconjugate Chem., (2009), 20:12, pp. 2331-2341.
Chen, Y et al. Selection and Analysisi an Optimized Anti-VEGF Antibody: Crystal Structure of an Affinity-Matured Complex with Antigen, J. Mol. Biol,, vol. 293, pp. 865-881 , (1999).
Chothia, C. et al., "Canonical structures for the hypervariable regions of immunoglobulins," Journal of Molecular Biology, vol. 196, Issue 4, pp. 901-917, Aug. 20, 1989.
Chothia, C. et al., "Conformations of immunoglobulin hypervariable regions," Nature, vol. 342, pp. 877-883, Dec. 1989.
Christy, N.E. et al., "Antibiotic prophylaxis of postoperative endophthalmitis," Annals of Ophthalmology, vol. 11, No. 8, pp. 1261-1265, Aug. 1, 1979.
Cohen, S.Y. et al., "Causes of unsuccessful ranibizumab treatment in exudative age-related macular degeneration in clinical settings," Retina, vol. 32, Issue 8, pp. 1480-1485, Sep. 2012.
Crowe, et al., "Recombinant human respiratory syncytial virus (RSV) monoclonal antibody Fab is effective therapeutically when introduced directly into the lungs of RSV-infected mice," Proc. Natl. Acad. Sci. USA, (1994) 91 pp. 1386-1390.
Da Pieve, et al., "Conjugation of PolyPEG®, Linear PEG and Branched PEG to a Thiol-Modified Aptamer," Poster, Warwick Effect Polymers Ltd, retrieved from <http:www.wep-ltd.co.uk> (2010).
Da Pieve, et al., "Modification of Thiol Functionalized Aptamers by Conjugation of Synthetic Polymers," Bioconjugate Chem., (2010), 21:1, pp. 169-174.
Daneshian, M. et al., "In vitro pyrogen test for toxic or immunomodulatory drugs," Journal of Immunological Methods, vol. 313, Issues 1-2, pp. 169-175, Jun. 30, 2006.
De Pascalis, R. et al., "Grafting of "abbreviated" complementarity-determining regions containing specificity-determining residues essential for ligand contact to engineer a less immunogenic humanized monoclonal antibody," J. Immunol., vol. 169, No. 6, pp. 3076-3084, Sep. 15, 2002.
Declaration of Harvey N. Masonson, M.D., under 37 C.F.R., for U.S. Appl. No. 12/465,051, filed May 13, 2009, including Exhibits A, B, and C, signed Jul. 6, 2011, in 50 pages.
Dillon et al., "Structural and functional characterization of disulfide isoforms of the human IgG2 subclass," The Journal of Biological Chemistry, vol. 283, No. 23, pp. 16206-16215, 2008.
Ding, J.L. et al., "A new era of pyrogen testing," Trends in Biotechnology, vol. 19, Issue 8, pp. 277-281, Aug. 1, 2001.
Dong, et al., "ARGET ATRP of 2-(Dimethylamino)ethyl Methacrylate as an Intrinsic Reducing Agent," Macromolecules, (2008), 41:19 pp. 6868-6870.
Dong, et al., "Well-Defined High-Molecular-Weight Polyacrylonitrile via Activators Regenerated by Electron Transfer ATRP," Macromolecules, (2007), 40:9, pp. 2974-2977.
Du et al. "pH-Sensitive Vesicles based on a Biocompatible Zwitterionic Diblock Copolymer" J. Am. Chem. Soc., Dec. 1, 2005, 127, 17982-17983.
Edelman et al., "The covalent structure of an entire yG immunoglobulin molecule," Proceedings of the National Academy of Sciences, vol. 63, pp. 78-85, May 1, 1969.
Engelgau, M et al. Evolving Diabetes Burden in the United States. Ann of Int Med. 140(11): 945-951, 2004.
"Facts About Diabetic Eye Disease", National Eye Institute, https://nei.nih.gov/health/diabetic/retinopathy, publication reviewed Sep. 2015, accessed Mar. 27, 2018, in 7 pages.
Fares, F.A. et al., "Design of a long-acting follitropin agonist by fusing the C-terminal sequence of the chorionic gonadotropin beta subunit to the follitropin beta subunit," Proc Natl Acad Sci USA, vol. 89, No. 10, pp. 4304-4308, May 15, 1992.
Ferrara, N. et al., "The Biology of Vascular Endothelial Growth Factor," Endocrine Reviews, vol. 18, No. 1, pp. 4-25, (1997).
Ferrara, et al. Development of Ranibizumab, An Anti-Vascular Endothelial Growth, as Therapy for Neovascular Age-Related Macular Degeneration, Retina, The Journal of Retinal and Vitreous Diseas, vol. 26, Issue No. 8, pp. 859-870, (2006).
Ferrara, et al , "The Biology of VEGF and its Receptors", Nature Medicine, vol. 9 No. 6, pp. 669-676, (2003).
Fiske, M. et al., "Method for reducing endotoxin in Moraxella catarrhalis UspA2 protein preparations," Journal of Chromatography B: Biomedical Sciences and Applications, vol. 753, Issue 2, pp. 269-278, Apr. 5, 2001.
Folkman, J., "Angiogenesis: an organizing principle for drug discover?" Nature Reviews, Drug Discovery, vol. 6, pp. 273-286, Apr. 2007.
Fontaine et al., "Long-Term Stabilization of Maleimide-Thiol Conjugates," Bioconjugate Chem., vol. 26, pp. 145-152, 2015.
Foster, Graham R., "Pegylated interferons for the treatment of chronic Hepatitis C," Drugs, vol. 70, Issue 2, pp. 147-165, Jan. 2010.
Friedman, D.S. et al., "Prevalence of age-related macular degeneration in the United States," Arch. Ophthalmol., vol. 122, No. 4, pp. 564-572, Apr. 2004.
Greene et al., "Protective Groups in Organic Synthesis," 3rd Edition, John Wiley and Sons, Inc., New York, (1999). In 52 pages.
Gillies, et al., "Dendrimers and Dedritic Polymers in Drug Delivery," Drug Delivery today, Jan. 2005, vol. 10, No. 1, pp. 35-43.
Haddleton, et al., "Phenolic Ester-Based Initiators for Transition Metal Mediated Living Polymerization," Macromolecules, (1999), 32, pp. 8732-8739.
Haishima, Y et al. Estimation of uncertainty in kinetic-colorimetric assay of bacterial endotoxins, J Pharm Biomed Analysis, 32:1, pp. 495-503, (2003).
Haupt, H. et al., "Isolierung und physikalisch-chemische Charakterisierung der Cholinesterase aus Humanserum," Blut, vol. 14, Issue 2, pp. 65-75, Nov. 1966.
Heise et al., "Starlike Polymeric Architectures by Atom Transfer Radical Polymerization: Templates for the Production of Low Dielectric Constant Thin Films," Macromolecules, Jan. 17, 2000, 33:2346-2354.
Heise, et al., "Investigation of the Initiation Behavior of a Dendritic 12-Arm Initiator in Atom Transfer Radical Polymerization," Macromolecules, (2001), 34:11, pp. 3798-3801.
Heredia, et al., "In Situ Preparation of Protein-'Smart' Polymer Conjugates with Retention of Bioactivity," J. Am. Chem. Soc., (2005), 127, pp. 16955-16960.

(56) References Cited

OTHER PUBLICATIONS

Hirayama, C. et al., "Chromatographic removal of endotoxin from protein solutions by polymer particles," Journal of Chromatography B, vol. 781, Issues 1-2, pp. 419-432, Dec. 5, 2002.
Hoffmann, S. et al., "International validation of novel pyrogen tests based on human monocytoid cells," Journal of Immunological Methods, vol. 298, Issues 1-2, pp. 161-173, Mar. 2005.
Holash, J et al. VEGF-Trap: A VEGF Blocker with Potent Antitumor Effects, PNAS, vol. 9, No. 17, pp. 11393-11398, (2002).
Hong, et al., "Preparation of Segmented Copolymers in the Presence of an Immobilized/Soluble Hybrid ATRP Catalyst System," Macromolecules, (2003), 36:1, pp. 27-35.
Huang, Y-S. et al., "Engineering a pharmacologically superior form of granulocyte-colony-stimulating factor by fusion with gelatin-like-protein polymer," European Journal of Pharmaceutics and Biopharmaceutics, vol. 74, Issue 3, pp. 435-441, Mar. 2010.
Humphreys et al., "Alternative antibody FAB' fragment PEGylation strategies: combination of strong reducing agents, disruption of the interchain disulphide bond and disulphide engineering," Protein Engineering, Design & Selection, vol. 20, No. 5, pp. 227-234, 2007.
Huston, James S., "Protein engineering of single-chain Fv analogs and fusion proteins," Methods of Enzymology, vol. 203, pp. 46-96, 1991.
Ishikawa, K. et al., "Molecular mechanisms of subretinal fibrosis in age-related macular degeneration," Experimental Eye Research, vol. 142, pp. 19-25, Jan. 2016.
Iwasaki, et al., "Platelet compatible blood filtration fabrics using a phosphorylcholine polymer having high surface mobility," Biomaterials, (2003), 24 pp. 3599-3604.
Iwasaki, Yasuhiko et al., "Synthesis and Characterization of Amphiphilic Polyphosphates with hydrophilic graft chains and Cholesteryl Groups as Nanocarriers", Biomacromolecules, 2006, 7, 1433-1438.
Jakubowski, et al., "Activators Regenerated by Electron Transfer for Atom Transfer Radical Polymerization of Styrene," Macromolecules, (2006), 39:1, pp. 39-45.
Jankova, et al., "Star Polymers by ATRP of Styrene and Acrylates Employing Multifunctional Initiators," Journal of Polymer Science Part A: Polymer Chemistry, Mar. 30, 2005, vol. 43, pp. 3748-3759.
Janssen, Alzheimer Immunotherapy Research & Development, LLC, AAB-001 in Patients With Mild to Moderate Alzheimer's Diesear, Clinical Trials, gov, NIH, 2005, [retrieved on Jun. 19, 2012]. Retreived from the Internet: <http://clinicaltrials.gov/ct2/show/NCT00112073?term=aab-001&rank=3>.
Jeon, et al., "Synthesis of High Molecular Weight 3-Arm Star PMMA by ARGET ATRP," Macromolecular, 17:4 pp. 240-244, (2009).
Jo, N. et al., "Inhibition of platelet-derived growth factor B signaling enhances the efficacy of anti-vascular endothelial growth factor therapy in multiple models of ocular neovascularization," American Journal of Pathology, vol. 168, No. 6, pp. 2036-2053, Jun. 2006.
Jones, A., Analysis of Polypeptides and Proteins, Adv. Drug Delivery Rev. 10:, pp. 29-90, (1993).
Junghans, R.P., "Anti-Tac-H, a humanized antibody to the interleukin 2 receptor with new features for immunotherapyin malignant and immune disorders," Cancer Research, vol. 50, pp. 1495-1502, Mar. 1, 1990.
Kabat, E.A. et al., "Sequences of proteins of immunological interest," in 10 pages, 1991.
Kempen, J, et al. The Prevalence of Diabetic Retinopathy Among Adults in the United States, Arch Opthalmol., vol. 122, pp. 532-563, (2004).
Kizhakkedathu, et al., "Synthesis of Well-Defined Environmentally Responsive Polymer Brushes by Aqueous ATRP," Macromolecules, (2004), 37:3, pp. 734-743.
Kostelny, S.A. et al., "Formation of a bispecific antibody by the use of leucine zippers," J. Immunol., vol. 148, No. 5, pp. 1547-1553, Mar. 1, 1992.
Kuhnert, F. et al. "Soluble receptor-mediated selective inhibition of VEGFR and PDGFR_signaling during physiologic and tumor angiogenesis", PNAS, vol. 105, No. 29, pp. 10185-10190, (2008).

Kumar et al., "PDGF-DD targeting arrests pathological angiogenesis by modulating GSK3β phosphorylation," JBC Papers in Press, published on Mar. 15, 2010 as Manuscript M110.113787, retrieved on Jun. 18, 2015 from http://www.jbc.org; However, as this item is accessible on the world wide web, it may have been available in some form at an earlier point in time.
Kumar, A. et al., "Platelet-derived growth factor-DD targeting arrests pathological angiogenesis by modulating glycogen synthase kinase-3β phosphorylation," The Journal of Biological Chemistry, vol. 285, No. 20, pp. 15500-15510, May 14, 2010.
Kwiatdowski, et al., "High Molecular Weight Polymethacrylates by AGET ATRP under High Pressure," Macromolecules, (2008), 41:4, pp. 1067-1069.
Lacciardi, et al., "Synthesis of Novel Folic Acid-Functionalized Biocompatible Block Copolymers by Atom Transfer Radical Polymerization for Gene Delivery and Encapsulation of Hydrophobic Drugs," Biomacromolecules, (2005), 6:2, pp. 1085-1096.
Lafaut et al., "Clinicopathological correlation in exudative age related macular degeneration: histological differentiation between classic and occult choroidal neovascularisation," Br J Ophthalmol, vol. 84, pp. 239-243, 2000.
Lena, et al., "Investigation of metal ligand affinities of atom transfer radical polymerization catalysts with a quadrupole ion trap," Dalton Transactions, (2009), 41, pp. 8884-8889.
Lewis, et al., "Crosslinkable coatings from phosphorylcholine-based polymers," Biomaterials, (2001), 22, pp. 99-111.
Lewis, et al., "Poly(2-methacryloyloxyethyl phosphorylcholine) for Protein Conjugation," Bioconjugate Chem., (2008), 19:11, pp. 2144-2155.
Liu, et al., "Syntheses and Micellar Properties of Well-Defined Amphiphilic AB2 and A2B Y-Shaped Miltoarm Star Copolymers of ε-Caprolactone and 2-(Dimethylamino) ethyl Methacdrylate," Journal of Polymer Science: Part A: Polymer Chemistry, DOI 10.1002/pola, published online in Wiley InterSciences (www.intersience.wiley.com), Sep. 22, 2006; accepted Nov. 23, 2006.
Lucentis ramibizumab (reb) Name of the Medicine, Active ingredient Ranibizumab, Product Information Sheet, in 30 pages, based on CDS dated Aug. 30, 2013.
Lutz, et al., "Preparation of Ideal PEG Analogues with a Tunable Thermosensitivity by Controlled Radical Copolymerization of 2-(2-Methoxyethoxy)ethyl Methacrylate and Oligo(ethylene glycol) Methacrylate," Macromolecules, (2006), 39:2, pp. 893-896.
Ma, et al., "Synthesis of Biocompatible Polymers. 1. Homopolymerization of 2-Methacryloyloxyethyl Phosphorylcholine via ATRP in Protic Solvents: An Optimization Study," Macromolecules, (2002), 35:25, pp. 9306-9314.
Ma, et al., "Well-Defined Biocompatible Block Copolymers via Atom Transfer Radical Polymerization of 2-Methacryloyloxyethyl Phosphorylcholine in Protic Media," Macromolecules, (2003), 36:10, pp. 3475-3484.
Mabry, R. et al., "A dual-targeting PDGFRβ/VEGF-A molecule assembled from stable antibody fragments demonstrates anti-angiogenic activity in vitro and in vivo", Landes Bioscience, vol. 2, Issue 2, pp. 20-34 (2010).
Maccallum, R. et al., Antibody-Antigen Interactions: Contact Analysis and Binding Site Toopgraphy, J/. Mol Biol., vol. 262, pp. 732-745, (1996).
Magalhaes et al., "Methods of Endotoxin Removal from Biological Preparations: a Review," J. Pharm Pharmaceut Sci., vol. 10, No. 3, pp. 388-404, 2007.
Mantovani, et al., "Design and Synthesis of N-Maleimido-Functionalized Hydrophilic Polymers via Copper-Mediated Living Radical Polymerization: A Suitable Alternative to PEGylation," J. Am. Chem. Soc., (2005), 127, pp. 2966-2973.
Marticorena, J. et al., "Sterile endophthalmitis after intravitreal injections," Mediators of Inflammation, vol. 2012, 6 pages, (2012).
Masson, P. et al., "Expression and Refolding of Functional Human butyrylcholinesterase from E. coli", Multidisciplinary Approaches to Cholinesterase Functions, New York, pp. 49-52, 1992.
Matyjaszewski, et al., "Diminishing catalyst concentration in atom transfer radical polymerization with reducing agents," PNAS, (Oct. 17, 2006), 103:42, pp. 15309-15314.

(56) References Cited

OTHER PUBLICATIONS

McPherson, D. et al., "Production and Purification of a Recombinant Elastomeric Polypeptide, G-(VPGVG)19-VPGV, from *Escherichia coli*," Biotechnology Process, vol. 8, Issue 4, pp. 347-352, Jul./Aug. 1992.
McRae, et al. "Pentafluorophenyl Ester-Functionalized Phosphorylcholine Polymers: Preparation of Linear, Two-Arm, and Grafted Polymer-Protein Conjugates," Biomacromolecules, 13, 2099-2109 (2012).
Meng, X. et al. New Generation Recombinant hBuChe-FC Fusion with In-Vivo Performance Equivilanet to Gold Standard Plasma-Derive hbuChe-A First-in-Class Broad Spectrum Bioscanvenger that is Sustainable, Scalable, and Highly Cost-Effective on a Troop-Equivalent-Dose (TED) Basis.
Min, et al., "Use of Ascorbic Acid as Reducing Agent for Synthesis of Well-Defined Polymers by ARGET ATRP," Macromolecules, (2007), 40:6, pp. 1789-1791.
Miyamoto, et al., "Effect of water-soluble Phospholipid polymers conjugated with papain on the enzymatic stability," Biomaterials, (2004), 25, pp. 71-76.
Mones, Jordi, Inhibiting VEGF and PDGF to Treat AMD, http://www.reviewofophthalmology.com/content/d/retinal_insider/c/29979/#stash.fJePfjQ4.dpuf, Spain, Sep. 9, 2011.
Morris, G.E., "Epitope mapping protocols in methods in molecular biology," vol. 66, 1996.
Neuberger, M., "Generating high-avidity human Mabs in mice," Nature Biotechnology, vol. 14, pp. 826, 1996.
Ng, et al., "Successful Cu-Mediated Atom Transfer Radical Polymerization in the Absence of Conventional Chelating Nitrogen Ligans," Macromolecules, (2010), 43:2, pp. 592-594.
Ogikubo, Y. et al., "Evaluation of the bacterial endotoxin test for quantification of endotoxin contamination of porcine vaccines," Biologicals, vol. 32, Issue 2, pp. 88-93, Jun. 2004.
Oh, et al., "Preparation of Poly(oligo(ethylene glycol) monomethyl ether methacrylate) by Homogeneous Aqueous AGET ATRP," Macromolecules, (2006), 39:9, pp. 3161-3167.
Ong, K. et al., "A rapid highly-sensitive endotoxin detection system," Biosensors and Bioelectronics, vol. 21, Issue 12, pp. 2270-2274, Jun. 15, 2006.
Ostberg, L. et al., "Human X (mouse X human) hybridomas stably producing human antibodies," Hybridoma, vol. 2, No. 4, pp. 361-367, 1983.
Padlan, Eduardo A., "A possible procedure for reducing the immunogenicity of antibody variable domains while preserving their ligand-binding properties," Molecular Immunology, vol. 28, Issues 4-5, pp. 489-498, Apr.-May 1991.
Palma, et al., "A new bispphosphonate-containing 99mTc(I) tricarbonyl complex potentially useful as bone-seeking agent: synthesis and biological evaluation," J Biol Inorg Chem, 12:667-679, (2007).
Papadopoulos et al., "Binding and neutralization of vascular endothelial growth factor (VEGF) and related ligands by VEGF Trap, ranibizumab and bevacizumab," Angiogenesis, vol. 15, pp. 171-185, 2012.
Pasut, et al., "Protein peptide and non-peptide drug PEGylation for therapeutic application," Expert Opin. Ther. Patents, 14(6) 859-894 (2004).
Paul, W., Fundamental Immunology, 2nd ed. Raven Press, N.Y., (1989).
Petsch, D. et al., "Endotoxin removal from protein solutions," Journal of Biotechnology, vol. 76, Issues 2-3, pp. 97-119, Jan. 21, 2000.
Pennock, S. et al Vascular Endothelial Growth Factor A Competitively Inhibits Platelet-Derived Growth Factor (PDGF)-Dependent Activation of PDGF Receptor and Subsequent Signaling Events and Cellar Responses, Molecular and Cell Biology, vol. 32, No. 2, pp. 1955-1966, (2012).
Pietrasik, et al., "Synthesis of High Molecular Weight Poly(styrene-co-acrylonitrile) Copolymers with Controlled Architecture," Macromolecules, (2006), 39:19, pp. 6384-6390.

Pratt, et al. End-Functionalized Phosphorycholine Methacrylate and Their Use in Protein Conjugation, Biomacromlecules, vol. 9, pp. 2891-2897, (2008).
Presta et al., "Humanization of an Anti-Vascular Endothelial Growth Factor Monoclonal Antibody for the Therapy of Solid Tumors and Other Disorders," Cancer Research, vol. 57, pp. 4593-4599, 1997.
Raetz, C.R. et al., "Gram-negative endotoxin: an extraordinary lipid with profound effects on eukaryotic signal transduction," The FASEB Journal, vol. 5, No. 12, pp. 2652-2660, Sep. 1991.
Raica, M. et al., "Platelet-derived growth factor (PDGF)/PDGF receptors (PDGFR) axis as target for antitumor and antiangiogenic therapy," Pharmaceuticals, vol. 3, No. 3, pp. 572-599, (2010).
Ranganathan, et al., "Synthesis of Thermoresponsive Mixed Arm Star Polymers by Combination of RAFT and ATRP from a Multifunctional Core and Its Self-Assembly in Water," Macromolecules, (2008), 41:12, pp. 4226-4234.
*Regeneron Pharmaceuticals Inc.* vs. *Bayer Pharma AG* Approved Judgment dated Feb. 21, 2013.
Regillo, C. et al., "Randomized, double-masked, sham-controlled trial of ranibizumab for neovascular age-related macular degeneration: PIER Study Year 1," American Journal of Ophthalmology, vol. 145, Issue 2, pp. 239-248, Feb. 2008.
Roberts et al., "Chemistry for Peptide and Protein PEGylation," Advanced Drug Delivery Reviews 2002 54:459-476.
Roberts, W.G. et al., "Increased microvascular permeability and endothelial fenestration induced by vascular endothelial growth factor," Journal of Cell Science, vol. 108, pp. 2369-2379, (1995).
Rosenfeld, P. et al., "Ranibizumab for neovascular age-related macular degeneration," The New England Journal of Medicine, vol. 355, No. 14, pp. 1419-1431, Oct. 5, 2006.
Rudikoff, S. et al, Single Amino Acid Substituon Altering Antigen-Bidning Specificity, Proc Natl. Acad. Sci. USA, vol. 79, pp. 1979-1983, (1982).
Ruiz, et al., "Synthesis structure and surface dynamics of phosphorylcholine functional biomimicking polymers," Biomaterials, (1998), 19, pp. 987-998.
Ryan, et al., "Conjugation of salmon calcitonin to a combed-shaped end functionalized poly(poly(ethylene glycol) methyl ether methacrylate) yields a bioactive stable conjugate," Journal of Controlled Release, (2009), 135 pp. 51-59.
Rycroft, B.W., "Penicillin and the control of deep intra-ocular infection," British J. Ophthalmol, vol. 29, No. 2, pp. 57-87, Feb. 1945.
Sakaki, et al., "Stabilization of an antibody conjugated with enzyme by 2-methacryloyloxyethyl phosphorylcholine copolymer in enzyme-linked immunosorbent assay," J Biomed Mater Res, (1999), 47, pp. 523-528.
Samanta, et al., "End-Functionalized Phosphorylcholine Methacrylates and their Use in Protein Conjugation," Biomacromolecules, (2008), 9:(10), pp. 2891-2897.
Sayers, et al., "The Reduced Viscosity of PolyPEG® Compared with Linear PEG," WEP designer polymers, www.wep-ltd.co.uk, in 1 page, Feb. 11, 2009.
Schellenberger, V. et al., "A recombinant polypeptide extends the in vivo half-life of peptides and proteins in a tunable manner," Nature Biotechnology, vol. 27, pp. 1186-1190, 2009.
Schlapschy, M. et al., "Fusion of a recombinant antibody fragment with a homo-amino-acid polymer: effects on biophysical properties and prolonged plasma half-life," Protein Eng Des Sel, vol. 20, Issue 6, pp. 273-284, Jun. 1, 2007.
Seo et al., "Conformational Recovery and Preservation of Protein Nature from Heat-Induced Debaturation by Water-Soluble Phospholipid Plymer Conjugation," Biomaterials, vol. 30, 2009, pp. 4859-4867.
Shim et al., "Structures of a platelet-derived growth factor/propeptide complex and a platelet-derived growth factor/receptor complex," PNAS, vol. 107, No. 25, pp. 11307-11312, 2010.
Songsivilai, S. et al., "Bispecific antibody: a tool for diagnosis and treatment of disease," Clin Exp. Immunol., vol. 79, No. 3, pp. 315-321, Mar. 1990.
Stuttfeld et al., "Structure and function of VEGF receptors," Life, vol. 61, No. 9, pp. 915-922, 2009.

(56) References Cited

OTHER PUBLICATIONS

Tamura, M. et al., "Structural correlates of an anticarcinoma antibody: Identification of specificity-determining residues (SDRs) and development of a minimally immunogenic antibody variant by retention of SDRs only," The Journal of Immunology, vol. 164, No. 3, pp. 1432-1441, Feb. 1, 2000.
Tao, et al., "α-Aldehyde Terminally Functional Methacrylic Polymers from Living Radical Polymerization: Application in Protein Conjugation 'Pegylation'," J. Am. Chem. Soc., (2004), 126:41, pp. 13220-13221.
Tonkinson, J. et al., "New Drugs: Antisense Oligodeoxynucleotides as Clinical Therapeutic Agents," Cancer Investigation, vol. 14, No. 1, pp. 54-65, 1996.
Ueda, et al., "Preparation of 2-Methacryloyloxyethyl Phosphocrycholine Copolymers with Alkyl Methacrylates and their Blood Campatability," Polymer Journal, vol. 24, No. 11, pp. 1259-1269 (1992).
Uutela et al., "PDFG-D induces macrophage recruitment, increased intersitial pressure, and blood vessel maturation during angiogenesis," Blood, vol. 104, No. 10, pp. 3198-3204, Nov. 15, 2004.
Vajdos, F. et al., "Comprehensive functional maps of the antigen-binding site of an anti-ErbB2 antibody obtained with shotgun scanning mutagenesis," Journal of Molecular Biology, vol. 320, Issue 2, pp. 415-428, Jul. 5, 2002.
Venditto, et al., "Cancer Therapies Utilizing the Camtothecins: A Review of the Vivo Literature," Molecular Pharmaceutics, vol. 7, No. 2, pp. 307-349 (2010).
Voynov et al., "Design and application of antibody cysteine variants," Bioconjugate Chemistry, vol. 21, pp. 385-392, Jan. 21, 2010.
Wagner, E. et al., "Transferrin-polycation conjugates as carriers for DNA uptake into cells," Proc. Natl. Acad. Sci. USA, vol. 87, No. 9, pp. 3410-3414, May 1, 1990.
Wang, et al., "Controlled/'Living' Radical Polymerization. Atom Transfer Radical Polymerization in the Presence of Transition-Metal Complexes," J. Am. Chem. Soc., (1995), 117:20, pp. 5614-5615.
Wang, et al., "Synthesis and Evaluation of Water-Soluble Polymers Bone-Targeted Drug Delivery Systems," Bioconjugate Chem., 14, 853-859 (2003).
Warwick Effect Polymers, PowerPoint presentation, "Polymers for the Healthcare and Specialty Materials Industries," Jan. 2009, pp. 1-29.
Wu, G.Y. et al. "Receptor-mediated in vitro gene transformation by a soluble DNA carrier system," Journal of Biological Chemistry, vol. 262, pp. 4429-4432, Apr. 5, 1987.
Wu, H et al., Humanization of a Murine Monoclonal Antibody by Simultaneous Optimization of Frameork and CDR Resiudes, J. Mol. Biol., vol. 294, pp. 151-162, (1999).
Yaseen, et al., "The Structure of Zwitterionic Phosphoacholine Surfactant Monolayers," Langmuir, (2006), 22:13, pp. 5825-5832.
Yeh, P. et al., "Design of yeast-secreted albumin derivatives for human therapy: biological and antiviral properties of a serum albumin-CD4 genetic conjugate," Proc Natl Acad Sci USA, vol. 89, No. 5, pp. 1904-1908, Mar. 1, 1992.
Yu, L et al. Internaction Between Bevacizumab and Murie VEGF-A: A Reassessment, Investigative Opthalmology & Visual Science, vol. 49, No. 2, pp. 522-527, (2008).
Yusa, et al., "Synthesis of Well-Defined Amphiphilic Block Copolymers Having Phospholipid Polymer Sequences as a Novel biocompatible Polymer Micelle Reagents," Biomacromolecules, 6, 663-670 (2005).
Zebrowski, B. et al., "Vascular endothelial growth factor levels and induction of permeability in malignant pleural effusions," Clinical Cancer Research, vol. 5, pp. 3364-3368, Nov. 1999.
Zetter, "Angiogenesis and Tumor Metastasis," Annu. Rev. Med., vol. 49, pp. 407-424, 1998.
Zhang, X et al., Prevalence of Diabetic Retinopathy in the United States, 2005-2008, JAMA. vol. 304, No. 6, pp. 649-656, (2010).
Advisory Action dated Jun. 12, 2014 in U.S. Appl. No. 13/959,563.
Extended European Search Report received in European Patent Application No. 17165316.5 dated Aug. 2, 2017.
Extended European Search Report received in European Patent Application No. 17181272.0 dated Feb. 23, 2018 in.
Extended European Search Report dated Mar. 21, 2016 in EP Application No. 11769715.1, dated Jul. 18, 2016 s.
Extended Search Report received in European Patent Application No. 14841835.3 dated Mar. 14, 2017.
First Examination Report in NZ Application No. 6009449, dated Mar. 14, 2013.
First Examination Report in NZ Application No. 603048, dated Jun. 13, 2013 in 2 pages.
International Preliminary Report on Patentability dated Feb. 11, 2014 in PCT Application Np. PCT/US2011/32768.
International Preliminary Report on Patentability (IPRP) dated Jun. 24, 2014, in International Application No. PCT/IB2012/057491, 10 pages.
International Preliminary Report on Patentability (IPRP) dated Jul. 5, 2016, in International Application No. PCT/US2015/038203.
International Preliminary Report on Patentability dated Jul. 3, 2018 for International Patent Application No. PCT/US2016/069336 filed Dec. 29, 2016.
International Search Report and Written Opinion dated Feb. 27, 2013 in Internatnional Application No. PCT/US2012/060301.
International Search Report and Written Opinion for PCT/US2018/027378 dated Sep. 27, 2018.
International Search Report and Written Opinion dated Mar. 30, 2017 for International Patent Application No. PCT/US2016/069336 filed Dec. 29, 2016.
International Search Report in PCT Application No. PCT/US2007/005372, dated Aug. 8, 2008.
International Search Report and Written Opinion dated Sep. 9, 2010 in PCT Application No. PCT/US2010/034252.
International Search Report and Written Opinion dated May 9, 2011 in PCT Application No. PCT/US2010/61358.
International Search Report and Written Opinion dated Dec. 16, 2011 in PCT Application Np. PCT/US2011/327681.
International Search Report and Written Opinion for PCT/US2015/038203, dated Dec. 8, 2015.
International Search Report dated Jun. 4, 2013, in International Application No. PCT/IB2012/057491.
Notice of Allowance dated Jul. 31, 2014 in U.S. Appl. No. 13/959,563.
Notice of Allowance dated Sep. 26, 2018 in Canadian Patent Application No. 2,783,615.
Notice of Allowance dated Jan. 28, 2014 in U.S. Appl. No. 13/515,913.
Notice of Allowance dated Aug. 9, 2017 in U.S. Appl. No. 14/753,824.
Notice of Final Rejection received in Korean Patent Application No. 10-2012-7029878 dated Aug. 28, 2017.
Notice of Final Rejection received in Korean Patent Application No. 10-2012-7029878 dated Oct. 27, 2017.
Notice of Rejection received in Japanese Patent Application No. 2016-159104 dated Jun. 27, 2017.
Notice of Rejection received in Japanese Patent Application No. 2016-159104 dated Feb. 26, 2018.
Notice to File a Response received in Korean Patent Application No. 10-2012-7018788 dated Sep. 13, 2017.
Office Action dated Jun. 21, 2018 in U.S. Appl. No. 15/394,500.
Office Action dated Jan. 7, 2019 in U.S. Appl. No. 15/394,500.
Office Action in U.S. Appl. No. 13/959,563, dated Oct. 10, 2013.
Office Action in U.S. Appl. No. 13/959,563, dated Feb. 20, 2014.
Office Action in U.S. Appl. No. 14/456,875, dated Jun. 9, 2015.
Office Action in U.S. Appl. No. 14/456,875, dated Oct. 5, 2016 in 10 pages.
Office Action in U.S. Appl. No. 14/456,875, dated Apr. 20, 2017.
Office Action in U.S. Appl. No. 14/456,875, dated Dec. 14, 2017.
Office Action in U.S. Appl. No. 14/456,875, dated Aug. 28, 2018.
Office Action dated Feb. 7, 2012 in U.S. Appl. No. 12/281,071.
Office Action in JP Patent Application No. 2008-557399, dated May 25, 2013.
Office Action in CA Application No. 2783615, dated Sep. 16, 2016.
Office Action in CA Application No. 2783615, dated Jan. 9, 2018.
Office Action dated Dec. 14, 2015 in U.S. Appl. No. 14/265,174.
Office Action in EP Application No. 10838353.0, dated Oct. 4, 2016.
Office Action in European Patent Application No. 17181272.0 dated Oct. 31, 2018.

(56) References Cited

OTHER PUBLICATIONS

Office Action in JP Application No. 2012-544945, dated Jul. 9, 2014.
Office Action in JP Application No. 2016-159104, dated Jun. 27, 2017.
Office Action dated Feb. 8, 2018 in Indian Patent Application No. 6116/CHENP/2012.
Office Action dated Dec. 31, 2013 in U.S. Appl. No. 13/516,173.
Office Action dated Jul. 2, 2014 in U.S. Appl. No. 13/516,173.
Office Action dated Dec. 16, 2014 in U.S. Appl. No. 13/516,173.
Office Action dated May 30, 2017 U.S. Appl. No. 15/099,234.
Office Action dated Oct. 19, 2018 U.S. Appl. No. 15/099,234.
Office Action dated Apr. 12, 2018 in Australian Patent Application Np. 2017201930.
Office Action dated Jun. 2, 2016 U.S. Appl. No. 13/901,483.
Office Action dated Feb. 9, 2018 in U.S. Appl. No. 15/368,376.
Office Action dated Sep. 10, 2018 in U.S. Appl. No. 15/368,376.
Office Action dated Apr. 6, 2017 Canadian Patent Application No. 2,795,667.
Office Action dated Dec. 29, 2017 Canadian Patent Application No. 2,795,667.
Office Action in CN Application No. 201180028682.1, dated Aug. 21, 2014.
Office Action in CN Application No. 201180028682.1, dated Jan. 26, 2015.
Office Action in CN Application No. 20118002868.1, dated Aug. 11, 2015.
Office Action received in European Patent Application No. 11769715.1 dated Nov. 9, 2017.
Office Action in JP Application No. 2013-505799, dated Feb. 19, 2015.
Office Action in JP Application No. 2015-165282, dated Aug. 15, 2016.
Office Action in JP Application No. 2015-165282, dated Aug. 1, 2017.
Office Action in JP Application No. 2015-165282, dated Sep. 27, 2018.
Office Action dated Nov. 27, 2018 in Japanese Patent Application No. JP 2017-231724.
Office Action in KR Application No. 10-2012-7029878, dated Mar. 8, 2017.
Office Action dated Mar. 9, 2018 in KR Application No. 10-217-703456.
Office Action dated Aug. 28, 2018 in KR Application No. 10-217-703456.
Office Action dated Jul. 13, 2018 in Japanese Patent Application No. 2016-540916.
Office Action dated Feb. 27, 2017 in U.S. Appl. No. 14/753,824.
Office Action dated Jan. 9, 2019 in U.S. Appl. No. 15/820,325.
Office Action dated Jun. 27, 2018 in Indian Patent Application No. 9476/CHENP/2012 in 5 pages.
Patent Examination Report No. 1 in AU Application No. 2010330727, dated Nov. 19, 2014.
Patent Examination Report in AU Application No. 2011239434, dated Mar. 19, 2014.
Patent Examination Report in AU Application No. 2015207898, dated Mar. 23, 2016.
Patent Examination Report in AU Application No. 2015207898, dated May 27, 2017.
Restriction Requirement dated Mar. 7, 2018 in U.S. Appl. No. 15/394,500.
Restriction Requirement dated Jun. 20, 2011 in U.S. Appl. No. 12/28107.
Restriction Requirement dated Jul. 15, 2015 in U.S. Appl. No. 14/265,174.
Restriction Requirement dated Aug. 14, 2013 in U.S. Appl. No. 13/515,913.
Restriction Requirement dated Sep. 3, 2013 in U.S. Appl. No. 13/516,173.
Restriction Requirement dated Feb. 9, 2017 U.S. Appl. No. 15/099,234.
Restriction Requirement dated Nov. 3, 2015 U.S. Appl. No. 13/901,483.
Restriction Requirement dated Aug. 21, 2017 in U.S. Appl. No. 15/368,376.
Supplemental European Search Report received in European Patent Application No. EP 07752096.3 dated Feb. 19, 2013.
Supplemental European Search Report dated Feb. 2, 2015 in European Patent Application No. EP 10838353.0 dated Feb. 2, 2015.
File History of U.S. Appl. No. 15/952,092, filed Apr. 12, 2018.
File History of U.S. Appl. No. 15/394,500, filed Dec. 29, 2016.
File History of U.S. Appl. No. 14/456,875, filed Aug. 11, 2014.
File History of U.S. Appl. No. 15/099,234, filed Apr. 14, 2016.
File History of U.S. Appl. No. 15/368,376, filed Dec. 2, 2016.
File History of U.S. Appl. No. 15/820,325, filed Nov. 21, 2017.
Office Action Received in Chinese Patent Application No. 201080062252.7 dated Apr. 20, 2017.
Office Action Received in Chinese Patent Application No. 201610439969.8 dated Jul. 24, 2018.
Office Action in KR Application No. 10-2012-7018788, dated Mar. 10, 2017.
Office Action received in Chinese Patent Application No. 201610446624.5 dated Mar. 12, 2018 in 12 pages.
Office Action received in Chinese Patent Application No. 201610446624.5 dated Nov. 26, 2018.
Office Action dated Oct. 26, 2018 in KR Application No. 10-2017-703456.
Office Action received in Mexican Patent Application No. MX/a/2012/011876 dated Jul. 13, 2017.
Office Action dated Jan. 16, 2018 in MX Application No. MX/a/2012/011876.
Office Action dated Jan. 23, 2019 in European Patent Application No. EP 14841835.3.
Office Action dated Jun. 6, 2018 in Mexican patent Application No. MX/a/2012/011876.
Office Action dated Dec. 17, 2018 in Mexican patent Application No. MX/a/2012/011876.
Office Action, European Patent Office, Application No. 14 841 832.3, dated Jan. 23, 2019, in 5 pages.

\* cited by examiner

FIG 1. FULL LENGTH FVIII SEQUENCE

```
ATRRYYLGAV ELSWDYMQSD LGELPVDARF PPRVPKSFPF NTSVVYKKTL FVEFTDHLFN   60
IAKPRPPWMG LLGPTIQAEV YDTVVITLKN MASHPVSLHA VGVSYWKASE GAEYDDQTSQ  120
REKEDDKVFP GGSHTYVWQV LKENGPMASD PLCLTYSYLS HVDLVKDLNS GLIGALLVCR  180
EGSLAKEKTQ TLHKFILLFA VFDEGKSWHS ETKNSLMQDR DAASARAWPK MHTVNGYVNR  240
SLPGLIGCHR KSVYWHVIGM GTTPEVHSIF LEGHTFLVRN HRQASLEISP ITFLTAQTLL  300
MDLGQFLLFC HISSHQHDGM EAYVKVDSCP EEPQLRMKNN EEAEDYDDDL TDSEMDVVRF  360
DDDNSPSFIQ IRSVAKKHPK TWVHYIAAEE EDWDYAPLVL APDDRSYKSQ YLNNGPQRIG  420
RKYKKVRFMA YTDETFKTRE AIQHESGILG PLLYGEVGDT LLIIFKNQAS RPYNIYPHGI  480
TDVRPLYSRR LPKGVKHLKD FPILPGEIFK YKWTVTVEDG PTKSDPRCLT RYYSSFVNME  540
RDLASGLIGP LLICYKESVD QRGNQIMSDK RNVILFSVFD ENRSWYLTEN IQRFLPNPAG  600
VQLEDPEFQA SNIMHSINGY VFDSLQLSVC LHEVAYWYIL SIGAQTDFLS VFFSGYTFKH  660
KMVYEDTLTL FPFSGETVFM SMENPGLWIL GCHNSDFRNR GMTALLKVSS CDKNTGDYYE  720
DSYEDISAYL LSKNNAIEPR SFSQNSRHPS TRQKQFNATT IPENDIEKTD PWFAHRTPMP  780
KIQNVSSSDL LMLLRQSPTP HGLSLSDLQE AKYETFSDDP SPGAIDSNNS LSEMTHFRPQ  840
LHHSGDMVFT PESGLQLRLN EKLGTTAATE LKKLDFKVSS TSNNLISTIP SDNLAAGTDN  900
TSSLGPPSMP VHYDSQLDTT LFGKKSSPLT ESGGPLSLSE ENNDSKLLES GLMNSQESSW  960
GKNVSSTESG RLFKGKRAHG PALLTKDNAL FKVSISLLKT NKTSNNSATN RKTHIDGPSL 1020
LIENSPSVWQ NILESDTEFK KVTPLIHDRM LMDKNATALR LNHMSNKTTS SKNMEMVQQK 1080
KEGPIPPDAQ NPDMSFFKML FLPESARWIQ RTHGKNSLNS GQGPSPKQLV SLGPEKSVEG 1140
QNFLSEKNKV VVGKGEFTKD VGLKEMVFPS SRNLFLTNLD NLHENNTHNQ EKKIQEEIEK 1200
KETLIQENVV LPQIHTVTGT KNFMKNLFLL STRQNVEGSY DGAYAPVLQD FRSLNDSTNR 1260
TKKHTAHFSK KGEEENLEGL GNQTKQIVEK YACTTRISPN TSQQNFVTQR SKRALKQFRL 1320
PLEETELEKR IIVDDTSTQW SKNMKHLTPS TLTQIDYNEK EKGAITQSPL SDCLTRSHSI 1380
PQANRSPLPI AKVSSFPSIR PIYLTRVLFQ DNSSHLPAAS YRKKDSGVQE SSHFLQGAKK 1440
NNLSLAILTL EMTGDQREVG SLGTSATNSV TYKKVENTVL PKPDLPKTSG KVELLPKVHI 1500
YQKDLFPTET SNGSPGHLDL VEGSLLQGTE GAIKWNEANR PGKVPFLRVA TESSAKTPSK 1560
LLDPLAWDNH YGTQIPKEEW KSQEKSPEKT AFKKKDTILS LNACESNHAI AAINEGQNKP 1620
EIEVTWAKQG RTERLCSQNP PVLKRHQREI TRTTLQSDQE EIDYDDTISV EMKKEDFDIY 1680
DEDENQSPRS FQKKTRHYFI AAVERLWDYG MSSSPHVLRN RAQSGSVPQF KKVVFQEFTD 1740
GSFTQPLYRG ELNEHLGLLG PYIRAEVEDN IMVTFRNQAS RPYSFYSSLI SYEEDQRQGA 1800
EPRKNFVKPN ETKTYFWKVQ HHMAPTKDEF DCKAWAYFSD VDLEKDVHSG LIGPLLVCHT 1860
NTLNPAHGRQ VTVQEFALFF TIFDETKSWY FTENMERNCR APCNIQMEDP TFKENYRFHA 1920
INGYIMDTLP GLVMAQDQRI RWYLLSMGSN ENIHSIHFSG HVFTVRKKEE YKMALYNLYP 1980
GVFETVEMLP SKAGIWRVEC LIGEHLHAGM STLFLVYSNK CQTPLGMASG HIRDFQITAS 2040
GQYGQWAPKL ARLHYSGSIN AWSTKEPFSW IKVDLLAPMI IHGIKTQGAR QKFSSLYISQ 2100
FIIMYSLDGK KWQTYRGNST GTLMVFFGNV DSSGIKHNIF NPPIIARYIR LHPTHYSIRS 2160
TLRMELMGCD LNSCSMPLGM ESKAISDAQI TASSYFTNMF ATWSPSKARL HLQGRSNAWR 2220
PQVNNPKEWL QVDFQKTMKV TGVTTQGVKS LLTSMYVKEF LISSSQDGHQ WTLFFQNGKV 2280
KVFQGNQDSF TPVVNSLDPP LLTRYLRIHP QSWVHQIALR MEVLGCEAQD LY         2332
```

FACTOR VIII ZWITTERIONIC POLYMER CONJUGATES

CROSS-REFERENCE TO RELATED APPLICATION

The present application is a national stage of PCT/US2014/054622 filed Sep. 8, 2014, which claims the benefit of U.S. 61/875,099 filed Sep. 8, 2013 incorporated by reference it its entirety for all purposes.

REFERENCE TO A SEQUENCE LISTING

This application includes an electronic sequence listing in a file named 476152_SEQLST.txt, created on Mar. 2, 2016 and containing 19,627 bytes, which is hereby incorporated by reference in its entirety for all purposes.

BACKGROUND

Hemophilia A is a hereditary blood coagulation disorder caused by deficits of or mutations in Factor VIII (FVIII). Factor VIII is a crucial component in the intrinsic blood coagulation pathway. Deficiencies in Factor VIII cause increased bleeding. Hemophilia A is X linked and is observed in males at about 1 in 5000.

Hemophilia A patients are currently treated by intravenous administration of full length recombinant human FVIII. Treatment may be prophylactic or as necessitated in response to an injury causing bleeding. The half-life of Factor VIII in humans is relatively short, typically on the order of 11 hours. Hence, frequent dosages on the order of three times a week are required for effective treatment. However, such frequent dosing, typically via infusion, is undesirable, necessitating frequent visits to a clinic or other healthcare provider. Moreover, such frequent dosing may diminish patient compliance with prescribed dosing regimes.

Another drawback with current Factor VIII treatment is that some 25 to 30%, of Factor VII treated patients develop antibodies to FVIII. Patients with high levels of circulating anti-Factor VIII antibodies cannot be successfully treated with current Factor VIII therapeutics. Such patients require a more expensive treatment regime involving Factor VIIa and immune tolerance therapy.

The efficacy of a therapeutic agent may be enhanced by improving its bioavailability and pharmacokinetic properties. One approach to improving bioavailability has been PEGylation. PEGylation involves the addition of polyethylene glycol chains to a drug, typically a protein. A reduction in immunogenicity or antigenicity, increased half-life, increased solubility, decreased clearance by the kidney and decreased enzymatic degradation have been attributed to PEG conjugates. As a result of these attributes, it has been reported that PEG conjugates of certain biologically active agents sometimes require less frequent dosing and may permit the use of less of the active agent to achieve a therapeutic endpoint. Less frequent dosing is generally desirable because it reduces the overall number of injections, which can be painful and which require inconvenient visits to healthcare professionals.

Although some success has been achieved with PEG conjugation, "PEGylation" of biologically active agents remains a challenge. As drug developers progress beyond very potent agonistic proteins such as erythropoietin and the various interferons, potential benefits of the PEG hydrophilic polymer in increased solubility, stability and bioavailability do not sufficiently compensate for increased viscosity and immunogenicity.

PEGylation of FVIII has not been observed to significantly increase the half-life of the conjugate in vivo.

Thus there remains a need for FVIII drugs with increased in vivo half-life while retaining sufficient biological activity.

BRIEF SUMMARY OF THE CLAIMED INVENTION

The invention provides a conjugate comprising recombinant FVIII (rFVIII) and a zwitterionic polymer wherein the polymer comprises one or more monomer units and wherein at least one monomer unit comprises a zwitterionic group. Optionally, the zwitterionic group comprises phosphorylcholine. Optionally, the monomer comprises 2-(acryloyloxyethyl)-2'-(trimethylammoniumethyl) phosphate. Optionally, the monomer comprises 2-(methacryloyloxyethyl)-2'-(trimethylammoniumethyl) phosphate (HEMA-PC). The rFVIII may have a deletion of part or all of the B domain or may have an intact B-domain. Optionally, the polymer has 3 or more arms. Optionally, the polymer has 3, 4, 5, 6, 7, 8, 9, 10, 11 or 12 arms. Optionally, the polymer has 3, 6 or 9 arms, preferably the polymer has 9 arms.

Some conjugates are such that the polymer portion has a peak molecular weight of between 300,000 and 1,750,000 daltons including the rFVIII. Some conjugates have a polymer portion with a peak molecular weight between 500,000 and 1,000,000 daltons. Some conjugates have a polymer portion with a peak molecular weight between 600,000 to 800,000 daltons.

In some conjugates the rFVIII is covalently bonded to the polymer. In some conjugates, the polymer is covalently bonded to at least one of an amino group, a hydroxyl group, a sulfhydryl group and a carboxyl group of rFVIII. In some conjugates, the sulfhydryl group is from a cysteine residue in rFVIII. In some conjugates, the cysteine residue is a recombinant cysteine residue. In some conjugates, the recombinant cysteine residue is selected from the group consisting of Y81C, F129C, K377C, H378C, K422C, Q468C, L491C, L504C, K556C, K570C, D1795C, Q1796C, R1803C, K1804C, K1808C, K1810C, T1821C, K1813C, N1864C, T1911C, N2118C, Q2091C, F2093C, and Q2284C, wherein residues are numbered from corresponding residues in SEQ ID NO:1 (FIG. 1), when the recombinant Factor VIII is maximally aligned with SEQ ID NO: 1. In some conjugates, the cysteine residue is naturally present in rFVIII. In some conjugates, the cysteine residue is in the B domain. In some conjugates, the cysteine residue is selected from the group consisting of 1293C, 1373C, 1604C and 1636C, preferably 1604C or 1636C.

A preferred conjugate has a polymer portion with a peak molecular weight of between 100,000 and 1,500,000, more preferably 500,000 to 1,000,000 daltons or 600,000 to 850,000 daltons including rFVIII and 3, 6, or 9 arms, preferably 9 arms.

The invention further provides a conjugate comprising recombinant FVIII (rFVIII) with at least a portion of a B domain and a zwitterionic polymer wherein the polymer comprises one or more monomer units and wherein at least one monomer unit comprises a zwitterionic group and the polymer is conjugated to the rFVIII via a cysteine residue in the B-domain, wherein one branched polymer is conjugated per molecule of rFVIII. Optionally, the polymer is a branched polymer, optionally with 9 branches. Optionally, the polymer is conjugated via a cysteine residue that is one of the two C-terminal most cysteine residues in the portion of the B domain. Optionally, the conjugate has an in vivo half-life in humans of at least 20 hours.

The invention further provides a composition comprising molecules of a conjugate comprising recombinant FVIII (rFVIII) including a light chain and a heavy chain including at least a portion of a B domain and a zwitterionic polymer wherein the polymer comprises one or more monomer units and wherein at least one monomer unit comprises a zwitterionic group and the polymer is conjugated to the rFVIII via a cysteine residue in the B-domain, wherein at least 80, 90, 95 or 99% of molecules of the conjugate in the composition have the same portion of the B domain and one polymer is conjugated per molecule of rFVIII. Optionally, the polymer is branched, optionally with 9 branches. Optionally, the heavy chain includes at least residues 1-1604 of SEQ ID NO:1 or at least residues 1-1636 of SEQ ID NO:1, or at least residues 1-1648 of SEQ ID NO:1. Optionally, the heavy chain consists of residues 1-1648 of SEQ ID NO:1. Optionally, the at least a portion of the B domain is an intact B domain. Optionally, the polymer is conjugated via a cysteine that is one of the two most C-terminal cysteines in the B domain.

The invention further provides a pharmaceutical composition comprising a conjugate as described above.

The invention further provides a method of treating hemophilia comprising administering a therapeutically effective amount of a conjugate as described above to a subject suffering from hemophilia.

The invention further provides a method of prophylaxis of a subject with hemophilia, comprising administering a therapeutically effective amount of a conjugate or composition of any preceding claim to the subject with hemophilia at a time when the subject is not known to be bleeding externally or internally, wherein the conjugate persists in the blood so as to promote clotting after subsequent bleeding. Optionally, the conjugate or composition is administered no more frequently than once a week. Optionally, the conjugate or composition is administered between weekly and monthly. Optionally, the subject has a trough level of FVIII activity of greater than >1%, 3%, or 5% of the mean FVIII activity in control subjects without hemophilia. Optionally, the subject has developed antibodies to FVIII from previous administration of FVIII unconjugated to the polymer.

BRIEF DESCRIPTION OF THE DRAWINGS

FIG. 1 depicts the amino acid sequence of mature, human Factor VIII (SEQ ID NO:1).

DETAILED DESCRIPTION

1. General

Figure 2:
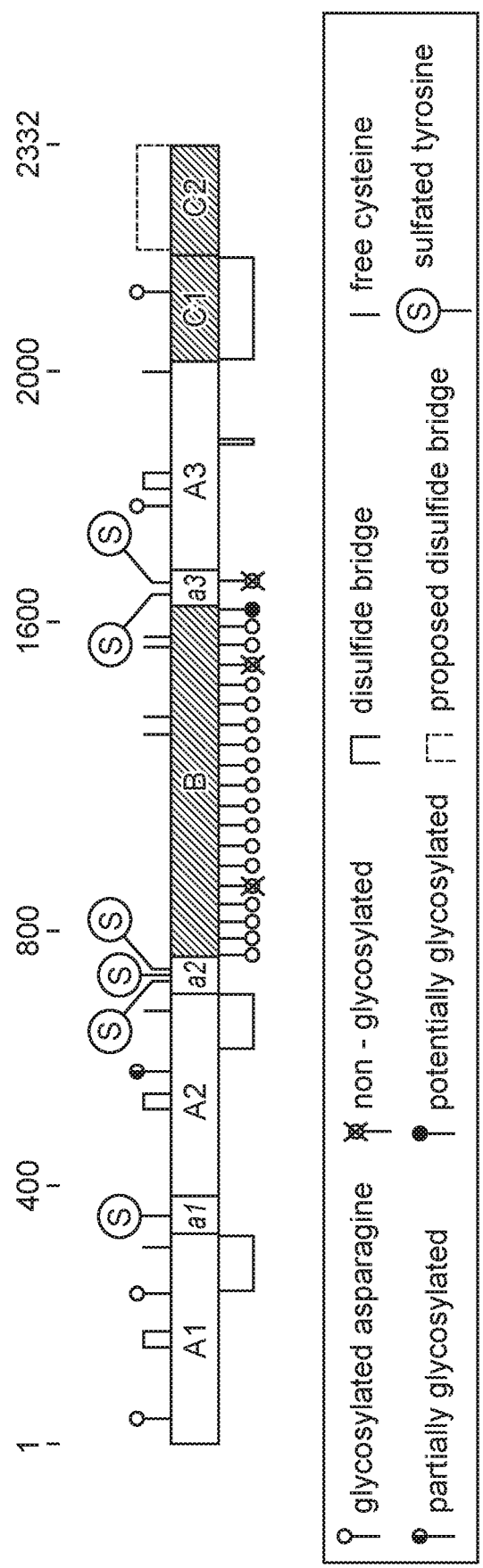
FIG. 2 shows the domains of human Factor VIII and location of cysteine residues (reproduced from Lenting et al. Blood 1998; 92:3983-3996)

The present invention provides high molecular weight (MW) polymers having hydrophilic groups or zwitterions, such as phosphorylcholine. Also provided in accordance with the present invention are methods and novel starting materials for making the high MW polymers. Also provided in accordance with the present invention are conjugates of the high MW polymers and functional agent (as defined herein). International Patent Application Nos. PCT/US2011/032768 and PCT/US2007/005372 are hereby incorporated by reference for all purposes.

II. Definitions

"Polymer" refers to a series of monomer groups linked together. The high MW polymers are prepared from monomers that include, but are not limited to, acrylates, methacrylates, acrylamides, methacrylamides, styrenes, vinyl-pyridine, vinyl-pyrrolidone and vinyl esters such as vinyl acetate. Additional monomers are useful in the high MW polymers of the present invention. When two different monomers are used, the two monomers are called "comonomers," meaning that the different monomers are copolymerized to form a single polymer. The polymer can be linear or branched. When the polymer is branched, each polymer chain is referred to as a "polymer arm." The end of the polymer arm linked to the initiator moiety is the proximal end, and the growing-chain end of the polymer arm is the distal end. On the growing chain-end of the polymer arm, the polymer arm end group can be the radical scavenger, or another group.

"Initiator" refers to a compound capable of initiating a polymerization using the monomers or comonomers of the present invention. The polymerization can be a conventional free radical polymerization or preferably a controlled"living" radical polymerization, such as Atom Transfer Radical Polymerization (ATRP), Reversible Addition-Fragmentation-Termination (RAFT) polymerization or nitroxide mediated polymerization (NMP). The polymerization can be a "pseudo" controlled polymerization, such as degenerative transfer. When the initiator is suitable for ATRP, it contains a labile bond which can be homolytically cleaved to form an initiator fragment, L being a radical capable of initiating a radical polymerization, and a radical scavenger, I', which reacts with the radical of the growing polymer chain to reversibly terminate the polymerization. The radical scavenger I' is typically a halogen, but can also be an organic moiety, such as a nitrile.

"Linker" refers to a chemical moiety that links two groups together. The linker can be cleavable or non-cleavable. Cleavable linkers can be hydrolyzable, enzymatically cleavable, pH sensitive, photolabile, or disulfide linkers, among others. Other linkers include homobifunctional and heterobifunctional linkers. A "linking group" is a functional group capable of forming a covalent linkage consisting of one or more bonds to a bioactive agent. Nonlimiting examples include those illustrated in Table 1.

The term "reactive group" as used herein refers to a group that is capable of reacting with another chemical group to form a covalent bond, i.e. is covalently reactive under suitable reaction conditions, and generally represents a point of attachment for another substance. The reactive group is a moiety, such as maleimide or succinimidyl ester, on the compounds of the present invention that is capable of chemically reacting with a functional group on a different compound to form a covalent linkage. Reactive groups generally include nucleophiles, electrophiles and photoactivatable groups.

"Functional agent" is defined to include a bioactive agent or a diagnostic agent. A "bioactive agent" is defined to include any agent, drug, compound, or mixture thereof that targets a specific biological location (targeting agent) and/or provides some local or systemic physiological or pharmacologic effect that can be demonstrated in vivo or in vitro. Non-limiting examples include drugs, vaccines, antibodies, antibody fragments, scFvs, diabodies, avimers, vitamins and cofactors, polysaccharides, carbohydrates, steroids, lipids, fats, proteins, peptides, polypeptides, nucleotides, oligonucleotides, polynucleotides, and nucleic acids (e.g., mRNA, tRNA, snRNA, RNAi, DNA, cDNA, antisense constructs, ribozymes, etc). A "diagnostic agent" is defined to include any agent that enables the detection or imaging of a tissue or disease. Examples of diagnostic agents include, but are not limited to, radiolabels, fluorophores and dyes.

"Therapeutic protein" refers to peptides or proteins that include an amino acid sequence which in whole or in part makes up a drug and can be used in human or animal pharmaceutical applications. Numerous therapeutic proteins are known including, without limitation, those disclosed herein.

"Phosphorylcholine," also denoted as "PC," refers to the following:

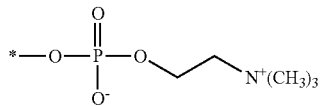

where * denotes the point of attachment. The phosphorylcholine is a zwitterionic group and includes salts (such as inner salts), and protonated and deprotonated forms thereof.

"Phosphorylcholine containing polymer" is a polymer that contains phosphorylcholine. "Zwitterion containing polymer" refers to a polymer that contains a zwitterion.

Poly(acryloyloxyethyl phosphorylcholine) containing polymer refers to a polymer containing 2-(acryloyloxy)ethyl-2-(trimethylammonium)ethyl phosphate as monomer.

Poly(methacryloyloxyethyl phosphorylcholine) containing polymer refers to a polymer containing 2-(methacryloyloxy)ethyl-2-(trimethylammonium)ethyl phosphate as monomer.

"Molecular weight" in the context of the polymer can be expressed as either a number average molecular weight, or a weight average molecular weight or a peak molecular weight. Unless otherwise indicated, all references to molecular weight herein refer to the peak molecular weight. These molecular weight determinations, number average (Mn), weight average (Mw) and peak (Mp), can be measured using size exclusion chromatography or other liquid chromatography techniques. Other methods for measuring molecular weight values can also be used, such as the use of end-group analysis or the measurement of colligative properties (e.g., freezing-point depression, boiling-point elevation, or osmotic pressure) to determine number average molecular weight, or the use of light scattering techniques, ultracentrifugation or viscometry to determine weight average molecular weight. In a preferred embodiment of the present invention, the molecular weight is measured by SEC-MALS (size exclusion chromatography—multi angle light scattering). The polymeric reagents of the invention are typically polydisperse (i.e., number average molecular weight and weight average molecular weight of the polymers are not equal), preferably possessing low polydispersity values of, for example, less than about 1.5, as judged by gel permeation chromatography. In other embodiments, the polydispersities (PDI) are more preferably in the range of about 1.4 to about 1.2, still more preferably less than about 1.15, and still more preferably less than about 1.10, yet still more preferably less than about 1.05, and most preferably less than about 1.03.

The phrase "a" or "an" entity as used herein refers to one or more of that entity; for example, a compound refers to one or more compounds or at least one compound. As such, the terms "a" (or "an"), "one or more", and "at least one" can be used interchangeably herein.

"About" as used herein means variation one might see in measurements taken among different instruments, samples, and sample preparations.

"Protected," "protected form," "protecting group" and "protective group" refer to the presence of a group (i.e., the protecting group) that prevents or blocks reaction of a particular chemically reactive functional group in a molecule under certain reaction conditions. Protecting groups vary depending upon the type of chemically reactive group being protected as well as the reaction conditions to be employed and the presence of additional reactive or protecting groups in the molecule, if any. Suitable protecting groups include those such as found in the treatise by Greene et al., "Protective Groups In Organic Synthesis," $3^{rd}$ Edition, John Wiley and Sons, Inc., New York, 1999.

"Alkyl" refers to a straight or branched, saturated, aliphatic radical having the number of carbon atoms indicated. For example, $C_1$-$C_6$ alkyl includes, but is not limited to, methyl, ethyl, propyl, isopropyl, butyl, isobutyl, sec-butyl, tert-butyl, pentyl, isopentyl, hexyl, etc. Other alkyl groups include, but are not limited to heptyl, octyl, nonyl, decyl, etc. Alkyl can include any number of carbons, such as 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 and 5-6. The alkyl group is typically monovalent, but can be divalent, such as when the alkyl group links two moieties together.

The term "lower" referred to above and hereinafter in connection with organic radicals or compounds respectively defines a compound or radical which can be branched or unbranched with up to and including 7, preferably up to and including 4 and (as unbranched) one or two carbon atoms.

"Alkylene" refers to an alkyl group, as defined above, linking at least two other groups, i.e., a divalent hydrocarbon radical. The two moieties linked to the alkylene can be linked to the same atom or different atoms of the alkylene. For instance, a straight chain alkylene can be the bivalent radical of —$(CH_2)_n$—, where n is 1, 2, 3, 4, 5 or 6. Alkylene groups include, but are not limited to, methylene, ethylene, propylene, isopropylene, butylene, isobutylene, sec-butylene, pentylene and hexylene.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR' C(NH$_2$)=NH, —NH—C(NH$_2$)=NR', —S(O)R', —S(O)$_2$R', —S(O)$_2$NR'R", —CN and —NO$_2$ in a number ranging from zero to (2m'+1), where m' is the total number of carbon atoms in such radical. R', R" and R'" each independently refer to hydrogen, unsubstituted ($C_1$-$C_8$)alkyl and heteroalkyl, unsubstituted aryl, aryl substituted with 1-3 halogens, unsubstituted alkyl, alkoxy or thioalkoxy groups, or aryl-($C_1$-$C_4$)alkyl groups. When R' and R" are attached to the same nitrogen atom, they can be combined with the nitrogen atom to form a 5-, 6-, or 7-membered ring. For example, —NR'R" is meant to include I-pyrrolidinyl and 4-morpholinyl. From the above discussion of substituents, one of skill in the art will understand that the term "alkyl" is meant to include groups such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like). Preferably, the substituted alkyl and heteroalkyl groups have from 1 to 4 substituents, more preferably 1, 2 or 3 substituents. Exceptions are those perhalo alkyl groups (e.g., pentafluoroethyl and the like) which are also preferred and contemplated by the present invention.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

"Alkoxy" refers to alkyl group having an oxygen atom that either connects the alkoxy group to the point of attachment or is linked to two carbons of the alkoxy group. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. For example, the alkoxy groups can be substituted with halogens to form a "halo-alkoxy" group.

"Carboxyalkyl" means an alkyl group (as defined herein) substituted with a carboxy group. The term "carboxycycloalkyl" means an cycloalkyl group (as defined herein) substituted with a carboxy group. The term alkoxyalkyl means an alkyl group (as defined herein) substituted with an alkoxy group. The term "carboxy" employed herein refers to carboxylic acids and their esters.

"Haloalkyl" refers to alkyl as defined above where some or all of the hydrogen atoms are substituted with halogen atoms. Halogen (halo) preferably represents chloro or fluoro, but may also be bromo or iodo. For example, haloalkyl includes trifluoromethyl, fluoromethyl, 1,2,3,4,5-pentafluoro-phenyl, etc. The term "perfluoro" defines a compound or radical which has all available hydrogens replaced with fluorine. For example, perfluorophenyl refers to 1,2,3,4,5-pentafluorophenyl, perfluoromethyl refers to 1,1,1-trifluoromethyl, and perfluoromethoxy refers to 1,1,1-trifluoromethoxy.

"Fluoro-substituted alkyl" refers to an alkyl group where one, some, or all hydrogen atoms have been replaced by fluorine.

"Cytokine" in the context of this invention is a member of a group of protein signaling molecules that may participate in cell-cell communication in immune and inflammatory responses. Cytokines are typically small, water-soluble glycoproteins that have a mass of about 8-35 kDa.

"Cycloalkyl" refers to a cyclic hydrocarbon group that contains from about 3 to 12, from 3 to 10, or from 3 to 7 endocyclic carbon atoms. Cycloalkyl groups include fused, bridged and spiro ring structures.

"Endocyclic" refers to an atom or group of atoms which comprise part of a cyclic ring structure.

"Exocyclic" refers to an atom or group of atoms which are attached but do not define the cyclic ring structure.

"Cyclic alkyl ether" refers to a 4 or 5 member cyclic alkyl group having 3 or 4 endocyclic carbon atoms and 1 endocyclic oxygen or sulfur atom (e.g., oxetane, thietane, tetrahydrofuran, tetrahydrothiophene); or a 6 to 7 member cyclic alkyl group having 1 or 2 endocyclic oxygen or sulfur atoms (e.g., tetrahydropyran, 1,3-dioxane, 1,4-dioxane, tetrahydrothiopyran, 1,3-dithiane, 1,4-dithiane, 1,4-oxathiane).

"Alkenyl" refers to either a straight chain or branched hydrocarbon of 2 to 6 carbon atoms, having at least one double bond. Examples of alkenyl groups include, but are not limited to, vinyl, propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can also have from 2 to 3, 2 to 4, 2 to 5, 3 to 4, 3 to 5, 3 to 6, 4 to 5, 4 to 6 and 5 to 6 carbons. The alkenyl group is typically monovalent, but can be divalent, such as when the alkenyl group links two moieties together.

"Alkenylene" refers to an alkenyl group, as defined above, linking at least two other groups, i.e., a divalent hydrocarbon radical. The two moieties linked to the alkenylene can be linked to the same atom or different atoms of the alkenylene. Alkenylene groups include, but are not limited to, ethenylene, propenylene, isopropenylene, butenylene, isobutenylene, sec-butenylene, pentenylene and hexenylene.

"Alkynyl" refers to either a straight chain or branched hydrocarbon of 2 to 6 carbon atoms, having at least one triple bond. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can also have from 2 to 3, 2 to 4, 2 to 5, 3 to 4, 3 to 5, 3 to 6, 4 to 5, 4 to 6 and 5 to 6 carbons. The alkynyl group is typically monovalent, but can be divalent, such as when the alkynyl group links two moieties together.

"Alkynylene" refers to an alkynyl group, as defined above, linking at least two other groups, i.e., a divalent hydrocarbon radical. The two moieties linked to the alkynylene can be linked to the same atom or different atoms of the alkynylene. Alkynylene groups include, but are not limited to, ethynylene, propynylene, butynylene, sec-butynylene, pentynylene and hexynylene.

"Cycloalkyl" refers to a saturated or partially unsaturated, monocyclic, fused bicyclic or bridged polycyclic ring assembly containing from 3 to 12 ring atoms, or the number of atoms indicated. Monocyclic rings include, for example, cyclopropyl, cyclobutyl, cyclopentyl, cyclohexyl, and cyclooctyl. Bicyclic and polycyclic rings include, for example, norborane, decahydronaphthalene and adamantane. For example, $C_{3-8}$cycloalkyl includes cyclopropyl, cyclobutyl, cyclopentyl, cyclohexyl, cyclooctyl, and norbornane.

"Cycloalkylene" refers to a cycloalkyl group, as defined above, linking at least two other groups, i.e., a divalent hydrocarbon radical. The two moieties linked to the cycloalkylene can be linked to the same atom or different atoms of the cycloalkylene. Cycloalkylene groups include, but are not limited to, cyclopropylene, cyclobutylene, cyclopentylene, cyclohexylene, and cyclooctylene.

"Heterocycloalkyl" refers to a ring system having from 3 ring members to about 20 ring members and from 1 to about 5 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heterocycle includes, but is not limited to, tetrahydrofuranyl, tetrahydrothiophenyl, morpholino, pyrrolidinyl, pyrrolinyl, imidazolidinyl, imidazolinyl, pyrazolidinyl, pyrazolinyl, piperazinyl, piperidinyl, indolinyl, quinuclidinyl and 1,4-dioxa-8-aza-spiro[4.5]dec-8-yl.

"Heterocycloalkylene" refers to a heterocycloalkyl group, as defined above, linking at least two other groups. The two moieties linked to the heterocycloalkylene can be linked to the same atom or different atoms of the heterocycloalkylene.

"Aryl" refers to a monocyclic or fused bicyclic, tricyclic or greater, aromatic ring assembly containing 6 to 16 ring carbon atoms. For example, aryl may be phenyl, benzyl or naphthyl, preferably phenyl. "Arylene" means a divalent radical derived from an aryl group. Aryl groups can be mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkylene-phenyl is 2,3-dihydrobenzofuran-5-yl.

Preferred as aryl is naphthyl, phenyl or phenyl mono- or disubstituted by alkoxy, phenyl, halogen, alkyl or trifluoromethyl, especially phenyl or phenyl-mono- or disubstituted by alkoxy, halogen or trifluoromethyl, and in particular phenyl.

Examples of substituted phenyl groups as R are, e.g. 4-chlorophen-1-yl, 3,4-dichlorophen-1-yl, 4-methoxyphen-1-yl, 4-methylphen-1-yl, 4-aminomethylphen-1-yl, 4-methoxyethylaminomethylphen-1-yl, 4-hydroxyethylaminomethylphen-1-yl, 4-hydroxyethyl-(methyl)-aminomethylphen-1-yl, 3-aminomethylphen-1-yl, 4-N-acetylaminomethylphen-1-yl, 4-aminophen-1-yl, 3-aminophen-1-yl, 2-aminophen-1-yl, 4-phenyl-phen-1-yl, 4-(imidazol-1-yl)-phenyl, 4-(imidazol-1-ylmethyl)-phen-1-yl, 4-(morpholin-1-yl)-phen-1-yl, 4-(morpholin-1-ylmethyl)-phen-1-yl, 4-(2-methoxyethylaminomethyl)-phen-1-yl and 4-(pyrrolidin-1-ylmethyl)-phen-1-yl, 4-(thiophenyl)-phen-1-yl, 4-(3-thiophenyl)-phen-1-yl, 4-(4-methylpiperazin-1-yl)-phen-1-yl, and 4-(piperidinyl)-phenyl and 4-(pyridinyl)-phenyl optionally substituted in the heterocyclic ring.

"Arylene" refers to an aryl group, as defined above, linking at least two other groups. The two moieties linked to the arylene are linked to different atoms of the arylene. Arylene groups include, but are not limited to, phenylene.

"Arylene-oxy" refers to an arylene group, as defined above, where one of the moieties linked to the arylene is linked through an oxygen atom. Arylene-oxy groups include, but are not limited to, phenylene-oxy.

Similarly, substituents for the aryl and heteroaryl groups are varied and are selected from: -halogen, —OR', —OC(O)R', —NR'R'', —SR', —R', —CN, —NO$_2$, —CO$_2$R', —CONR'R'', —C(O)R', —OC(O)NR'R'', —NR''C(O)R', —NR''C(O)$_2$R', , —NR'—C(O)NR''R''', —NH—C(NH$_2$)=NH, —NR'C(NH$_2$)=NH, —NH—C(NH$_2$)=NR', —S(O)R', —S(O)$_2$R', —S(O)$_2$NR'R'', —N$_3$, —CH(Ph)$_2$, perfluoro($C_1$-$C_4$)alkoxy, and perfluoro($C_1$-$C_4$)alkyl, in a number ranging from zero to the total number of open valences on the aromatic ring system; and where R', R'' and R''' are independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted ($C_1$-$C_6$)alkyl.

"Heteroaryl" refers to a monocyclic or fused bicyclic or tricyclic aromatic ring assembly containing 5 to 16 ring atoms, where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Pyridyl represents 2-, 3- or 4-pyridyl, advantageously 2- or 3-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, and most preferred, 4-thiazolyl. Triazolyl is preferably 1-, 2- or 5-(1,2,4-triazolyl). Tetrazolyl is preferably 5-tetrazolyl.

Preferably, heteroaryl is pyridyl, indolyl, quinolinyl, pyrrolyl, thiazolyl, isoxazolyl, triazolyl, tetrazolyl, pyrazolyl, imidazolyl, thienyl, furanyl, benzothiazolyl, benzofuranyl, isoquinolinyl, benzothienyl, oxazolyl, indazolyl, or any of the radicals substituted, especially mono- or di-substituted.

As used herein, the term "heteroalkyl" refers to an alkyl group having from 1 to 3 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heteroalkyl can include ethers, thioethers, alkyl-amines and alkyl-thiols.

As used herein, the term "heteroalkylene" refers to a heteroalkyl group, as defined above, linking at least two other groups. The two moieties linked to the heteroalkylene can be linked to the same atom or different atoms of the heteroalkylene.

"Electrophile" refers to an ion or atom or collection of atoms, which may be ionic, having an electrophilic center, i.e., a center that is electron seeking, capable of reacting with a nucleophile. An electrophile (or electrophilic reagent) is a reagent that forms a bond to its reaction partner (the nucleophile) by accepting both bonding electrons from that reaction partner.

"Nucleophile" refers to an ion or atom or collection of atoms, which may be ionic, having a nucleophilic center, i.e., a center that is seeking an electrophilic center or capable of reacting with an electrophile. A nucleophile (or nucleophilic reagent) is a reagent that forms a bond to its reaction partner (the electrophile) by donating both bonding electrons. A "nucleophilic group" refers to a nucleophile after it has reacted with a reactive group. Non limiting examples include amino, hydroxyl, alkoxy, haloalkoxy and the like.

"Maleimido" refers to a pyrrole-2,5-dione-1-yl group having the structure:

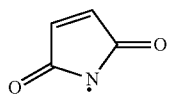

which upon reaction with a sulfhydryl (e.g., a thio alkyl) forms an —S-maleimido group having the structure

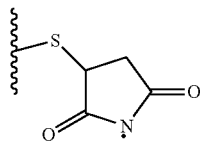

where "•" indicates the point of attachment for the maleimido group and "⸸" indicates the point of attachment of the sulfur atom the thiol to the remainder of the original sulfhydryl bearing group.

For the purpose of this disclosure, "naturally occurring amino acids" found in proteins and polypeptides are L-alanine, L-arginine, L-asparagine, L-aspartic acid, L-cysteine, L-glutamine, L-glutamic acid, L-glycine, L-histidine, L-isoleucine, L-leucine, L-lysine, L-methionine, L-phenylalanine, L-proline, L-serine, L-threonine, L-tryptophan, L-tyrosine, and or L-valine. "Non-naturally occurring amino acids" found in proteins are any amino acid other than those recited as naturally occurring amino acids. Non-naturally occurring amino acids include, without limitation, the D isomers of the naturally occurring amino acids, and mixtures of D and L isomers of the naturally occurring amino acids. Other amino acids, such as 4-hydroxyproline, desmosine, isodesmosine, 5-hydroxylysine, epsilon-N-methyllysine, 3-methylhistidine, although found in naturally occurring proteins, are considered to be non-naturally occurring amino acids found in proteins for the purpose of this disclosure as they are generally introduced by means other than ribosomal translation of mRNA.

"Linear" in reference to the geometry, architecture or overall structure of a polymer, refers to polymer having a single polymer arm.

"Branched," in reference to the geometry, architecture or overall structure of a polymer, refers to a polymer having 2 or more polymer "arms" extending from a core structure contained within an initiator. The initiator may be employed in an atom transfer radical polymerization (ATRP) reaction. A branched polymer may possess 2 polymer chains (arms), 3 polymer arms, 4 polymer arms, 5 polymer arms, 6 polymer arms, 7 polymer arms, 8 polymer arms, 9 polymer arms or more. Each polymer arm extends from a polymer initiation site. Each polymer initiation site is capable of being a site for the growth of a polymer chain by the addition of monomers. For example and not by way of limitation, using ATRP, the site of polymer initiation on an initiator is typically an organic halide undergoing a reversible redox process catalyzed by a transition metal compound such as cuprous halide. Preferably, the halide is a bromine.

"Pharmaceutically acceptable" composition or "pharmaceutical composition" refers to a composition comprising a compound of the invention and a pharmaceutically acceptable excipient or pharmaceutically acceptable excipients.

"Pharmaceutically acceptable excipient" and "pharmaceutically acceptable carrier" refer to an excipient that can be included in the compositions of the invention and that causes no significant adverse toxicological effect on the patient and is approved or approvable by the FDA for therapeutic use, particularly in humans. Non-limiting examples of pharmaceutically acceptable excipients include water, NaCl, normal saline solutions, lactated Ringer's, normal sucrose, normal glucose and the like.

"Patient" or "subject in need thereof" refers to a living organism suffering from or prone to a condition that can be prevented or treated by administration of a pharmaceutical composition as provided herein. Non-limiting examples include humans, other mammals and other non-mammalian animals.

Conjugates are preferably provided in isolated form. Isolated means that an object species has been at least partially separated from contaminants with which it is naturally associated or which are used in its manufacture but does not necessarily exclude the presence of other components intended to act in combination with an isolated species, such as a pharmaceutical excipient. Preferably a conjugate is the predominant macromolecular species present in a sample (i.e., on a molar basis in a composition and typically comprises at least about 50 percent (on a molar basis) of all macromolecular species present. Generally, an isolated conjugate comprises more than 80, 90, 95 or 99 percent of all macromolecular species present in a composition. Most preferably, a conjugate is purified to essential homogeneity (i.e., contaminant species cannot be detected in a composition by conventional detection methods), such that the composition consists essentially of a single macromolecular species. Conjugates have the same heavy and light chains are considered to be the same species notwithstanding there may be variation in glycosylation on protein moieties and variation in numbers of monomers in polymer moieties linked to different molecules of the conjugate.

"Therapeutically effective amount" refers to an amount of a conjugated functional agent or of a pharmaceutical composition useful for treating, ameliorating, or preventing an identified disease or condition, or for exhibiting a detectable therapeutic or inhibitory effect. The effect can be detected in an individual patient relative to a baseline measurement before treatment or by determining a statistically significant difference in outcome between treated and control populations.

The "biological half-life" of a substance is a pharmacokinetic parameter which specifies the time required for one half of the substance to be removed from an organism following introduction of the substance into the organism.

Sequence identity can be determined by aligning sequences using algorithms, such as BESTFIT, FASTA, and TFASTA in the Wisconsin Genetics Software Package Release 7.0, Genetics Computer Group, 575 Science Dr., Madison, Wis., using default gap parameters, or by inspection, and the best alignment (i.e., resulting in the highest percentage of sequence similarity over a comparison window). Percentage of sequence identity is calculated by comparing two optimally aligned sequences over a window of comparison, determining the number of positions at which the identical residues occurs in both sequences to yield the number of matched positions, dividing the number of matched positions by the total number of positions in the window of comparison (i.e., the window size), and multiplying the result by 100 to yield the percentage of sequence identity.

III. Factor VIII

Coagulation factor VIII (FVIII) circulates in plasma at a very low concentration and is bound non-covalently to von Willebrand factor (VWF). During hemostasis, FVIII is separated from VWF and acts as a cofactor for activated factor IX (FIXa)-mediated factor X (FX) activation by enhancing the rate of activation in the presence of calcium and phospholipids or cellular membranes.

FVIII is synthesized as a single-chain precursor of approximately 270-330 kDa with the domain structure A1-A2-B-A3-C1-C2 (FIG. 2). When purified from plasma (e.g., "plasma-derived" or "plasmatic"), FVIII is composed of a heavy chain (A1-A2-B) and a light chain (A3-C1-C2). The molecular mass of the light chain is 80 kDa whereas, due to proteolysis within the B domain, the heavy chain is in the range of 90-220 kDa. The domains are delineated as follows in SEQ ID NO:1 A1, residues Ala 1-Arg 372; A2, residues Ser 373-Arg 740; B, residues Ser 741-Arg 1648; A3, residues Ser 1690-Ile 2032; C1, residues Arg 2033-Asn 2172; and C2, residues Ser 2173-Tyr 2332. The remaining sequence, residues Glu 1649-Arg 1689, is usually referred to as the factor VIII light chain activation peptide. Factor VIII is proteolytically activated by thrombin or factor Xa, which dissociates it from von Willebrand's factor, forming factor VIIIa, which has procoagulant function. The biological function of factor VIIIa is to increase the catalytic efficiency of factor IXa toward factor X activation by several orders of magnitude. Thrombin-activated factor VIIIa is a 160 kDa A1/A2/A3-C1-C2.

Mature Factor VIII is heavily glycosylated and proteolyzed and circulates as a hetero-dimer having a heavy chain and a light chain connected by metal ions. The heavy chains consists of sequence related regions A1 and A2 domains and a connecting B region, which is heavily glycosylated. The light chain consists of A3, C1 and C2 domains. In plasma, Factor VIII circulates as a non-covalent complex with Von Willebrand's factor. It has been found that the B domain is unnecessary for Factor VIII coagulation activity.

Various in vitro assays have been devised to determine the potential efficacy of recombinant FVIII (rFVIII) as a therapeutic medicine. These assays mimic the in vivo effects of endogenous FVIII. In vitro thrombin treatment of FVIII results in a rapid increase and subsequent decrease in its procoagulant activity, as measured by in vitro assay. This activation and inactivation coincides with specific limited proteolysis both in the heavy and the light chains, which alter the availability of different binding epitopes in FVIII, e.g. allowing FVIII to dissociate from VWF and bind to a phospholipid surface or altering the binding ability to certain monoclonal antibodies.

The production of recombinant Factor VIII by recombinant engineering techniques has been described. See, e.g., U.S. Pat. Nos. 4,757,006, 5,733,873, 5,198,349, 5,250,421, 5,919,766 and European Patent No. 306 968. The gene for Factor VIII is located on the tip of the long arm of the X chromosome. The human Factor VII gene comprises 26 exons spread out over 186,000 bp of genomic DNA and codes for a protein of 2351 amino acids, including a 19 amino acid leader sequence. Factor VIII is one of the largest known genes. The mature Factor VIII protein is 2332 amino acids (Swiss Prot P00451). The protein sequence of Factor VIII is set forth in FIG. 1. FVIII is considered to be recombinant if synthesized as a result of genetic techniques as distinct from being isolated from a natural source, such as human plasma. Recombinant FVIII may or may not be changed in other respects from plasma derived FVIII (e.g., by truncation, or mutation).

FVIII is subject to numerous known polymorphisms described in the Swiss Prot database. Thus, for example, the aspartic acid residue at position 56 may optionally be valine in accordance with the present invention. Similarly, the aspartic acid at position 1141 may also be glutamic acid in accordance with the present invention. All known or discovered allelic and polymorphic variations of FVIII are included within the scope of the present invention.

Herein, the term "Factor VIII" or "FVIII" refers to any FVIII molecule which exhibits biological activity, particularly promotion of blood clotting, that is associated with native FVIII. Several assays for FVIII activity are commercially available (see Chandler et al., Am J Clin Pathol 2003; 120:34-39). In a preferred embodiment of the present invention, the FVIII has at least a portion or all of the B domain (e.g., at least 100, 200, 500 or 900 residues including at least one cysteine conjugatable to a polymer). Preferably the portion includes the two most C-terminal cysteines from the intact B-domain (at positions 1604 and 1636). In one embodiment of the invention, the FVIII molecule is full-length Factor VIII (except the signal peptide can be deleted). The FVIII molecule is a protein which is encoded for by DNA sequences capable of hybridizing to DNA encoding Factor VIII:C under stringent conditions (e.g., 52° C., 50% formamide, 5×SSC). Such a protein may contain amino acid deletions at various sites between or within the domains A1-A2-B-A3-C1-C2 (see, e.g., U.S. Pat. No. 4,868,112). The FVIII molecule may also be an analog of native FVIII wherein one or more amino acid residues have been replaced by site-directed mutagenesis.

The FVIII molecules useful for the present invention include the full-length protein, precursors of the protein, biologically active or functional subunits or fragments of the protein, and functional derivatives thereof, as well as variants thereof as described herein below. Reference to FVIII is meant to include all potential forms of such proteins and including forms of FVIII having at least a portion or all of the native B domain sequence intact and forms in which the B domain is absent.

In another aspect of the present invention, FVIII moieties having various deletions may also be conjugated to the polymers of the present invention. The Factor VIII molecules according to this aspect of the present invention are B domain truncated Factor FVIII wherein the remaining domains have the sequence as set forth in amino acid no 1-740 and 1649-2332 in SEQ ID NO. 1. Factor VIII molecules according to the invention are preferably recombinant molecules produced in transformed host cells, preferably of mammalian origin.

However, the remaining domains (i.e. the three A-domains and the two C-domains) may differ slightly e.g. about 1%, 2%, 3%, 4% or 5% from the amino acid sequence as set forth in SEQ ID NO 1 (amino acids 1-740 and 1649-2332). In particular, amino acid modifications (substitutions, deletions, or insertions) can be introduced in the remaining domains, e.g. in order to modify the binding capacity of Factor VIII with various other components such as e.g. vW factor, LPR, various receptors, other coagulation factors, cell surfaces, etc. Furthermore, the Factor VIII molecules according to the invention can comprise other post-translational modifications in e.g. the truncated B-domain and/or in one or more of the other domains of the molecules. These other post-translational modifications may be in the form of various molecules conjugated to the Factor VIII molecule according to the invention such as e.g. polymeric compounds, peptidic compounds, fatty acid derived compounds, and so forth.

Factor VIII molecules according to the present invention, regardless of whether they are modified outside the B domain or not, have other posttranslational modifications or not, all have Factor VIII activity, meaning the ability to function in the coagulation cascade in a manner functionally similar or equivalent to FVIII, induce the formation of FXa via interaction with FIXa on an activated platelet, and support the formation of a blood clot. The activity can be assessed in vitro by techniques well known in the art (e.g., Chandler et al., supra) such as e.g. clot analysis, endogenous thrombin potential analysis, etc. Factor VIII molecules according to the present invention have FVIII activity being at least about 10%, at least 20%, at least 30%, at least 40%, at least 50%, at least 60%, at least 70%, at least 80%, at least 90%, and 100% or even more than 100% of that of native human FVIII.

The B-domain in Factor VIII spans amino acids 741-1648 in SEQ ID NO 1. The B-domain is cleaved at several different sites, generating large heterogeneity in circulating plasma FVIII molecules. The exact function of the heavily glycosylated B-domain is unknown. But the domain is dispensable for FVIII activity in the coagulation cascade. This apparent lack of function is supported by the fact that B domain deleted/truncated FVIII appears to have in vive properties identical to those seen for full length native FVIII. That being said there are indications that the B-domain may reduce the association with the cell membrane, at least under serum free conditions.

B domain truncated/deleted Factor VIII molecule: Endogenous full length FVIII is synthesized as a single-chain precursor molecule. Prior to secretion, the precursor is cleaved into the heavy chain and the light chain. Recombinant B domain-deleted FVIII can be produced from two different strategies. Either the heavy chain without the B-domain and the light chain are synthesized individually as two different polypeptide chains (two-chain strategy) or the B-domain deleted FVIII is synthesized as a single precursor polypeptide chain (single-chain strategy) that is cleaved into the heavy and light chains in the same way as the full-length FVIII precursor.

In a B domain-deleted FVIII precursor polypeptide, the heavy and light chain moieties are normally separated by a linker. To minimize the risk of introducing immunogenic epitopes in the B domain-deleted FVIII, the sequence of the linker is preferably derived from the FVIII B-domain. The linker must comprise a recognition site for the protease that separates the B domain-deleted FVIII precursor polypeptide into the heavy and light chain. In the B domain of full length FVIII, amino acids 1644-1648 constitute this recognition site. The thrombin site leading to removal of the linker on activation of B domain-deleted FVIII is located in the heavy chain. Thus, the size and amino acid sequence of the linker is unlikely to influence its removal from the remaining FVIII molecule by thrombin activation. Deletion of the B domain is an advantage for production of FVIII. Nevertheless, parts of the B domain can be included in the linker without reducing the productivity. The negative effect of the B domain on productivity has not been attributed to any specific size or sequence of the B domain.

According to the present invention, the term "recombinant Factor VIII" (rFVIII) may include any FVIII, heterologous or naturally occurring, obtained via recombinant DNA technology, or a biologically active derivative thereof. In certain embodiments, the term encompasses proteins as described above and nucleic acids, encoding a rFVIII of the invention. Such nucleic acids include, for example and without limitation, genes, pre-mRNAs, mRNAs, polymorphic variants, alleles, synthetic and naturally-occurring mutants. Proteins embraced by the term rFVIII include, for example and without limitation, those proteins and polypeptides described hereinabove, proteins encoded by a nucleic acid described above, interspecies homologs and other polypeptides that have an amino acid sequence that has greater than about 85%, about 90%, about 91%, about 92%, about 93%, about 94%, about 95%, about 96%, about 97%, about 98% or about 99% or greater amino acid sequence identity, over a region of at least about 100, about 200, about 300, about 400, or more amino, to a polypeptide encoded by a referenced nucleic acid or an amino acid sequence described herein. Preferably, Factor VIII shows at least 90, 95, 96, 97, 98 or 99% sequence identity to the entire sequence of A1, A2, A3, C1, and C2 domains.

In accordance with certain aspects of the present invention, production of rFVIII includes any method known in the art for (i) the production of recombinant DNA by genetic engineering, (ii) introducing recombinant DNA into prokaryotic or eukaryotic cells by, for example and without limitation, transfection, electroporation or microinjection, (iii) cultivating said transformed cells, (iv) expressing rFVIII, e.g. constitutively or upon induction, and (v) isolating said rFVIII, e.g. from the culture medium or by harvesting the transformed cells, in order to (vi) obtain purified rFVIII.

In preferred aspects of the present invention, the rFVIII is produced by expression in a suitable prokaryotic or eukaryotic host system characterized by producing a pharmacologically acceptable rFVIII molecule. Examples of eukaryotic cells are mammalian cells, such as CHO, COS, HEK 293, BHK, SK-Hip, and HepG2.

In still other aspects, a wide variety of vectors are used for the preparation of the rFVIII and are selected from eukaryotic and prokaryotic expression vectors. Examples of vectors for prokaryotic expression include plasmids such as, and without limitation, preset, pet, and pad, wherein the promoters used in prokaryotic expression vectors include one or more of, and without limitation, lac, trc, trp, recA, or araBAD. Examples of vectors for eukaryotic expression include: (i) for expression in yeast, vectors such as, and without limitation, pAO, pPIC, pYES, or pMET, using promoters such as, and without limitation, AOX1, GAP, GAL1, or AUG1; (ii) for expression in insect cells, vectors such as and without limitation, pMT, pAc5, pIB, pMIB, or pBAC, using promoters such as and without limitation PH, p10, MT, Ac5, OpIE2, gp64, or polh, and (iii) for expression in mammalian cells, vectors such as, and without limitation, pSVL, pCMV, pRc/RSV, pcDNA3, or pBPV, and vectors derived from, in one aspect, viral systems such as and without limitation vaccinia virus, adeno-associated viruses, herpes viruses, or retroviruses, using promoters such as and without limitation CMV, SV40, EF-1, UbC, RSV, ADV, BPV, and beta-actin.

FVIII molecules may be coupled to polymers of the instant invention as described herein for other functional agents, including proteins. For example, in one embodiment polymer is conjugated to FVIII via free amino groups of the protein using N-hydroxysuccinimide (NHS) esters. Reagents targeting conjugation to amine groups can randomly react to ϵ-amine group of lysines, α-amine group of N-terminal amino acids, and δ-amine group of histidines. Full length FVIII has 158 lysines, 2 N-termini, and 75 histidines. In accordance with an aspect of the present invention, conjugates can be formed using one or more of these sites. However, it is known that FVIII is required to interact with multiple partners such as von Willebrand Factor (VWF), coagulation factor X (FX), and activated factor IX (FIXa) for full activity. Conjugation of polymers to free amino groups, thus, might negatively impact the ability of the conjugated FVIII to affect clotting.

In another embodiment the polymers of the instant invention may be coupled to free SH groups using any appropriate thiol-reactive chemistry including, without limitation, maleimide chemistry, or the coupling of polymer hydrazides or polymer amines to carbohydrate moieties of the FVIII after prior oxidation. The use of maleimide coupling is a particularly preferred embodiment of the present invention.

In accordance with a preferred embodiment of the present invention, polymers may be coupled to any cysteine residue of FVIII using maleimide coupling as long as sufficient biological activity is retained. Alternatively, any suitable amine or carbohydrate moiety of FVIII may be used for coupling of the polymers of the instant invention to FVIII as long as sufficient activity is retained.

FVIII has 4 cysteines in the B domain and 19 cysteines in the other domains. Of the 19 cysteines in B domain-deleted (BDD) FVIII, 16 form disulfides and the other 3 are free cysteines. The structural model of BDD-FVIII suggests that all 3 free cysteines are buried and would not be accessible for reaction with a polymer (Baisan et al. 116 Blood 270-279 (2010)). Thus, in accordance with an aspect of the present invention, polymers are preferably covalently attached to cysteine residues introduced into FVIII by site directed mutagenesis (see Table 1, below for possible sites). See, e.g., EP 2363414A2.

TABLE 1

FVIII Cysteine Variants for
Zwitterionic Polymer Conjugation

| Cys Mutation | Domain |
|---|---|
| Y81C | A1 |
| F129C | A1 |
| K377C | A2 |
| H378C | A2 |
| K422C | A2 |
| Q468C | A2 |

TABLE 1-continued

FVIII Cysteine Variants for
Zwitterionic Polymer Conjugation

| Cys Mutation | Domain |
|---|---|
| L491C | A2 |
| L504C | A2 |
| K556C | A2 |
| K570C | A2 |
| D1795C | A3 |
| Q1796C | A3 |
| R1803C | A3 |
| K1804C | A3 |
| K1808C | A3 |
| K1810C | A3 |
| T1812C | A3 |
| K1813C | A3 |
| N1864C | A3 |
| T1911C | A3 |
| N2118C | C1 |
| Q2091C | C1 |
| Q2284C | C2 |

See, e.g, Mei, B., et al., (2012) Thrombosis and Hemostasis 116, 270-279.

According to another aspect of the present invention, polymers are preferably coupled to cysteine residues naturally occurring in the B domain. Alternatively, in accordance with an aspect of the present invention, cysteine residues may be added to the B domain via recombinant DNA technology. The polymer can be conjugated to the rFVIII via one and only one cysteine residue, or via multiple cysteines. Preferably the cysteine(s) are in the B domain, preferably either of the two most C-terminal cysteines in the B-domain at positions 1604 and 1636 of SEQ ID NO: 1. (f only a portion of the B-domain is used, the two most C-terminal cysteines are the C-terminal cysteines in the portion aligned with the two most C-terminal cysteines of the intact B-domain.) Attachment of a branched polymer via a single cysteine in any given molecule of rFVIII is advantageous for surrounding rFVIII with polymer and zwitterionic charge without substantial impairment if any of rFVIIII activity. The single cysteine via which the polymer is conjugated can be the same or different in different molecules of rFVIIII. Although an understanding of mechanism is not required for practice of the invention, it is believed that the zwitterionic charge on polymer surrounding rFVIII virtually immobilizes a layer of water molecules that consequently moves in tandem with rFVIII protecting it from degradative processes in vivo.

A preparation of rFVIII is typically homogenous due to proteoloytic processing at different sites within the B domain resulting in several bands from the heavy chain on a gel. Conjugation of such a preparation of rFVIII to a polymer of the invention resulting in polymerization via one of the two C-terminal cysteines forms conjugates only for molecules of rFVIII in which these two-terminal cysteines are present. Molecules of rFVIII in which the B domain is more truncated do not form conjugates to a significant extent. Specificity of conjugation to a single form of B-domain is shown by comparing the bands on a gel before and after conjugation and observing loss or substantial reduction of only one of the bands pre-conjugation. Conjugated rFVIII can easily be separated from unconjugated molecules of rFVIII due to the large difference in molecular weight. In consequence, a preparation of conjugated rFVIII can have much greater homogeneity than a typical preparation of rFVIII. For example, at least 80, 90, 95 or 99% of molecules in a preparation can have the same portion of the B-domain, for example, an intact B-domain and one and only one polymer (preferably branched) attached per molecule (although there may be glycosylation differences between different proteins and difference in length between different polymers). In some preparations, the portion is at least residues 1-1604 or 1-1636 or 1-1648 of SEQ ID NO:1. In some preparations, the portions consists of residues 1-1648 of SEQ ID NO:1.

The B-domain of a conjugate including the polymer linked to it may be excised after administration to a subject by the endogenous FVIII activation process. However, the conjugated polymer still fulfills a role of prolonging the half-life of the linked FVIII until a need for activity occurs. Moreover, loss of polymer in the course of activation has the advantage that FVIII can be more rapidly degraded (compared with FVIII conjugated other than via the B domain) after activation has occurred. For this reason, rFVIII conjugated via the B domain is advantageous for prophylaxis to subjects having hemophilia but not known to be experiencing bleeding (internal or external) at the time of administration. Conjugation to the polymer facilitates persistence of the conjugate until such time as the subject may be determined to be experiencing a bleeding episode.

At this time, the B-domain and associated polymer may be processed from the rFVIII, and the remaining rFVIII can facilitate clotting and thereafter be inactivated.

Conjugation of rFVIII to a polymer according to the present methods increases the in vivo half-life of rFVIII in humans above 11 hours. For example, the half-life can be 12-50 hours. Preferably, the half-life is 20 hours or longer. Half-lives are measured as means in a population of human subjects free of prior antibody response to human FVIII. Such human can have but need not have hemophilia for purposes of determining half-life.

Because of its longer half-life, the conjugate can be administered less frequently in prophylaxis than in current regimes, for example, administration at no more than weekly intervals. In some prophylactic regimes, the conjugate is administered at a frequency between weekly and monthly, for example, weekly, biweekly, or monthly. Despite the decreased frequency of administration, subjects receiving the conjugate can have increased trough levels of FVIII compared with current methods. In current methods, subjects on prophylactic regimes spend about 18 hour per week with trough levels of FVIII activity at a level below 1% of that of the mean level in control subjects without hemophilia. A level below 1%, places a subject at high risk of an acute bleed. With the present methods, subjects can be maintained with a trough level above 1%, 3% or even 5% of the mean level of FVIII activity in control subjects without hemophilia for a period of at least a week, a month, a year or indefinitely. Activity can be assessed in an in vitro chromogenic assay, which includes activation of FVIII by processing of the B domain.

In prophylactic treatment or other treatment, the conjugate of the invention is suitable for administration to subjects who have previously been treated with FVIII (not conjugated as described herein) and developed a human antibody response against it. The polymer moiety of the present conjugates shields the FVIII of the present conjugates from such antibodies allowing it to persist in the blood for longer than would be the case for unconjugated FVIII, and preferably with essentially the same half-life in a subject without antibodies to FVIII.

With regard to the naturally occurring cysteines in the B domain, an intact B domain is not essential for FVIII activity. The B domain of FVIII begins at amino acid 745 and continues to amino acid 1648. The B domain has 4 naturally occurring cysteine residues: 1293, 1373, 1604 and 1636. In accordance with the present invention, coupling at one or more of these residues is preferred. Coupling of the polymers of the present invention to residues 1604 and 1636 is particularly preferred.

In accordance with the present invention, conjugates of the high MW polymers of the present invention and FVIII are presented. In accordance with one aspect of the present invention, preferred conjugates are presented in which FVIII is coupled to a zwitterionic polymer wherein the polymer is composed of one or more monomer units and wherein at least one monomer unit has a zwitterionic group. Preferably, the zwitterionic group is phosphorylcholine.

In a preferred aspect of the present invention, one of the monomer units is 2-(acryloyloxyethyl)-2'-(trimethylammoniumethyl) phosphate or 2-(methacryloyloxyethyl)-2'-(trimethylammoniumethyl) phosphate (HEMA-PC). In other preferred embodiments, polymer is synthesized from a single monomer which is preferably 2-(acryloyloxyethyl)-2'-(trimethylammoniumethyl) phosphate or 2-(methacryloyloxyethyl)-2'-(trimethylammoniumethyl) phosphate.

In a preferred embodiment of the present invention, the FVIII or the conjugate is a recombinant FVIII (rFVIII). In preferred embodiments of the present invention, rFVIII is full length. In other preferred embodiments of the present invention, the rFVIII is purified from a mammalian host cell. In still another aspect of the present invention, the FVIII comprises a deletion of part or all of the B domain.

In still other aspects of the present invention, it is preferred that the FVIII conjugates have 2 or more preferably 3 or more polymer arms wherein the monomer is HEMA-PC. In another aspect of the present invention, it is preferred that the conjugates have 2, 3, 4, 5, 6, 7, 8, 9, 10, 11, or 12 polymer arms wherein the monomer is HEMA-PC. More preferably, the conjugates have 3, 6 or 9 arms. Most preferably, the conjugate has 9 arms.

In one aspect of the present invention, it is preferred that the polymer-FVIII conjugates have a polymer portion with a molecular weight of between 100,000 and 1,500,000 daltons. More preferably the conjugate has a polymer portion with a molecular weight between 500,000 and 1,000,000 daltons. Still more preferably the conjugate has a polymer portion with a molecular weight between 600,000 to 800,000 daltons. Most preferably the FVIII conjugate has a polymer portion with a molecular weight between 600,000 and 850,000 daltons and has 9 arms. Here and elsewhere in this application, the total molecular weight for polymer including the FVIII is in ranges about 300,000 daltons higher than those given for the polymer portion.

In accordance with an aspect of the present invention, methods are provided for synthesizing a zwitterionic polymer-functional agent conjugate, the conjugate having one or more functional agents and one or more polymer arms wherein each of the polymer arms has one or more monomer types wherein at least one of the types has a zwitterion. According to an aspect of the present invention, the method has the steps of a. combining an initiator comprising one or more polymer synthesis initiator moieties and a first reactive group with one or more monomer types suitable for polymerization wherein at least one of said monomer types comprises a zwitterion; wherein said monomer types react to form polymer(s) at the polymer synthesis initiator moity(ies) to provide a polymerized initiator;

b. coupling a linker moiety comprising second and third reactive groups to the polymerized initiator to provide a linker-polymerized initiator having an unreacted reactive group; and c. coupling one or more functional agents to the unreacted reactive group of the linker-polymerized initiator to provide the polymer-functional agent conjugate.

Prior to the instant invention, the initiator molecule or entity had to contain a deprotectable functional group that would allow coupling of the functional agent. An example of such an initiator having a protected maleimide is shown below:

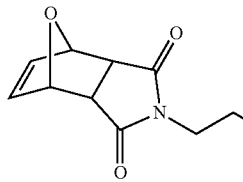
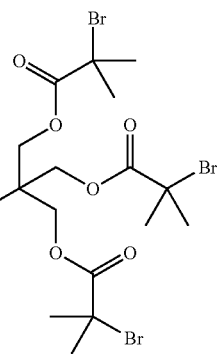

After polymer synthesis, the protected maleimide is deprotected with heat to allow for generation of maleimide which could be used to couple functional agent. If one wanted to vary the nature of the chemical entity in between the maleimide and the polymer initiation site, one would have to synthesize an entire new initiator.

Considering possible scale up of the polymer synthesis process, each time the initiator is changed or altered in any way, a new scaled up synthesis procedure has to be developed. Each change in the nature of the initiator molecule can have a wide range of effects on polymer synthesis. However, in accordance with the present invention, a single initiator moiety can be used for large scale polymer preparation. Thus, conditions can be developed for scaled up optimal polymer synthesis. Using the instantly claimed invention, such polymer can then be adapted to various types of functional agents by "snapping-on" various types of linkers.

For example, if it is desired to conjugate a larger functional agent to a polymer of the instant invention such as an antibody of even a Fab fragment, a longer linker sequence can be snapped on to the polymer. In contrast, smaller functional agents may call for relatively shorter linker sequences.

In preferred embodiments of the methods, the initiator has 1, 2, 3, 4, 5, 6, 7, 8, 9, 10, 11 or 12 sites for polymer initiation. Preferably, the initiator has 3, 6 or 9 sites for polymer initiation.

In accordance with this aspect of the present invention, polymer synthesis imitator moieties preferably have the following structure:

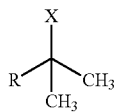

where X is a NCS or a halogen which allows initiation of ATRP or related polymer synthesis schemes and R is the rest of the imitator.

In accordance with the present invention, the initiator preferably has the structure:

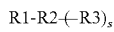

wherein R1 has a nucleophilic reactive group, R2 comprises a linker, and R3 is a polymer synthesis initiator moiety and s is an integer between 1 and 20. R1 is preferably selected from the group consisting of $NH_2-$, $OH-$, and $SH$. More preferably, R1 is $NH_2-$.

In accordance with this aspect of the present invention, R2 is preferably alkyl, substituted alkyl, alkylene, alkoxy, carboxyalkyl, haloalkyl, cycloalkyl, cyclic alkyl ether, alkenyl, alkenylene, alkynyl, alkynylene, cycloalkylene, heterocycloalkyl, heterocycloalkylene, aryl, arylene, arylene-oxy, heteroaryl, amino, amido or any combination thereof.

More preferably, R2 comprises a structure having the formula:

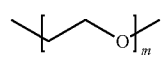

wherein m is 1 to 20. m is preferably 4.

In accordance with the present invention, R3 preferably has the following formula

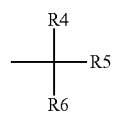

wherein R4, R5 and R6 are the same or different and are selected from the group consisting of

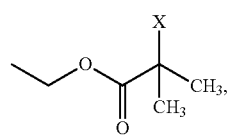

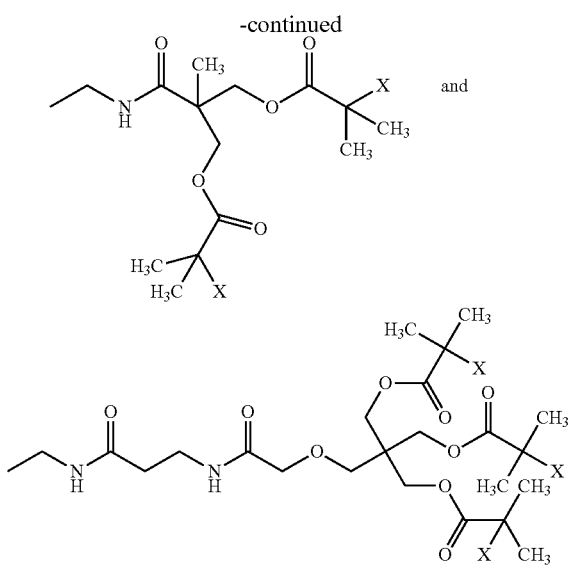

wherein X is NCS, F, Cl, Br or I. Preferably X is Br.

In more preferred aspects of the present invention, R4, R5 and R6 are each

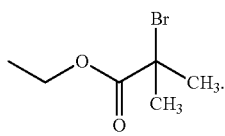

Alternatively, R4, R5 and R6 are each

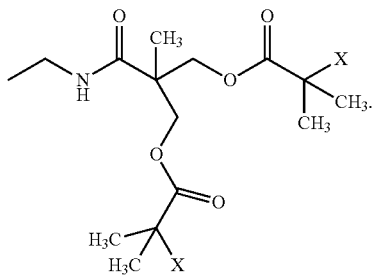

In still other preferred embodiments, R4, R5 and R6 are each

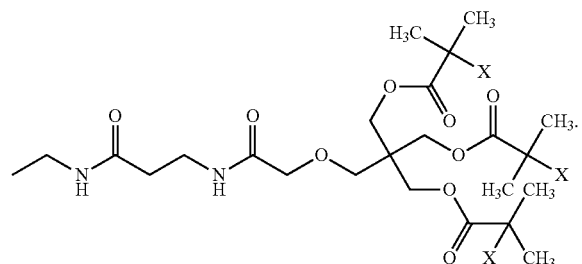

In accordance with this aspect of the present invention, the monomer is preferably selected from the group consisting of

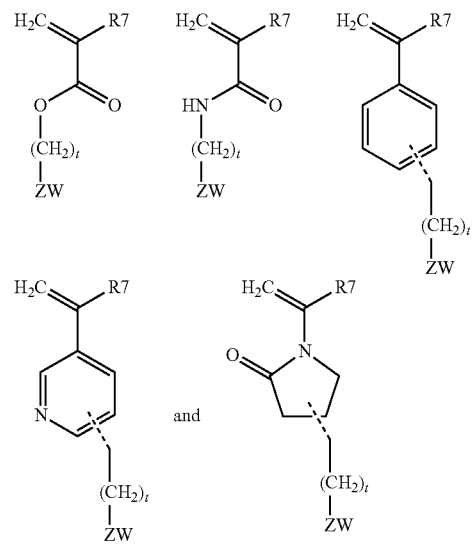

wherein R7 is H or $C_{1-6}$ alkyl, ZW is a zwitterion and t is 1 to 6. Preferably, the zwitterion is phosphorylcholine.

Still more preferably, the monomer is selected from the group consisting of 2-(methacryloyloxyethyl)-2'-(trimethylammoniumethyl) phosphate (HEMA-PC) and 2-(acryloyloxyethyl)-2'-(trimethylammoniumethyl) phosphate. Most preferably, the monomer is 2-(methacryloyloxyethyl)-2'-(trimethylammoniumethyl) phosphate.

In accordance with an aspect of the present invention, the linker moiety of step d is preferably an activated ester having the structure

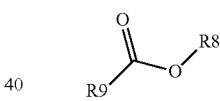

wherein R8 is selected from the group consisting of

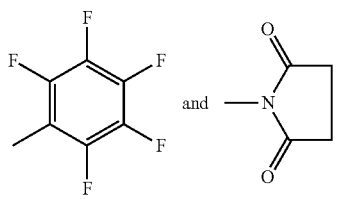

and R9 is selected from the group consisting of

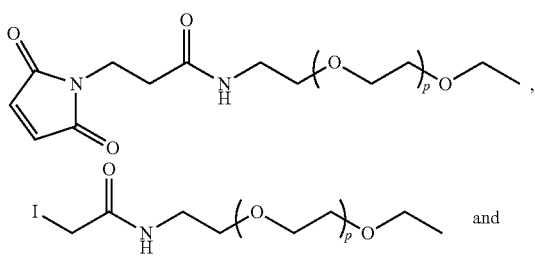

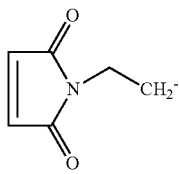

wherein p is 1 to 12.
Preferably, the linker moiety is

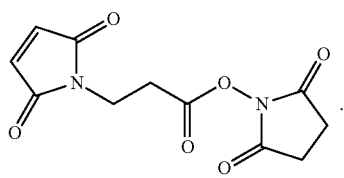 [SMILES: O=C(CCN1C(=O)C=CC1=O)ON1C(=O)CCC1=O]

In accordance with an aspect of the present invention, the initiator of step a. preferably has the following structure:

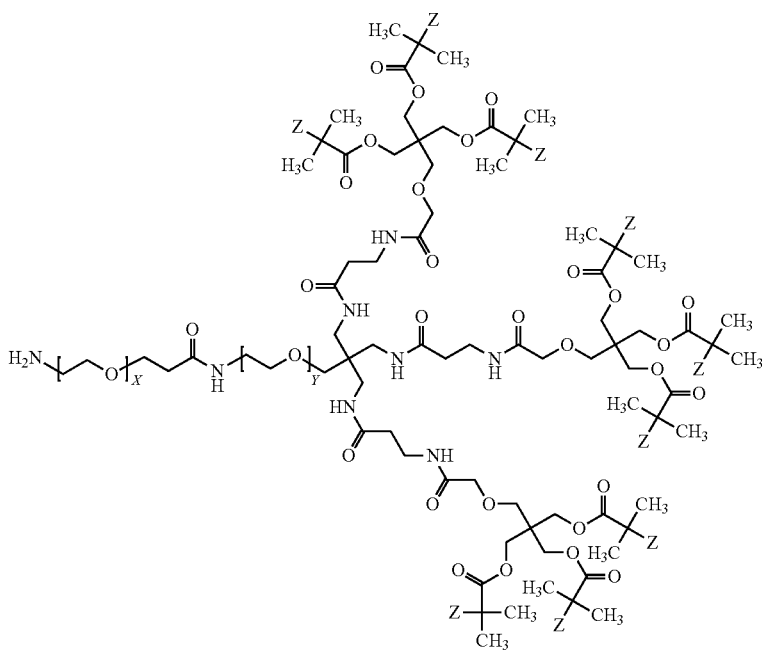

wherein y is an integer from 1 to 50, X is an integer from 0 to 50 and Z is NCS, F, C, Br or I. Preferably, Z is Br, X is 4, 8 or 12 and Y is 1 to 10. More preferably, Y is 4.

In accordance with this aspect of the present invention, the linker-polymerized initiator of step f preferably has the formula:

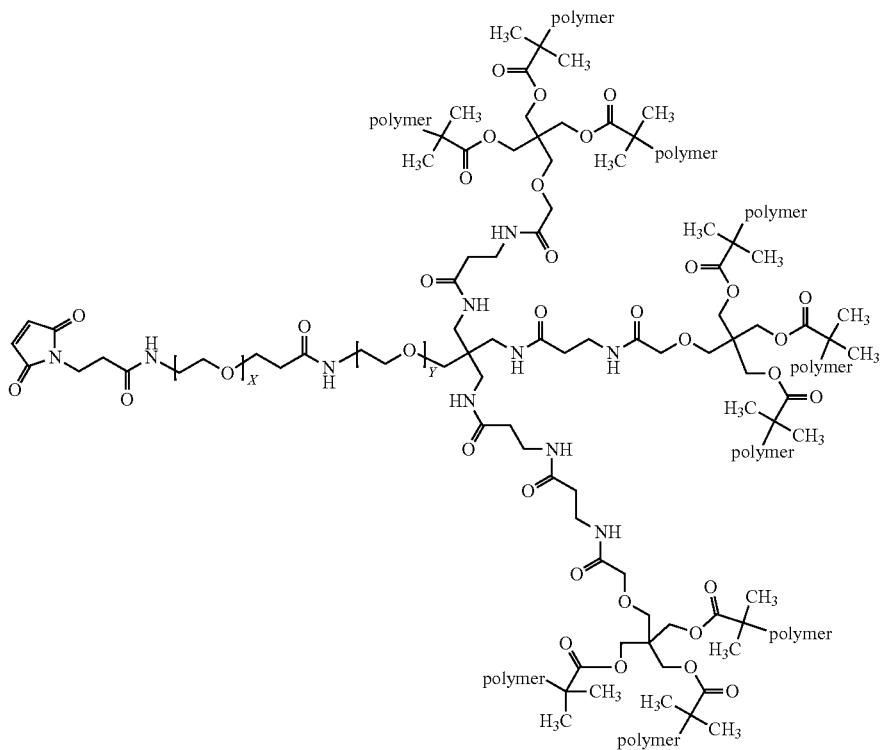

wherein X is an integer from 1 to 50, Y is an integer from 1-50 and Polymer is any polymer synthesized with a monomer as defined herein. More preferably Y is 4, X is 4, 8 or 12 and the monomer is HEMA-pc.

Preferably, the functional agent is a protein. More preferably, the protein comprises human FVIII. Still more preferably, the FVIII is a recombinant FVIII (rFVIII) which is preferably purified from a human host cell. Most preferably, the FVIII has a deletion of part or all of the B domain.

In accordance with an aspect of the present invention, a compound is presented having the formula:

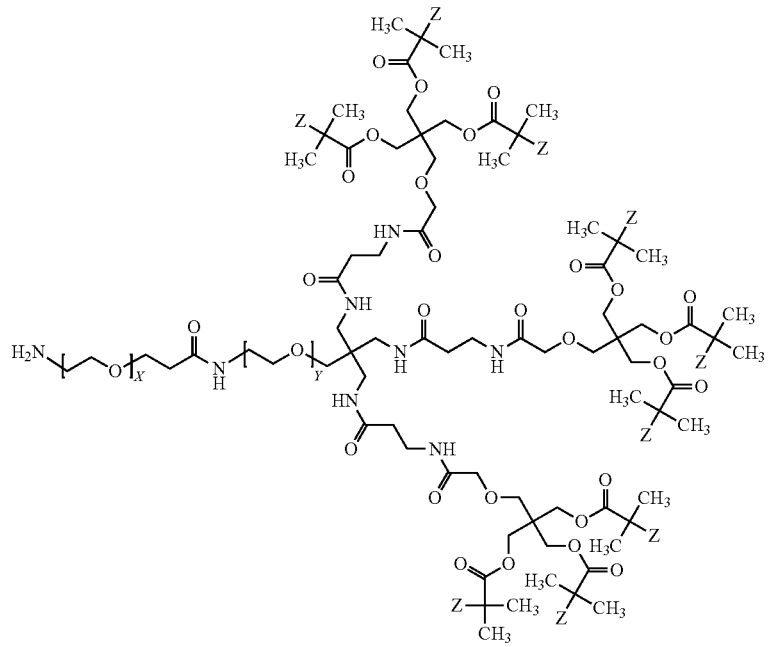

wherein y is a integer from 1 to 50, X is an integer from 0 to 50 and Z is NCS, F, Cl, Br, or I. Preferably, Z is Br, X is 4, 8, or 12 and Y is 1 to 10. More preferably, Y is 4.

In accordance with another aspect of the present invention, a polymer is presented having the formula:

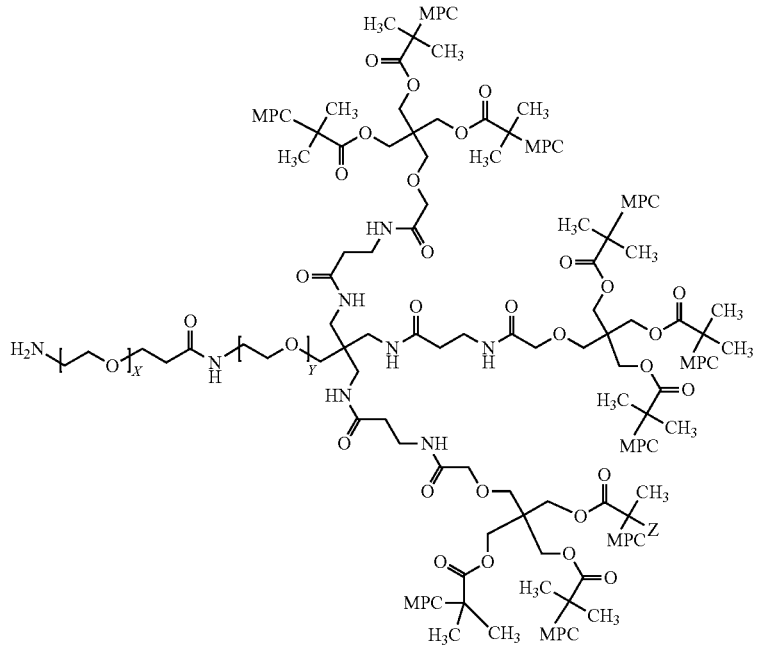

wherein y is an integer from 1 to 50, X is an integer from 0 to 50 and MPC is a polyMPC arm. PolyMPC is prepared using is 2-(methacryloyloxyethyl)-2'-(trimethylammoniumethyl) phosphate in a polymerization reaction, e.g., ATRP. Preferably, the total molecular weight of the polymer is about 500,000 to about 1,000,000 Daltons. More preferably, the total molecular weight of the polymer is about 650,000 to about 850,000 daltons. Still more preferably, the total molecular weight of the polymer is about 750,000 daltons.

In accordance with this aspect of the present invention X is preferably 4, 8 or 12 and Y is 1 to 10. Still more preferably, Y is 4.

Such an initiator be used, in accordance with the present invention as the substrate for polymer synthesis. Preferably, the polymer synthesis is conducted using ATRP or like method, such as generated by AGET (Woodworth et al., Macromolecules, Vol. 31, No. 23, 1998) or ARGET (Macromolecules, 2012, 45 (16), pp 6371-6379 (Simakova, A. et al)). Any of the monomers described herein may be used for polymer synthesis.

Pharmaceutical compositions adapted for oral administration may be presented as discrete units such as capsules, as solutions, syrups or suspensions (in aqueous or non-aqueous liquids; or as edible foams or whips; or as emulsions). Suitable excipients for tablets or hard gelatine capsules include lactose, maize starch or derivatives thereof, stearic acid or salts thereof. Suitable excipients for use with soft gelatine capsules include for example vegetable oils, waxes, fats, semi-solid, or liquid polyols etc. For the preparation of solutions and syrups, excipients which may be used include for example water, polyols and sugars. For the preparation of suspensions oils (e.g. vegetable oils) may be used to provide oil-in-water or water in oil suspensions.

Pharmaceutical compositions adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable compositions wherein the carrier is a liquid, for administration as a nasal spray or as nasal drops, include aqueous or oil solutions of the active ingredient. Pharmaceutical compositions adapted for administration by inhalation include fine particle dusts or mists which may be generated by means of various types of metered dose pressurized aerosols, nebulizers or insufflators.

Pharmaceutical compositions adapted for parenteral administration include aqueous and non-aqueous sterile injection solution which may contain anti-oxidants, buffers, bacteriostats and solutes which render the formulation substantially isotonic with the blood of the intended recipient; and aqueous and non-aqueous sterile suspensions which may include suspending agents and thickening agents. Excipients which may be used for injectable solutions include water, alcohols, polyols, glycerine and vegetable oils, for example. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets. Pharmaceutical compositions can be substantially isotonic, implying an osmolality of about 250-350 mOsm/kg water.

In general, the pharmaceutical compositions may contain preserving agents, solubilizing agents, stabilizing agents, wetting agents, emulsifiers, sweeteners, colorants, odorants, salts (substances of the present invention may themselves be provided in the form of a pharmaceutically acceptable salt), buffers, coating agents or antioxidants. They may also contain therapeutically active agents in addition to the substance of the present invention. The pharmaceutical compositions of the invention may be employed in combination with pharmaceutically acceptable diluents, adjuvants, or carriers. Such excipients may include, but are not limited to, saline, buffered saline (such as phosphate buffered saline), dextrose, liposomes, water, glycerol, ethanol and combinations thereof.

The pharmaceutical compositions may be administered in any effective, convenient manner effective for treating a patients disease including, for instance, administration by oral, intravenous, subcutaneous, intramuscular, intraosseous, intranasal, or routes among others. In therapy or as a prophylactic, the active agent may be administered to an individual as an injectable composition, for example as a sterile aqueous dispersion, preferably isotonic.

For administration to mammals, and particularly humans, it is expected that the daily dosage of the active agent will be from 0.01 mg/kg body weight, typically around 1 mg/kg. The physician in any event will determine the actual dosage which will be most suitable for an individual which will be dependent on factors including the age, weight, sex and response of the individual. The above dosages are exemplary of the average case. There can, of course, be instances where higher or lower dosages are merited, and such are within the scope of this invention.

Dosages of the substance of the present invention can vary between wide limits, depending upon the disease or disorder to be treated, the age and condition of the individual to be treated, etc. and a physician will ultimately determine appropriate dosages to be used.

This dosage may be repeated as often as appropriate. If side effects develop the amount and/or frequency of the dosage can be reduced, in accordance with normal clinical practice. In one embodiment, the pharmaceutical composition may be administered once every one to thirty days.

According to a third aspect of the invention, there is provided a pharmaceutical composition of the second aspect and another pharmaceutically active agent. The other pharmaceutically active agent may promote or enhance the activity of FVIII, for example another blood coagulation factor.

The pharmaceutical compositions of the invention may be employed alone or in conjunction with other compounds, such as therapeutic compounds or molecules, e.g. anti-inflammatory drugs, analgesics or antibiotics. Such administration with other compounds may be simultaneous, separate or sequential. The components may be prepared in the form of a kit which may comprise instructions as appropriate.

Preferably, the pharmaceutical composition of the invention and the other therapeutic compound are directly administered to a patient in need thereof.

The invention also provides a kit of parts comprising a pharmaceutical composition of invention, and an administration vehicle including, but not limited to, capsules for oral administration, inhalers for lung administration and injectable solutions for intravenous administration.

According to a fourth aspect of the invention, there is provided a method of treatment of a blood clotting disease where the method comprises administration of a composition of the present invention to a patient in need thereof. This aspect of the invention therefore also includes uses of such compositions in said methods.

Blood clotting diseases may be characterized by a loss of function of a blood clotting factor, or the generation of auto-antibodies. Examples of blood clotting diseases includes hemophilia A and acquired hemophilia A.

As used herein, the term "treatment" includes any regime that can benefit a human or a non-human animal. The treatment of "non-human animals" extends to the treatment of domestic animals, including horses and companion animals (e.g. cats and dogs) and farm/agricultural animals including members of the ovine, caprine, porcine, bovine and equine families. The treatment may be in respect of any existing condition or disorder, or may be prophylactic (preventive treatment). The treatment may be of an inherited or an acquired disease. The treatment may be of an acute or chronic condition.

Nucleophilic groups on proteins, including antibodies, which can be used to conjugate polymer in accordance with an aspect of the present invention include, but are not limited to: (i) N-terminal amine groups, (ii) side chain amine groups, e.g. lysine, (iii) side chain thiol groups, e.g. cysteine, and (iv) sugar hydroxyl or amino groups where the protein is glycosylated. Amine, thiol, and hydroxyl groups are nucleophilic and capable of reacting to form covalent bonds with electrophilic groups on linker moieties and linker reagents attached to the polymer including: (i) active esters such as NHS esters, HOBt esters, haloformates, and acid halides; (ii) alkyl and benzyl halides such as haloacetamides; (iii) aldehydes, ketones, carboxyl, and maleimide groups. Many proteins, including antibodies, have cysteine thiol groups which can potentially be used for conjugation. Many cysteine residues are in the form of reducible interchain disulfides, i.e. cysteine bridges. Cysteine residues in the form of disulfides are generally not available to react with reagents such as maleimide. Cysteine residues may also be free or unpaired. However, free cysteine residues are frequently found to be "capped" by one or more reagents in various media and are also not available for conjugation. Cysteine residues may be made reactive for conjugation with linker reagents such as maleimide by treatment with a reducing agent such as DTT (dithiothreitol) or tricarbonylethylposphine (TCEP), such that the protein is fully or partially reduced. Each cysteine bridge will thus form, theoretically, two reactive thiol nucleophiles. In the case of free cysteine, one thiol nucleophile is formed by reduction. Depending on the conditions employed, reduction by TCEP or DTT can result in the loss of proper protein folding with concomitant loss of activity. However, activity may be recovered by allowing protein refolding under the appropriate conditions.

Additional nucleophilic groups can be introduced into antibodies through modification of lysine residues, e.g., by reacting lysine residues with 2-iminothiolane (Traut's reagent), resulting in conversion of an amine into a thiol. Reactive thiol groups may be introduced into a protein by introducing one, two, three, four, or more cysteine residues (e.g., by preparing variant comprising one or more non-native cysteine amino acid residues).

IV. Examples

Synthesis of Initiators

Example 1. Preparation of 3-Arm "Snap-On" Initiator

A TFA/amine salt initiator (Compound B) having the structure below was synthesized as follows.

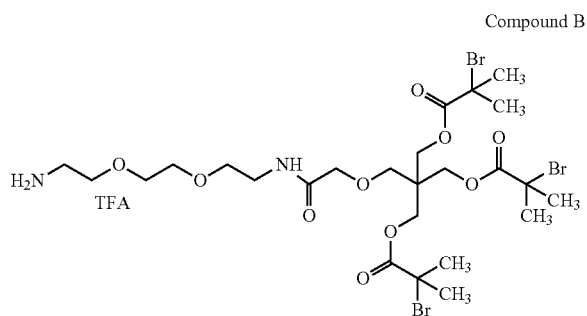 [SMILES: CC(C)(Br)C(=O)OCC(COCC(=O)NCCOCCOCCN)(COC(=O)C(C)(C)Br)COC(=O)C(C)(C)Br]

Compound B

First, a BOC protected 3-arm initiator, Compound A, having the following structure:

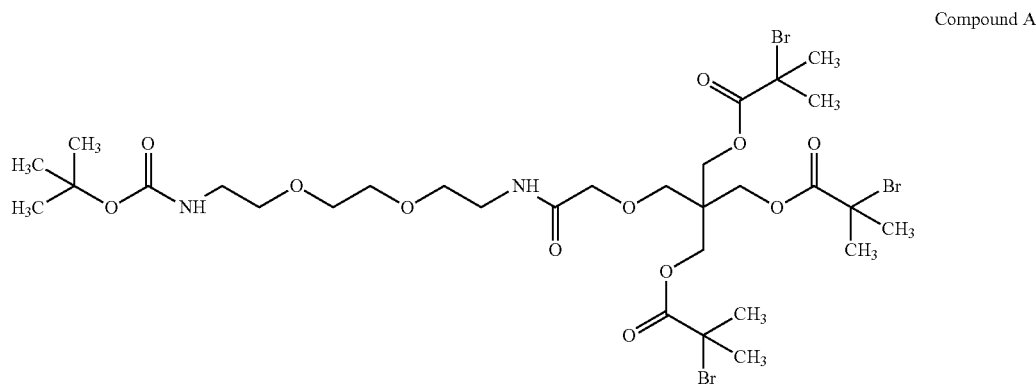 [SMILES: CC(C)(C)OC(=O)NCCOCCOCCNC(=O)COCC(COC(=O)C(C)(C)Br)(COC(=O)C(C)(C)Br)COC(=O)C(C)(C)Br]

Compound A was prepared as follows: into a 25 mL round bottom flask under nitrogen was placed tert-butyl 2-[2-(2-aminoethoxy)ethoxy]ethylcarbamate (66 mg, 0.26 mmol, 1.2 equiv) and (2,2,2-Tri(2-bromo-2-methyl-propionyloxymethyl)-ethoxy)-acetic acid (prepared as described in PCT/US2012/060301 for Product 4.5, which is incorporated herein by reference) (142 mg, 0.22 mmol, 1.0 equiv) followed by N,N-dimethylformamide (2 mL) and then N,N-diisopropylethylamine (0.19 mL, 1.1 mmol, 5.0 equiv). The flask was cooled to 0° C. using an ice bath. To this was added propylphosphonic anhydride solution (50 wt. % in ethyl acetate, 0.16 mL, 0.26 mmol, 1.2 equiv) over 1 minute. The reaction was warmed to room temperature and stirred for 1.5 hours. The reaction was quenched by adding water, then partitioned using water and ethyl acetate. The organic layer was separated and the aqueous layer extracted with ethyl acetate. The combined organic layers were washed with water, saturated aqueous sodium bicarbonate, water, 0.5 M aqueous citric acid, water, then dried (sodium sulfate), filtered and concentrated under vacuum. The residue was applied onto a silica gel column (60 mL) and eluted with 70% ethyl acetate with 30% hexanes. The tubes containing product was pooled and concentrated under vacuum, which resulted in 150 mg (0.17 mmol, 77%) of Compound A.

1H NMR (400 MHz CDCl3): δ=Need to put in data 1.44 (s, 91H, OC$\underline{CH_3}$), 1.96 (s, 18H, CC($\underline{CH_3}$)2Br), 3.31 (q, J=4.8 Hz, 2H, OCNH$\underline{CH_2}$CH2O), 3.5-3.6 (m, 12H), 3.99 (s, 2H, O$\underline{CH_2}$C), 4.32 (s, 6H, C$\underline{CH_2}$OC=O), 5.0 (br s, 1H, CH2N$\underline{H}$C=OO), 6.8 (br s, 1H, CH2N$\underline{H}$C=OC), LC-MS (ES, m/z): [M+H]+ Calcd for C30H51Br3N2O12+H=871.1; Found 871.8.

Compound A was de-protected to yield Compound B as follows: into a 20 mL round bottom under nitrogen was added Compound A (120 mg, 0.14 mmol, 1 equiv), dichloromethane (2 mL) followed by trifluoroacetic acid (2 mL, 26.9 mmol, 192 equiv). The reaction stirred at room temperature for 30 minutes. The reaction was diluted using hexanes dichloromethane (20 mL) and concentrated under a vacuum. The reaction was diluted using hexanes (50 mL) and concentrated under vacuum (twice), which resulted in 2.2 g (2.73 mmol, (with residual dichloromethane)) of compound B.

1H NMR (400 MHz CDCl3): δ=1.94 (s, 18H, CC(CH3)2Br), 3.2 (br, 2H, OCNHCH2CH20), 3.5-3.8 (m, 12H), 3.99 (s, 2H, O$\underline{CH_2}$C), 4.34 (s, 6H, CCH20C=O), 7.11 (br t, 1H, CH2N$\underline{H}$C=0), 7.99 (br, 3H, $\underline{NH_3+}$).

LC-MS (ES, m/z): [M+H]+ Calcd for C25H43Br3N2O10+H=771.1; Found 771.6.

Example 2. Preparation of 6-Arm "Snap-On" Initiator

A TFA/amine salt initiator (Compound F1) having the structure below was synthesized

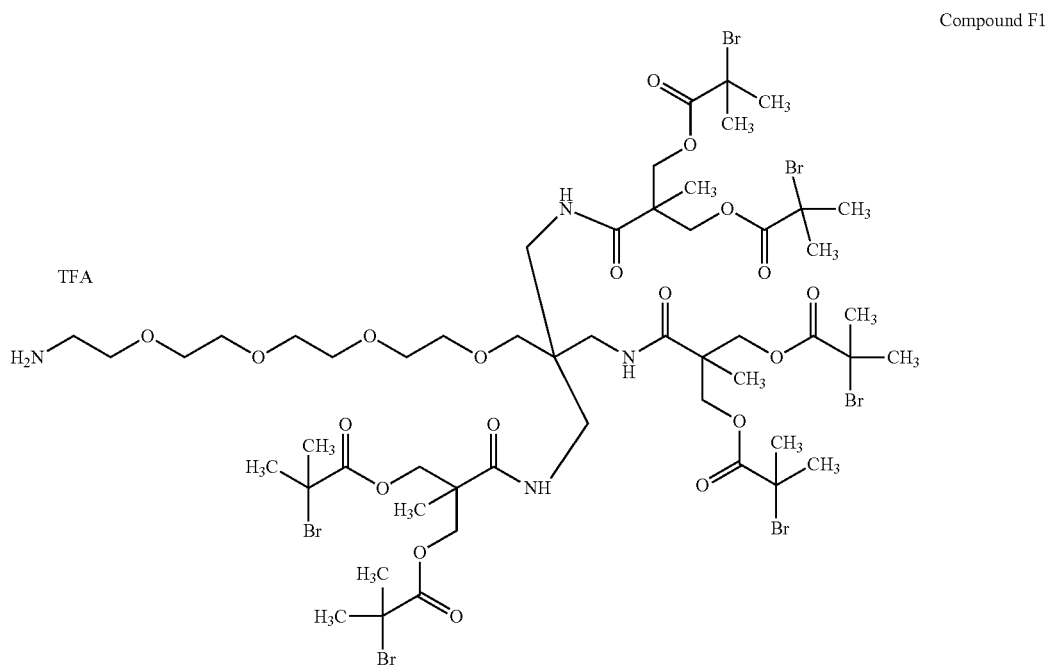 [SMILES: CC(C)(Br)C(=O)OCC(C)(COC(=O)C(C)(C)Br)C(=O)NCC(CNC(=O)C(C)(COC(=O)C(C)(C)Br)COC(=O)C(C)(C)Br)(CNC(=O)C(C)(COC(=O)C(C)(C)Br)COC(=O)C(C)(C)Br)COCCOCCOCCOCCN]

Compound F1

As a first step in preparing F1, Compound C, having the following structure, was synthesized:

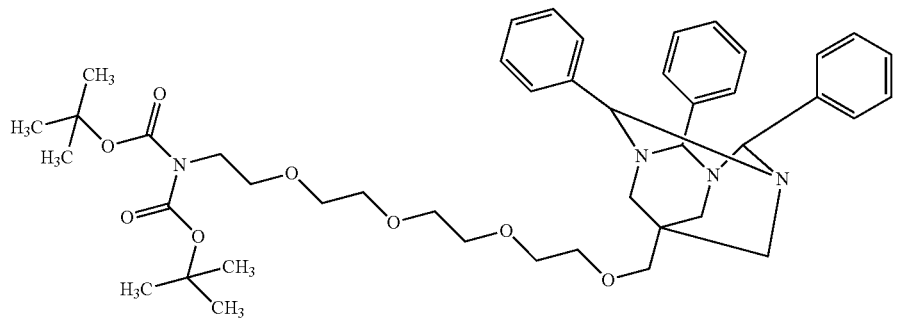 [SMILES: CC(C)(C)OC(=O)N(CCOCCOCCOCCOCC12CN3C(c4ccccc4)N(C1)C(c1ccccc1)N(C2)C3c1ccccc1)C(=O)OC(C)(C)C]

into a 100 mL round bottom under nitrogen and using a reflux condenser was added 1-tosyl-11-(3,4,7-triaza-4,6,10-triphenyl-adamantan-1-yl methoxy)-3,6,9-trioxaundecane (prepared as described in PCT/US2012/060301 for Product 2.2) (4.0 g, 5.5 mmol, 1.0 equiv), di(tert-butyl) imidodicarbonate (1.43 g, 6.6 mmol, 1.2 equiv), potassium carbonate (1.9 g, 13.7 mmol, 2.5 equiv), potassium iodide (0.137 g, 0.82 mmol, 0.15 equiv) followed by acetonitrile (25 mL). The reaction was stirred at room temperature for 5 minutes followed by stirring at 60° C. for 30 hours. The reaction was quenched by adding water (25 mL) and tert-butyl methyl ether (125 mL). The organic layer was separated and the aqueous layer extracted with tert-butyl methyl ether (75 mL). The combined organic layers were washed with saturated aqueous sodium chloride (20 mL), then dried (sodium sulfate), filtered and concentrated under vacuum. The residue was applied onto a silica gel column (195 g, 6.5 cm×12 cm) and eluted with 20% tert-butyl methyl ether in 80% hexanes up to 100% tert-butyl methyl ether. The tubes containing product were pooled and concentrated under vacuum, which resulted in 3.7 g (4.79 mmol, 87%) of Compound C.

1H NMR (400 MHz DMSO-d6): δ=1.42 (s, 18H, C[C(CH3)3]2), 2.72 (s, 2H, C<u>CH2</u>N, isomer), 2.88 (s, 2H, CCH2N, isomer), 3.2-3.6 (m, 20H), 5.25 (s, 2H, NCHPh, isomer), 5.70 (s, 1H, NCHPh, isomer), 7.3-7.8 (m, 15H, phenyl).

Next Compound D having the following structure was synthesized:

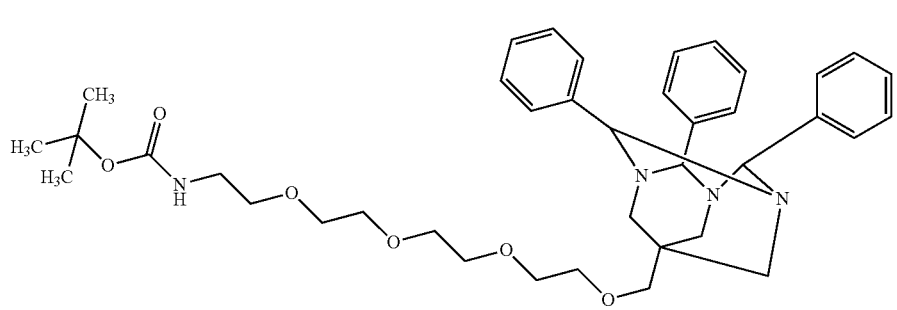

Compound D into a 500 mL round bottom under nitrogen and using a reflux condenser was added Compound C (2.7 g, 3.49 mmol, 1.0 equiv), lithium hydroxide monohydrate (0.73 g, 17.5 mmol, 5 equiv), tetrahydrofuran (20 mL), methanol (8 mL) followed by water (8 mL). The reaction was stirred at 60° C. for 6 hours. The reaction was concentrated under vacuum and then partitioned by adding water (75 mL) and ethyl acetate (100 mL). The organic layer was separated and the aqueous layer extracted with ethyl acetate (50 mL). The combined organic layers were washed with saturated aqueous sodium chloride (30 mL), then dried (sodium sulfate), filtered and concentrated under vacuum. The residue was applied onto a silica gel column (110 g, 5.5 cm×10.5 cm) and eluted with 50% hexanes in 50% tert-butyl methyl ether up to 100% tert-butyl methyl ether. The tubes containing product were pooled and concentrated under vacuum, which resulted in 1.38 g (2.05 mmol, 59%) of Compound D.

1H NMR (400 MHz DMSO-d6): δ=1.36 (s, 9H, C[C(CH3)3]2), 2.72 (s, 2H, CCH2N, isomer), 2.88 (s, 2H, C CH2N, isomer), 3.1-3.4 (m, 20H), 5.25 (s, 2H, NCHPh (isomer)), 5.70 (s, 1H, NCHPh (isomer)), 6.73 (t, J=6.0 Hz, 1H, O=CNHCH2), 7.3-7.7 (m, 15H, phenyl).

The next step in preparing F1 was the synthesis of Compound E which has the following structure:

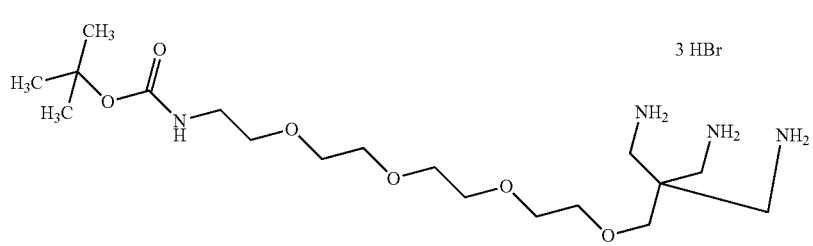

Compound E

3 HBr into a 100 mL round bottom was added Compound D (2.96 g, 4.4 mmol, 1.0 equiv), diethyl ether (20 mL) followed by water (16 mL). The flask was cooled to 0° C. using an ice bath. To this was added hydrobromic acid solution (48 wt. % in water) (1.64 mL, 14.5 mmol, 3.3 equiv). The reaction was stirred at 0° C. rapidly for 1 hour. The organic layer was separated and the aqueous layer was returned to the reaction flask at 0° C. where diethyl ether (20 mL) was added and the stirring continued for 15 minutes. The organic layer was separated again and the aqueous layer was returned to the reaction flask at 0° C. where diethyl ether (20 mL) was added and the stirring continued for 10 minutes. The organic layer was separated and the aqueous layer was pH adjusted to 4.5 by addition of IM aqueous sodium hydroxide. The water was removed by azeotroping with acetonitrile under a vacuum, which resulted in 2.5 g (3.85 mmol, 87%) of Compound E as a white solid.

1H NMR (400 MHz DMSO-d6): δ=1.36 (s, 9H, OC(CH3)3), 3.05-3.58 (m, 24H, CH2), 6.8 (t, 1H, O=C NHCH2), 8.0 (br s, 9H, CH2NH2*HBr).

LC-MS (ES, m/z): [M+H]+ Calcd for C18H40N4O6+ H=409.3; Found 409.6.

The next step in preparation of Compound F1 was the synthesis of Compound F, which has the following structure:

Compound F1

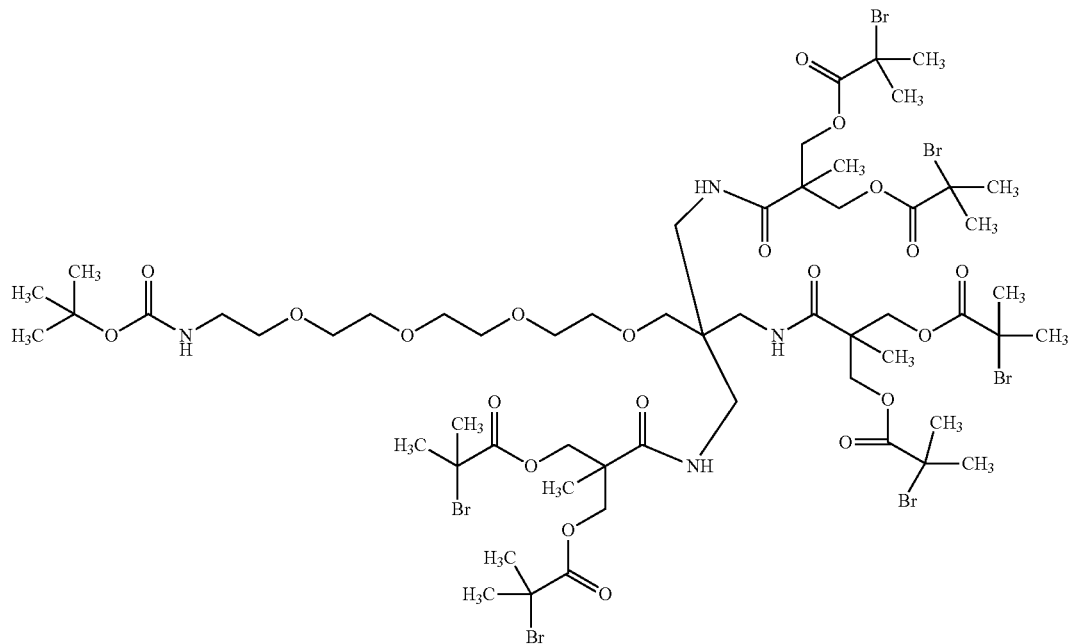

into a 200 mL round bottom flask under nitrogen was placed bis 2,2-[(2-bromoisobutyryl)hydroxymethyl]propionic acid (prepared as described in example 7 of U.S. patent application Ser. No. 13/641,342, which is incorporated herein by reference) (2.32 g, 5.37 mmol, 3.3 equiv) and Compound E (1.06 g, 1.63 mmol, 1.0 equiv) followed by dimethylformamide (15 mL) then diisopropylethylamine (3.4 mL, 19.5 mmol, 12 equiv). To this was added propylphosphonic anhydride solution (50 wt. % in ethyl acetate, 3.7 mL, 5.87 mmol, 3.5 equiv). The reaction was stirred for 60 minutes. The reaction was quenched by adding water (1 mL) and loaded onto a preparatory HPLC column and eluted with 50% acetonitrile in water (with 0.1% trifluoroacetic acid) up to 95% acetonitrile (with 0.1% trifluoroacetic acid). The tubes containing product were pooled, concentrated under vacuum, frozen and placed on a lyophilizer. This resulted in 640 mgs (0.39 mmol, 24%) Compound F.

Lastly, the tBOC protective group was removed to provide the final initiator, FI, which has the structure shown above. Into a 50 mL round bottom was added Product 174-44 (600 mg, 0.36 mmol) and dichloromethane (3.6 mL). The flask was cooled to 0° C. using an ice bath. To this was added trifluoroacetic acid (3.6 mL). The reaction was stirred at room temperature for 45 minutes. The reaction was diluted with hexanes and then concentrated under a vacuum. The reaction was diluted using hexanes and concentrated under a vacuum. The residue was dissolved using acetonitrile (3 mL), diluted with water (1.5 mL), frozen and placed on a lyophilizer. This resulted in 537 mgs (0.32 mmol, 89%) of Compound Fl as an oil.

Example 3. Preparation of 9-Arm "Snap-On" Initiator Compound L

A TFA/amine salt initiator (Compound L) having the structure below was synthesized as follows.

Compound L
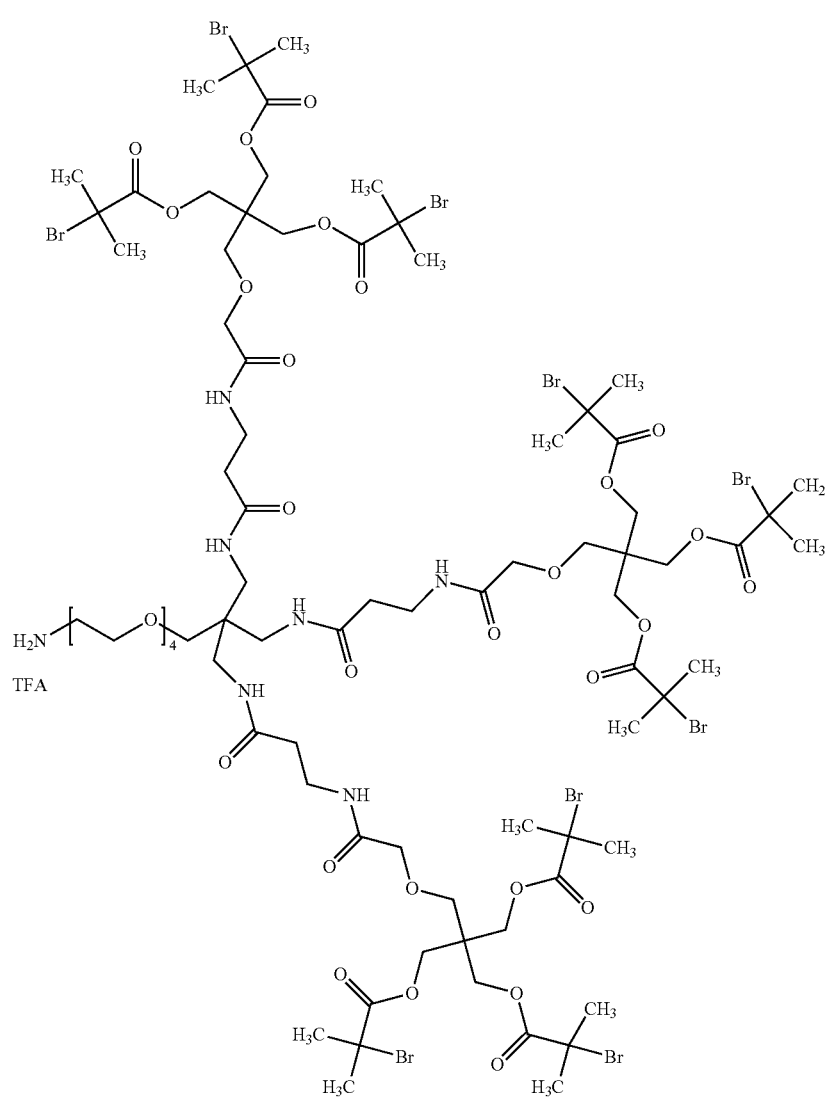
First, Compound K, having the following structure, was synthesized:

Compound K

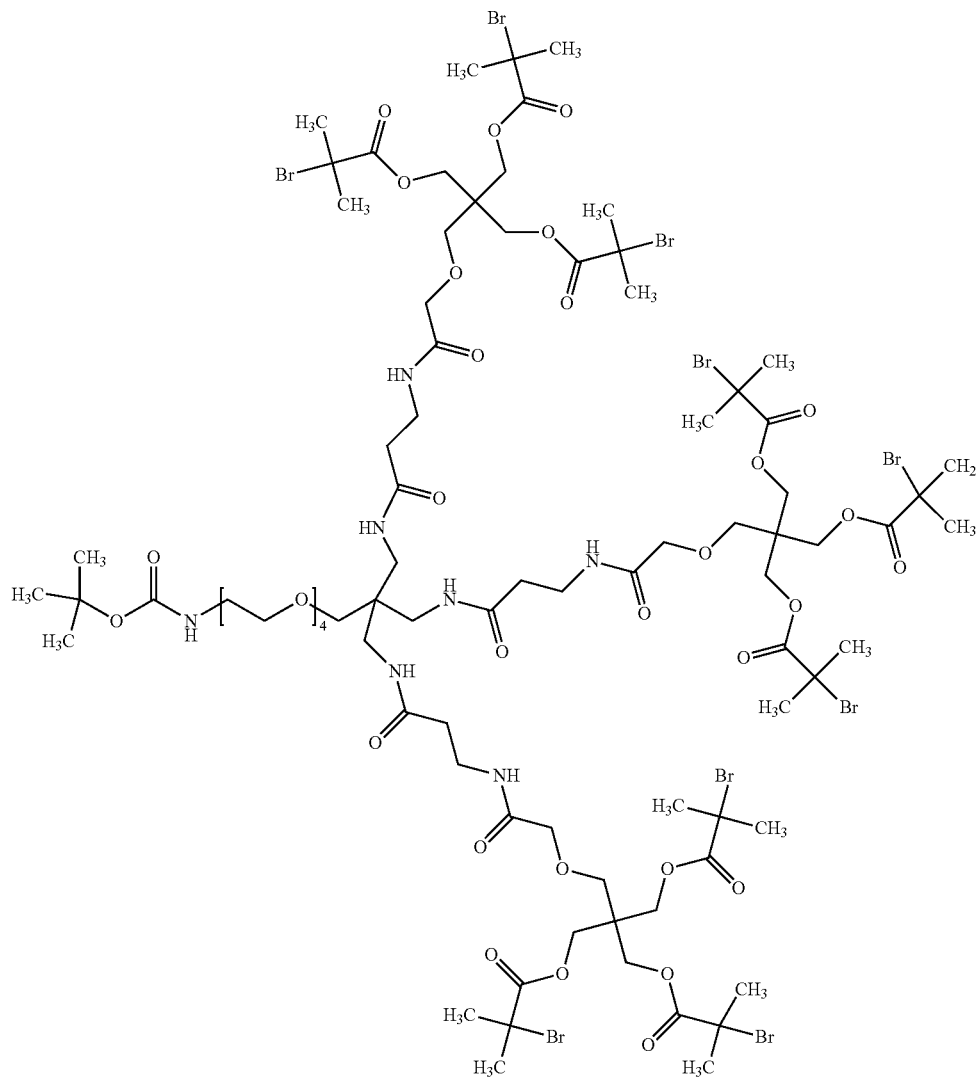

into a 200 mL round bottom flask under nitrogen was placed Compound J (1.9 g, 2.67 mmol, 3.3 equiv)

Compound J

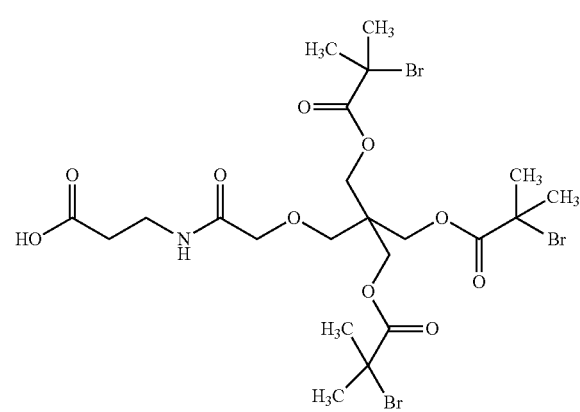

and Compound E (0.525 g, 0.81 mmol, 1.0 equiv) (see above) followed by dimethylformamide (10 mL) then diisopropylethylamine (2.5 mL, 14.6 mmol, 18 equiv). The flask was cooled to 0° C. using an ice bath. To this was added propylphosphonic anhydride solution (50 wt. % in ethyl acetate, 2.5 mL, 4.04 mmol, 5 equiv) over ~6 minutes.

The reaction was warmed to room temperature and stirred for 15 minutes. The reaction was quenched by adding water (20 mL), saturated aqueous sodium bicarbonate (20 mL) and ethyl acetate (100 mL). The organic layer was separated and the aqueous layer extracted with ethyl acetate (75 mL). The combined organic layers were washed with saturated aqueous sodium bicarbonate (30 mL), 0.5 M aqueous citric acid (40 mL), water (25 mL), and saturated aqueous sodium chloride (40 mL), then dried (sodium sulfate), filtered and concentrated under vacuum. The residue which was used without further purification resulted in 2.0 g (0.80 mmol, 99%) of Compound K.

1H NMR (400 MHz DMSO-d6): δ=1.36 (s, 9H, OCCH3), 1.90 (s, 54H, CC(CH3)2Br), 2.31 (t, J=7.2 Hz, 6H, CCH2CH2NH), 2.98 (d, J=5.6 Hz, 6H, CCH2NH), 3.04 (q, J=6.0 Hz, 2H, OCH2CH2NH), 3.18 (s, 2H, OCH2C), 3.3-

3.37 (m, 8H, CH2), 3.47-3.55 (m, 12H, CH2), 3.58 (s, 6H, OCH2C), 3.87 (s, 6H, O═CCH2O), 4.27 (s, 18H, C CH2OC═O), 6.74 (br t, 1H, CH2NHC═O), 7.69 (t, J=6.8 Hz, 3H, CH2NHC═O), 7.84 (t, J=6.0 Hz, 3H, CH2 NHC═O).

LC-MS (ES, m/z): [(M+2H-boc)/2]+ Calcd for (C84H136Br9N7O33+2H-Boc)/2=1196.6; Found 1196.6.

Next, Compound L was synthesized as follows: into a 100 mL round bottom under nitrogen was added Compound K (2.0 g, 0.8 mmol), dichloromethane (10 mL) followed by trifluoroacetic acid (5 mL). The reaction was stirred at room temperature for 30 minutes. The reaction was concentrated under a vacuum. The reaction was diluted using dichloromethane (10 mL) and concentrated under a vacuum. The residue was dissolved using acetonitrile (10 mL), filtered through a syringe filter (Acrodisc CR25, PN 4225T) and loaded onto a preparatory HPLC column and eluted with 60% acetonitrile in water (with 0.1% trifluoroacetic acid) up to 98% acetonitrile (with 0.1% trifluoroacetic acid). The tubes containing product were pooled, concentrated under vacuum, frozen and placed on a lyophilizer. This resulted in 990 mgs (0.4 mmol, 50% over 2 steps) Compound L as a white powder.

1H NMR (400 MHz DMSO-d6): δ=1.90 (s, 54H, CC (CH3)2Br), 2.31 (t, J=7.2 Hz, 6H, CCH2CH2NH), 2.97-3.0 (m, 8H, CCH2NH and OCH2CH2NH), 3.17 (s, 2H, O CH2C), 3.3 (q, 6H, CH2CH2NHC═O), 3.4-3.59 (m, 20H, CH2), 3.87 (s, 6H, O═CCH2O), 4.27 (s, 18H, C CH2OC═O), 7.69-7.84 (m, 9H, both CH2NHC═O and NH3+).

LC-MS (ES, m/z): [(M+2H)/2]+ Calcd for (C84H136Br9N7O33+2H)/2=1196.6; Found 1197.4.

Example 4. Preparation of Longer Spacer 9-Arm Initiator SnapOn Initiator Compound O A TFA/amine salt initiator (Compound O) having the structure below was synthesized as follows:

Compound O

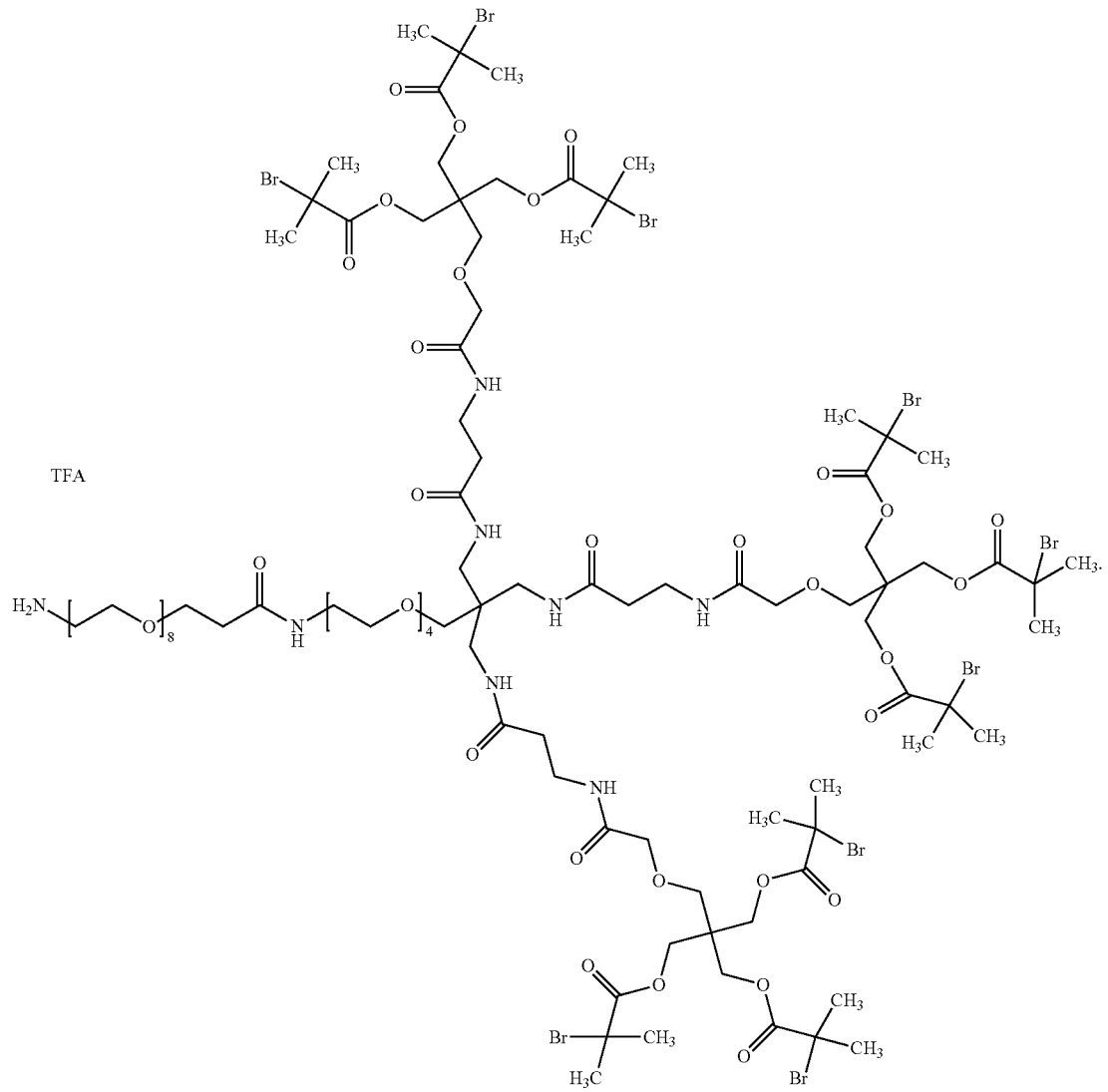

First, Compound M, having the following structure, was synthesized:

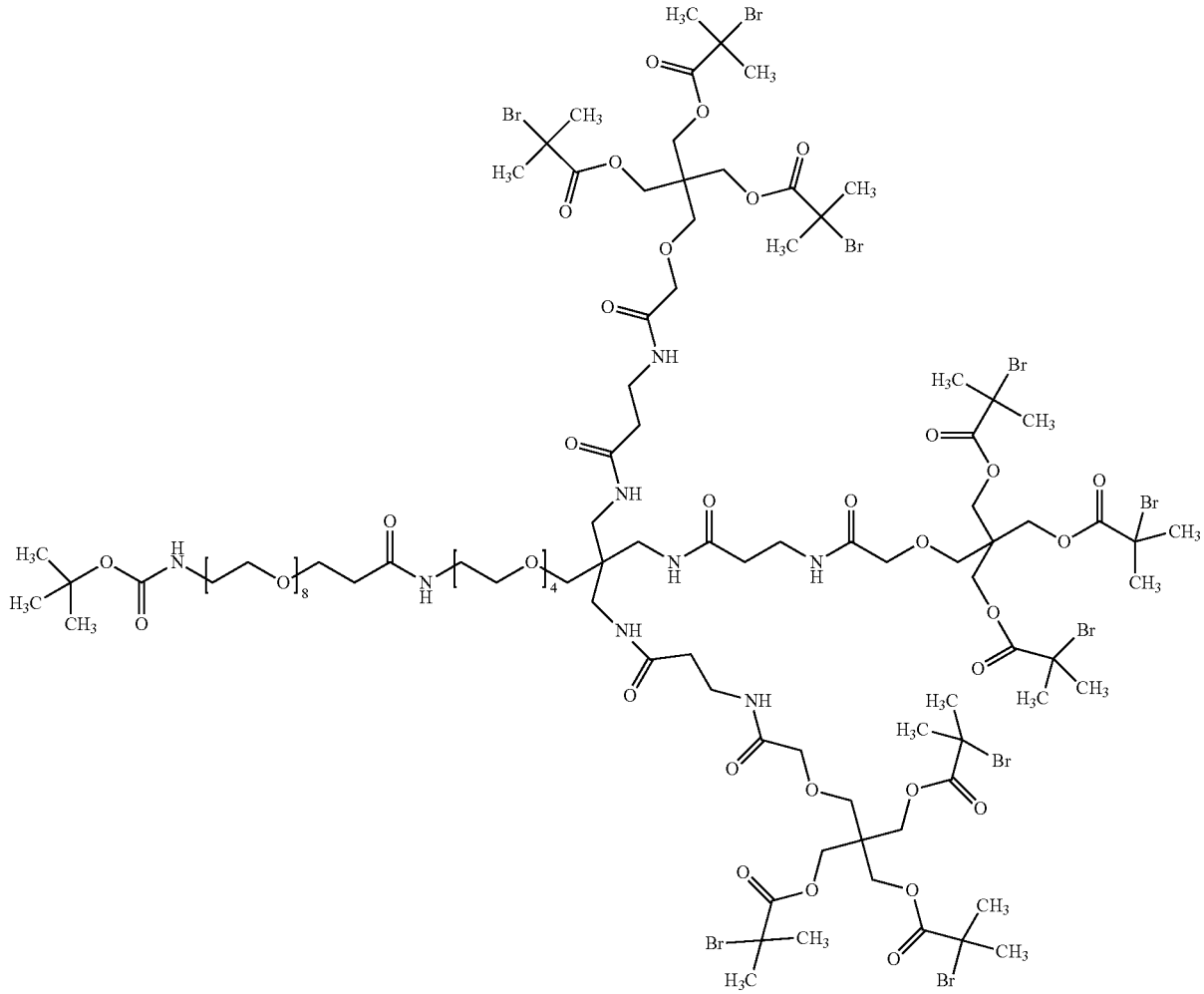

into a 20 mL vial was placed Compound L (410 mg, 0.164 mmol, 1.0 equiv) (see above) and alpha-t-butyloxycarbonylamino-omega-carboxy octa(ethylene glycol) (97.5 mg, 0.18 mmol, 1.1 equiv) followed by N,N-dimethylformamide (2 mL) then N,N-diisopropylethylamine (0.171 mL, 0.982 mmol, 6 equiv). The flask was cooled to 0° C. using an ice bath. To this was added propylphosphonic anhydride solution (50 wt. % in ethyl acetate, 0.205 mL, 0.327 mmol, 2 equiv) over ~1 minutes. The reaction was warmed to room temperature and stirred for 30 minutes. The reaction was quenched by adding water (10 mL), saturated aqueous sodium bicarbonate (10 mL) and ethyl acetate (40 mL). The organic layer was separated and the aqueous layer extracted with ethyl acetate (25 mL). The combined organic layers were washed with saturated aqueous sodium bicarbonate (10 mL), 0.5 M aqueous citric acid (10 mL), water (10 mL), and saturated aqueous sodium chloride (10 mL), then dried (sodium sulfate), filtered and concentrated under vacuum. The residue which was used without further purification resulted in 0.5 g (0.172 mmol, 105%) of Compound M.

LC-MS (ES, m/z): [(M+2H-boc)/2]+ Calcd for (C103H173Br9N8O42+2H-Boc)/2=1408.2; Found 1408.9.

Into a 100 mL round bottom under nitrogen was added Compound M (0.5 g), dichloromethane (4 mL) followed by trifluoroacetic acid (3 mL). The reaction stirred at room temperature for 15 minutes. The reaction was concentrated under a vacuum. The residue was dissolved using acetonitrile (3 mL), filtered through a syringe filter (Acrodisc CR25, PN 4225T) and loaded onto a preparatory HPLC column and eluted with 50% acetonitrile (with 0.1% trifluoroacetic acid) in 50% water (with 0.1% trifluoroacetic acid) up to 90% acetonitrile (with 0.1% trifluoroacetic acid). The tubes containing product were pooled, concentrated under vacuum, frozen and placed on a lyophilizer. This resulted in 101 mgs (21% over 2 steps) Compound O.

1H NMR (400 MHz DMSO-d6): δ=1.90 (s, 54H, CC(CH3)2Br). 2.3 (br t, 8H, CCH2CH2NH and CH2CH2C=O), 3.0 (m, 8H, CCH2NH and OCH2CH2 NH), 3.1-3.6 (m, 64H, OCH2C), 3.87 (s, 6H, O=CCH2O), 4.27 (s, 18H, CCH2OC=O), 7.6-7.8 (m, 10H, both CH2NHC=Q and NH3+).

LC-MS (ES, m/z): [(M+2H)/2]+ Calcd for (C98H165Br9N8O40+2H)/2=1408.2; Found 1408.3.

Example 5. Preparation of Longer Spacer 9-Arm "Snap-On" Initiator Compound P

A TFA/amine salt initiator (Compound P) having the structure below was synthesized as follows:

Compound P

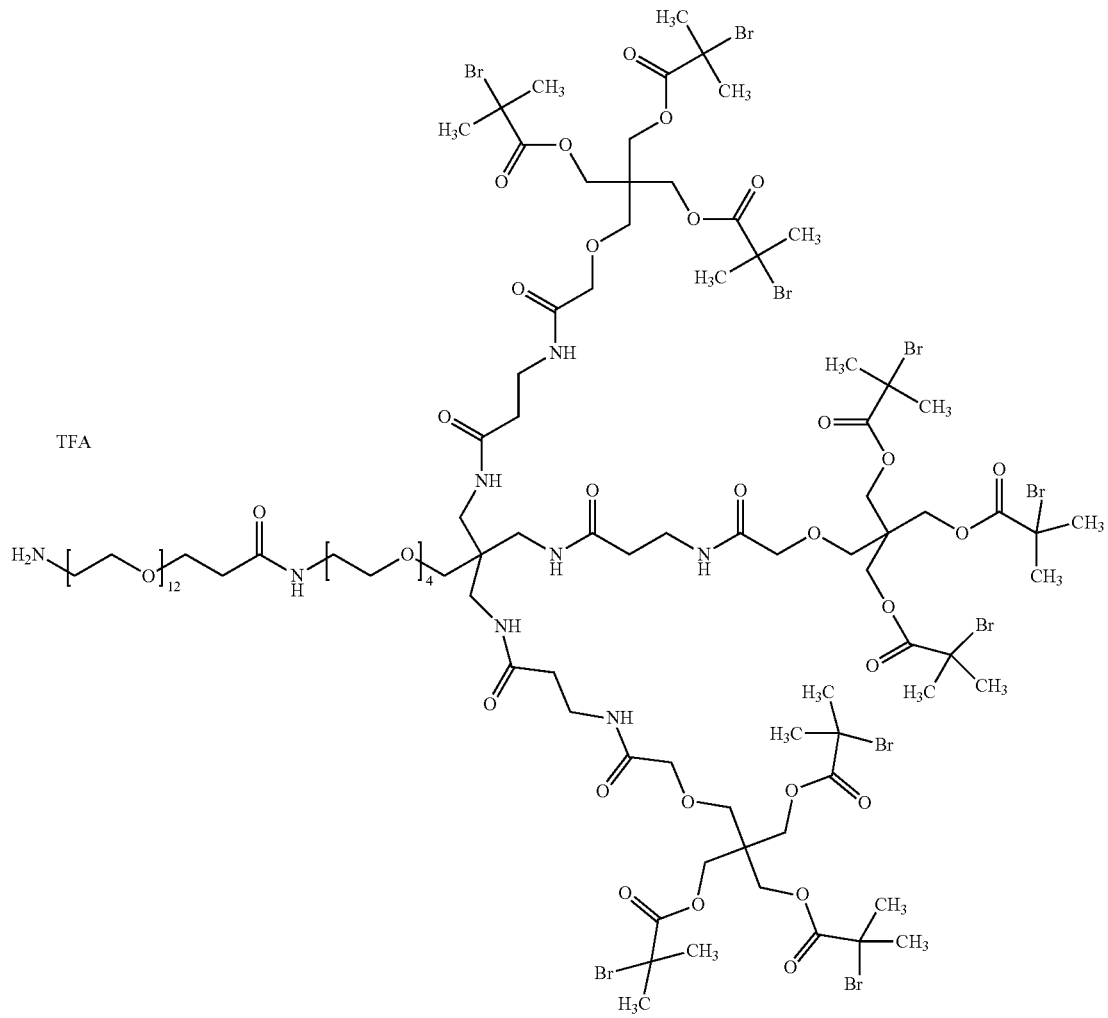

into a 20 mL vial was placed Compound L (430 mg, 0.172 mmol, 1.0 equiv) (see above) and alpha-t-Butyloxycarbonylamino-omega-carboxy dodeca(ethylene glycol) (154 mg, 0.215 mmol, 1.25 equiv) followed by N,N-dimethylformamide (2 mL) then N,N-diisopropylethylamine (0.18 mL, 1.03 mmol, 6 equiv). The flask was cooled to 0° C. using an ice bath. To this was added propylphosphonic anhydride solution (50 wt. % in ethyl acetate, 0.215 mL, 0.343 mmol, 2 equiv) over 1 minute. The reaction was warmed to room temperature and stirred for 30 minutes. The reaction was quenched by adding water, saturated aqueous sodium bicarbonate and ethyl acetate. The organic layer was separated and the aqueous layer extracted with ethyl acetate. The combined organic layers were washed with saturated aqueous sodium bicarbonate, 0.5 M aqueous citric acid, water, and saturated aqueous sodium chloride, then dried (sodium sulfate), filtered and concentrated under vacuum. The residue which was used without further purification resulted in 0.6 g (0.194 mmol) of Compound N, shown below.

LC-MS (ES, m/z): [(M+2H-boc)/2]+ Calcd for $(C_{111}H_{189}Br_9N_8O_{46}+2H-Boc)/2=1496.3$; Found 1497.2.

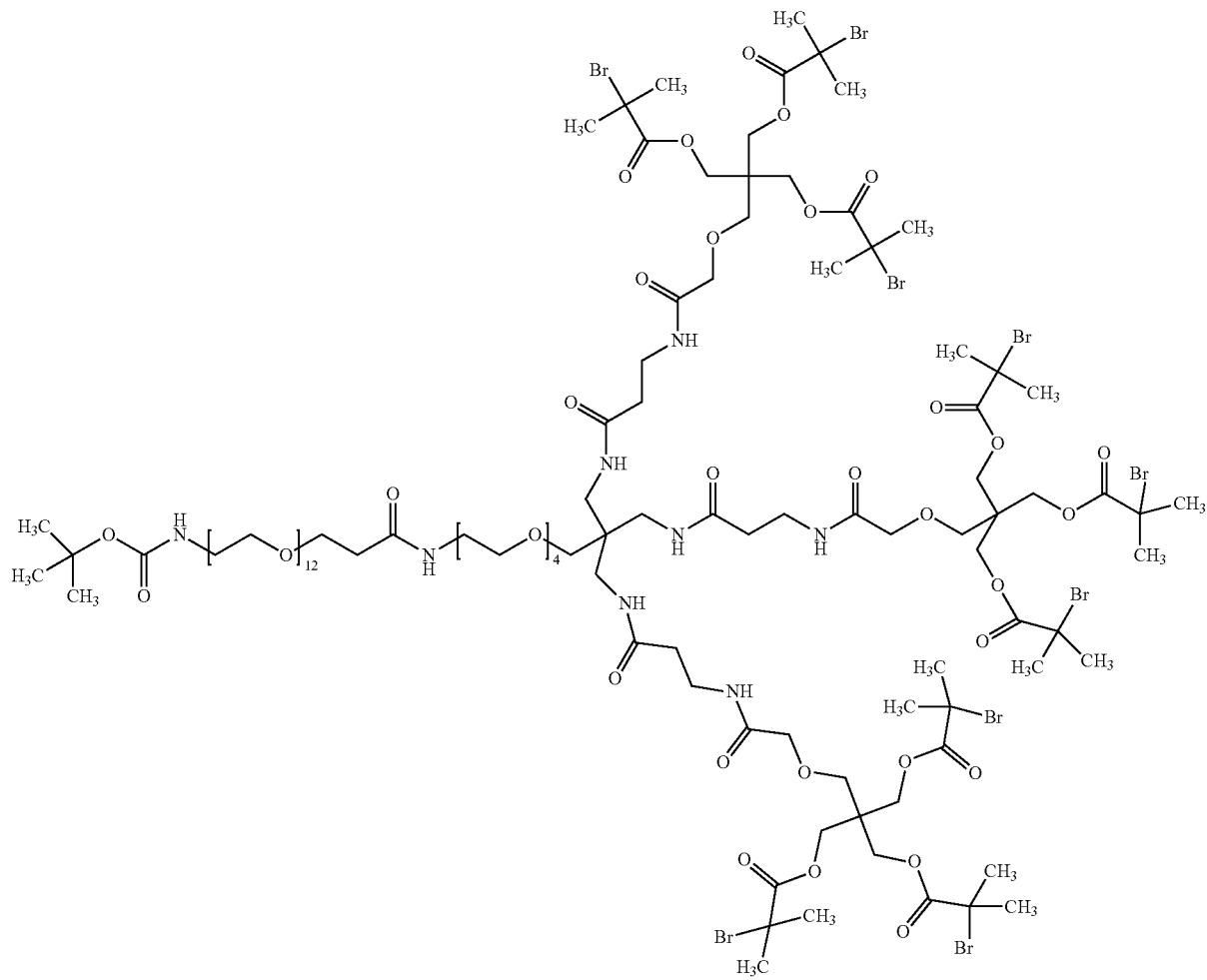

Compound N into a 100 mL round bottom under nitrogen was added Compound N (0.6 g), dichloromethane (4 mL) followed by trifluoroacetic acid (3 mL). The reaction stirred at room temperature for 15 minutes. The reaction was concentrated under a vacuum. The residue was dissolved using acetonitrile (3 mL), filtered through a syringe filter (Acrodisc CR25, PN 4225T) and loaded onto a preparatory HPLC column and eluted with 50% acetonitrile (with 0.1% trifluoroacetic acid) in 50% water (with 0.1% trifluoroacetic acid) up to 90% acetonitrile (with 0.1% trifluoroacetic acid). The tubes containing product were pooled, concentrated under vacuum, frozen and placed on a lyophilizer. This resulted in 200 mgs (0.064 mmol, 37% over 2 steps) Compound P.

1H NMR (400 MHz DMSO-d6): δ=1.90 (s, 54H, CC(CH3)2Br), 2.3 (br t, 8H, CCH2CH2NH and CH2CH2C=O), 3.0 (m, 8H, CCH2NH and OCH2CH2NH), 3.1-3.6 (m, 84H, OCH2C), 3.87 (s, 6H, O=CCH2O), 4.27 (s, 18H, CCH2OC=O), 7.6-7.8 (m, 10H, both CH2NHC=O and NH3+).

LC-MS (ES, m/z): [(M+2H)/2]+ Calcd for (C106H181Br9N8O44+2H)/2=1496.3; Found 1496.6.

Synthesis of Polymers

Example 6. Preparation of Zwitterionic Polymers

Initiator is typically prepared as a stock solution in DMF of about 100 mg/mL The initiator and the ligand (2,2'-bipyridyl) were introduced into a Schlenk tube. The resultant solution was cooled to −78° C. using a dry ice/acetone mixture, and was degassed under vacuum for 10 min. The tube was refilled under Argon and the catalyst (CuBr unless otherwise indicated), kept under Argon, was introduced into the Schlenck tube (the Molar ratio of atom bromine on the initiator/catalyst (CuBr)/ligand was kept at 1/1/2). The solution became dark brown immediately. The Schlenk tube was sealed and immediately purged by applying a short cycle vacuum/Argon. A solution of HEMA-PC was prepared by mixing a defined quantity of monomer, prepared in a glovebox kept under nitrogen, with 200 proof degassed ethanol. The monomer solution was added drop wise into the Schlenk tube (via canula) (and homogenized by light stirring: unnecessary). The temperature was maintained at −78° C. A thorough vacuum was applied to the reaction mixture for at least 10 to 15 min. until bubbling from the solution ceased. The tube was then refilled with Argon and warmed to room temperature. The solution was stirred, and as the polymerization proceeded, the solution became viscous. After 3 to 8 hours or just left overnight, the reaction was quenched by direct exposure to air in order to oxidize Cu (I) to Cu (II), the mixture became blue-green in color, and was passed through a silica column in order to remove the copper catalyst. The collected solution was concentrated by rotary evaporation and the resulting mixture was either precipitated with tetrahydrofuran or dialyzed against water followed by freeze drying to yield a free-flowing white powder. Table 2 sets forth exemplary polymers made in accordance with the present invention.

TABLE 2

| Theor. MW (kDa) | Polymer ID No. | Initiator (see Table 3) | Mn (kDa) | Mp (kDa) | PDI |
|---|---|---|---|---|---|
| 150 [w2199] [d2191] | 60 | B5 | 150 | 158 | 1.05 |
| 250 [wR2765] [dR2731] | 70 | B4 | 205 | 230 | 1.05 |
| 250 [wR3350] [dR3324] | 80 | B5 | 117 | 137 | 1.1 |
| 250 [wR3373] [dR3372] | 90 | B6 | 235 | 258 | 1.1 |
| 250 [wR3460I] [wR3461M] [dR3418] | 100 | B | 242 | 259 | 1.1 |

TABLE 2-continued

| Theor. MW (kDa) | Polymer ID No. | Initiator (see Table 3) | Mn (kDa) | Mp (kDa) | PDI |
|---|---|---|---|---|---|
| 250 [wR3482I] [wR3483M] [dR3463] | 110 | F1 | 245 | 270 | 1.1 |
| 500 [wR3763] [dR3662] | 120 | F1 | 490 | 557 | 1.1 |
| 500 [wR3758] [dR3706] | 130 | L | 490 | 530 | 1.1 |
| 750 [wR3764] [dR3667] | 140 | F1 | 586 | 695 | 1.1 |
| 750 [wR3759] [dR3707] | 150 | L | 645 | 750 | 1.1 |
| 750 [wR3836] [dR3804] | 160 | O | 656 | 740 | 1.1 |
| 750 [wR3835] [dR3808] | 170 | P | 785 | 900 | 1.1 |

TABLE 3

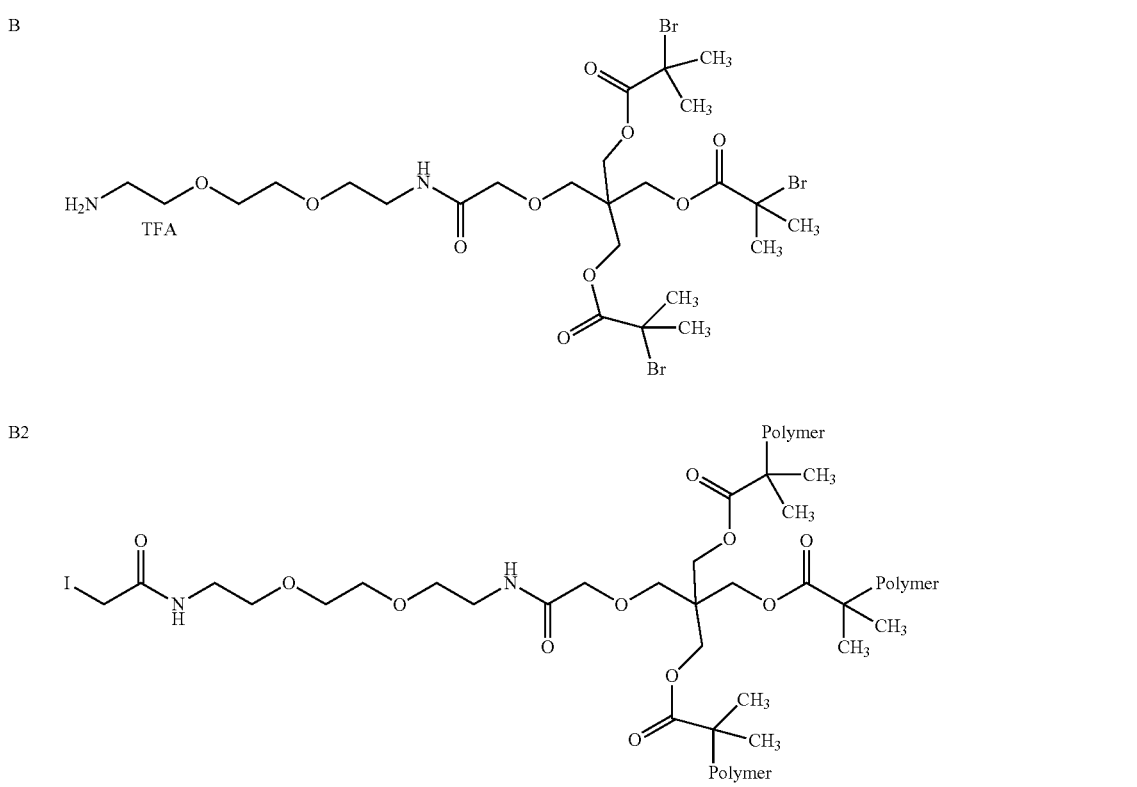

TABLE 3-continued
B3
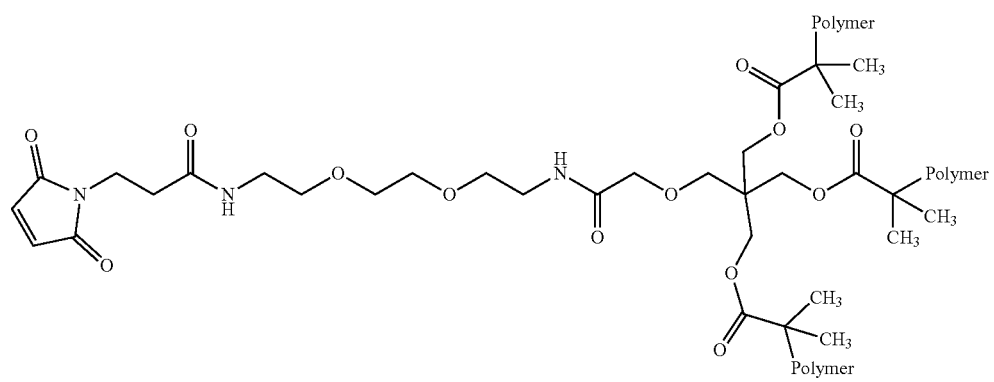
B4
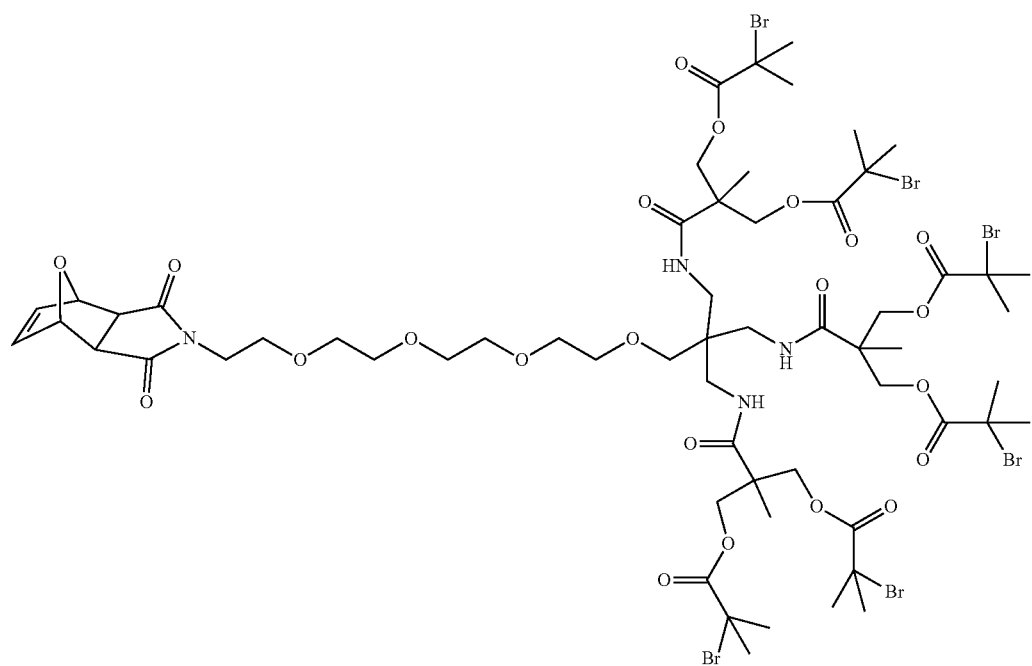 [SMILES: CC(C)(Br)C(=O)OCC(C)(COC(=O)C(C)(C)Br)C(=O)NCC(CNC(=O)C(C)(COC(=O)C(C)(C)Br)COC(=O)C(C)(C)Br)(CNC(=O)C(C)(COC(=O)C(C)(C)Br)COC(=O)C(C)(C)Br)COCCOCCOCCOCCN1C(=O)C2C3C=CC(O3)C2C1=O]
B5
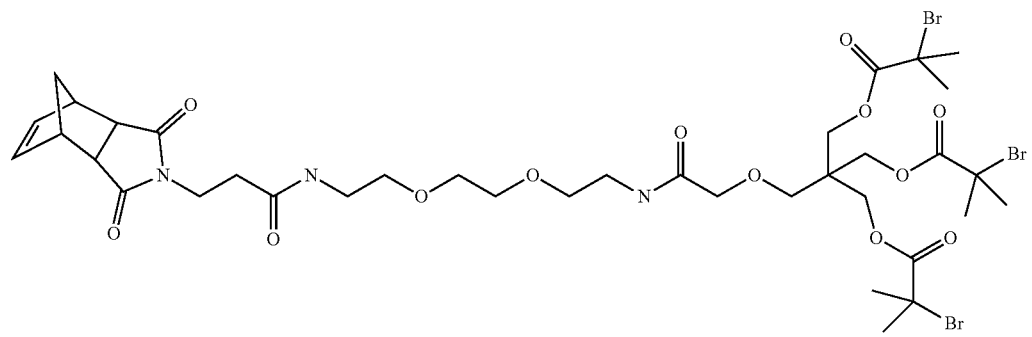 [SMILES: CC(C)(Br)C(=O)OCC(COCC(=O)NCCOCCOCCNC(=O)CCN1C(=O)C2C3C=CC(C3)C2C1=O)(COC(=O)C(C)(C)Br)COC(=O)C(C)(C)Br]
B6
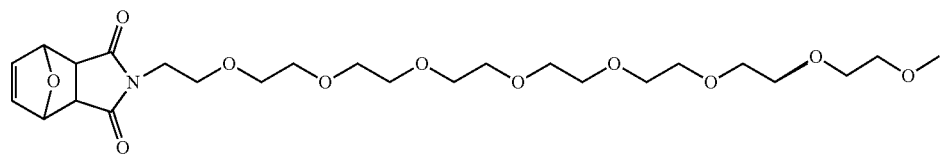

TABLE 3-continued
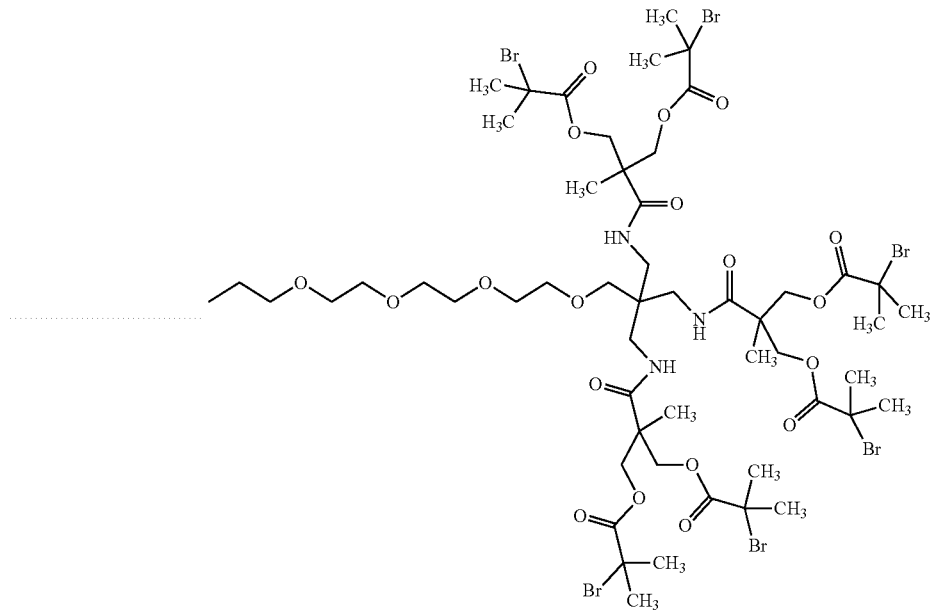
F1
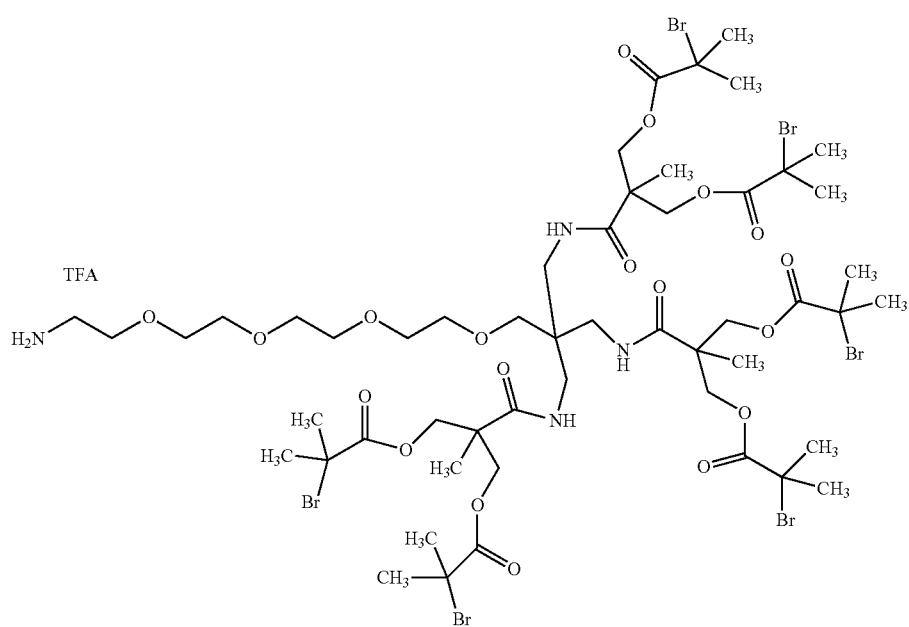 [SMILES: CC(C)(Br)C(=O)OCC(C)(COC(=O)C(C)(C)Br)C(=O)NCC(CNC(=O)C(C)(COC(=O)C(C)(C)Br)COC(=O)C(C)(C)Br)(CNC(=O)C(C)(COC(=O)C(C)(C)Br)COC(=O)C(C)(C)Br)COCCOCCOCCOCCN]

TABLE 3-continued
L
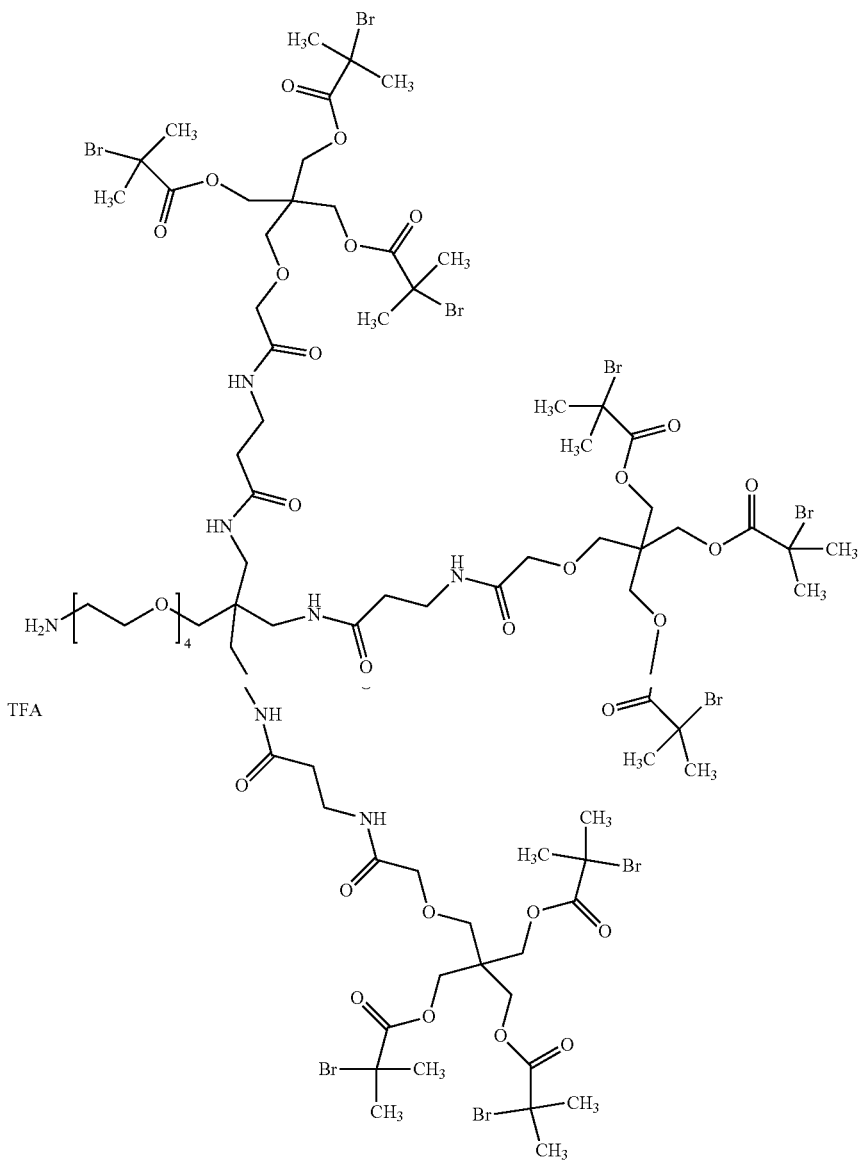
TFA

TABLE 3-continued
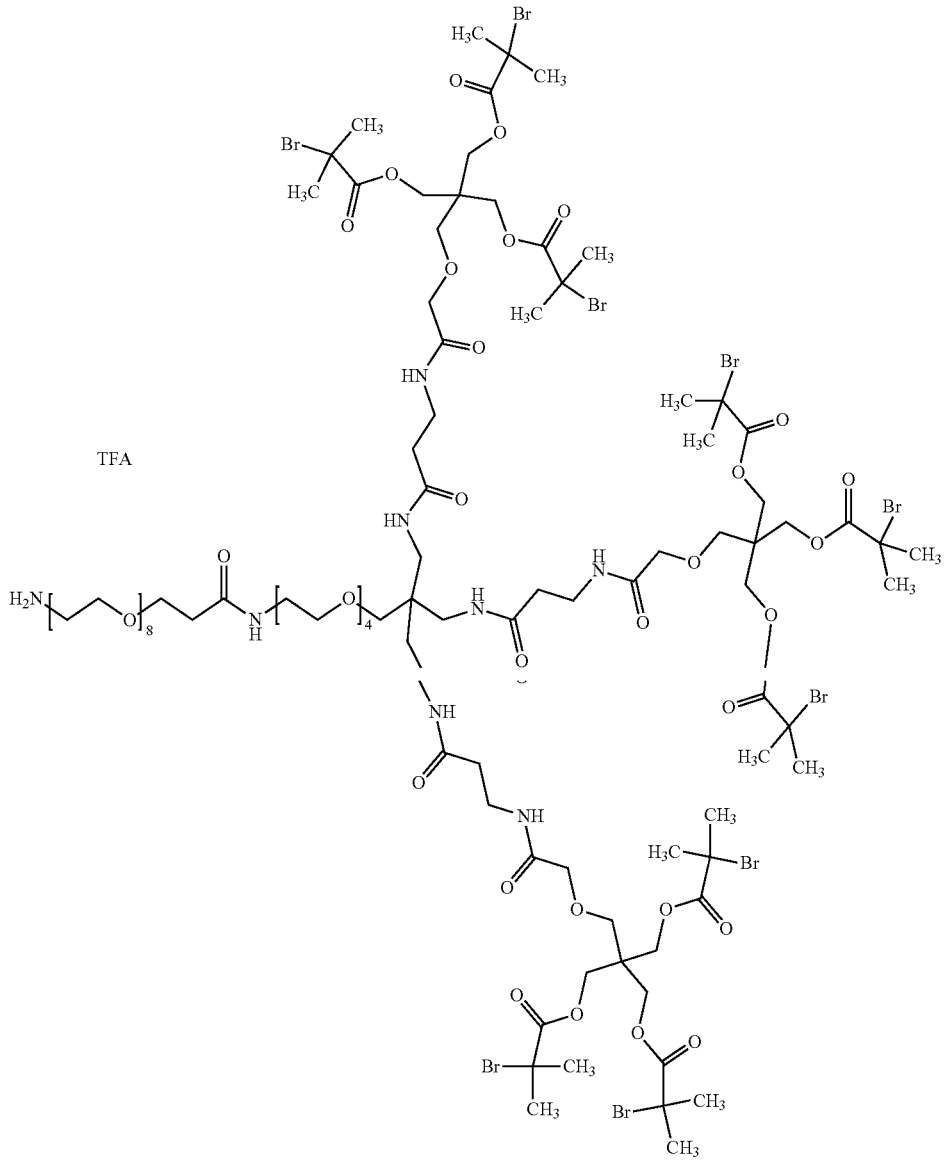

TABLE 3-continued

P

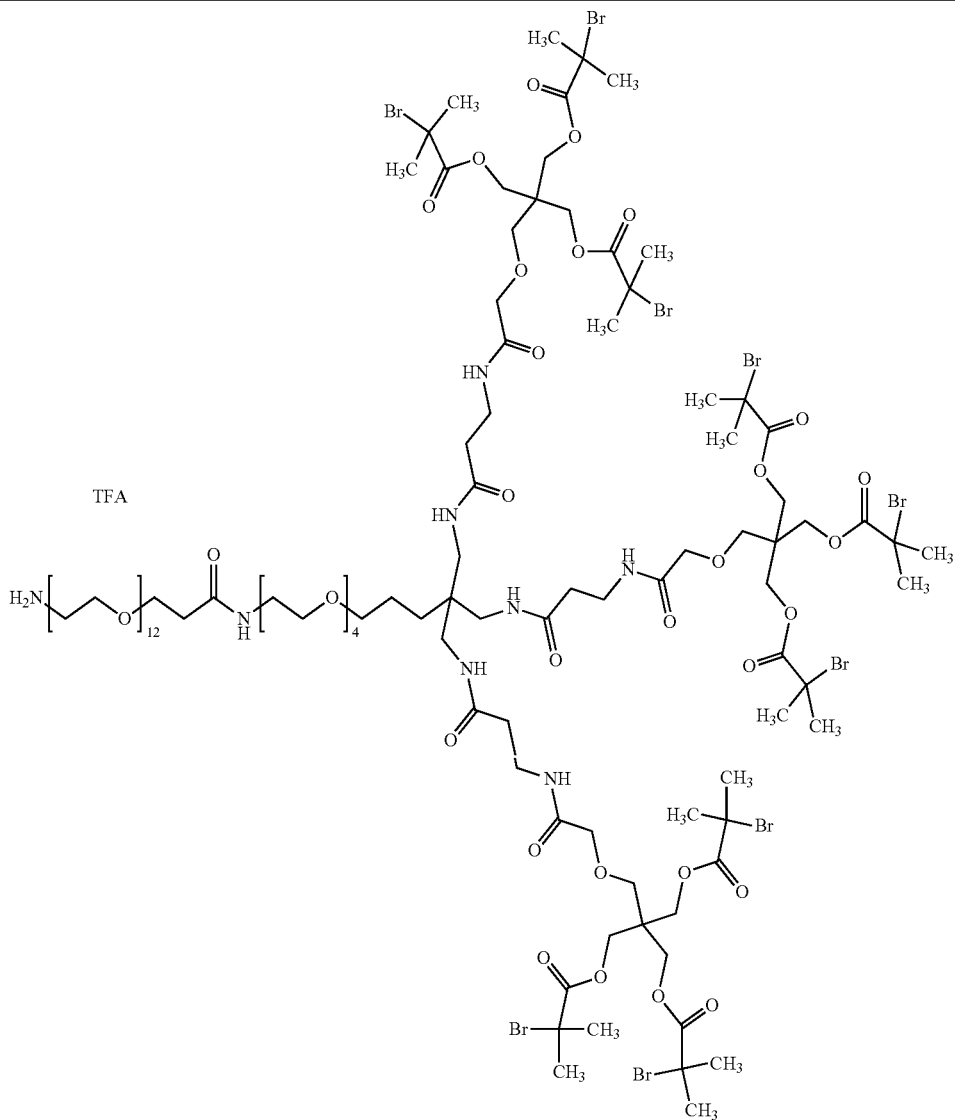

Example 7. Deprotection of Protected Maleimide

It was observed that the protected maleimide biopolymers tend to shift the Mp to higher values after heat de-protection when the biopolymer powder was heated at 120° C. for 90 minutes. This makes the biopolymer manufacturing more challenging since the amount of up-shift in Mp depended on the biopolymer (Mp, architecture, etc). An alternative method of deprotection is needed.

Initial experimentation was carried out in water in a sealed capillary loop. It was demonstrated that furan was released during heat deprotection of aqueous biopolymer solution in an oven at 120° C. No up-shift in Mp was observed after the heat deprotection in aqueous solution.

The procedure was also repeated for biopolymers dissolved in ethanol. It was confirmed that the Mp up-shift was completely eliminated when the heat deprotection was carried out in ethanol solution. Different heating methods such as an oven or an oil bath were tested and little difference was found as long as the heating time and temperatures were kept the same. The duration of heating has to be optimized to avoid biopolymer degradation but at the same time ensuring deprotection of most of the furan protected maleimide biopolymers. The procedure was finalized to use an ethanol solution of the biopolymers in a pressure reactor (able to hold 70 PSI pressure).

Typical operation starts with a clean and dry glass reactor. The biopolymer is dissolved in ethanol to form a clear and transparent solution. The concentration of the biopolymer is typically between 50 mg/mL to 150 mg/mL, with around 100 mg/mL most often. This is a good balance between minimizing the ethanol to be consumed and avoiding high viscosity of the polymer solution.

The clear biopolymer solution should be transferred to a clean pressure reactor, purged with $N_2$ for 3 to 5 minutes, and then tightly capped. The mass of the reactor plus the biopolymer solution should be logged before and after the heat deprotection so any leak can be identified.

The pressure reactor containing the biopolymer (to be deprotected) solution is placed in an oven set at 120° C. for two hours. After the deprotection, the pressure reactor is taken out of the oven and allowed to cool down. The deprotected biopolymer solution can be purified by solvent precipitation, spray-drying, or lyophilization.

Preparation of Conjugatable Polymers

Example 8. Preparation of Maleimide Conjugatable 3-Arm Polymer

A maleimide conjugatable polymer (B3) having the following structure was prepared as follows:

tube placed into centrifuge (rpm 3000) for 30 minutes. The filtrate is removed for analysis while the retentate is diluted and mixed with 4:1 water:tertahydrofuran (6 mL) and the tube placed into centrifuge (rpm 3000) for 30 minutes. The filtrate is removed for analysis while the retentate is diluted and mixed with water (8 mL), placed into centrifuge (rpm 3000) for 30 minutes. The filtrate is removed for analysis while the retentate is diluted and mixed with water (8 mL). The centrifuge procedure repeated 3 more times, after which the retentate is removed and placed into a vial. The Amicon membrane tube was rinsed with water (2×~2 mL) and this

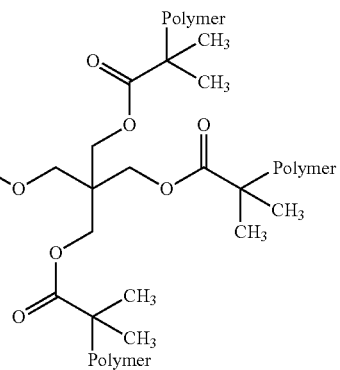

B3 into a 20 mL vial was placed Polymer ID No. 100 (Table 2) (280 mg, 0.00123 mmol, 1.0 equiv) and dissolved using water (2 mL). To this was added 0.5 M aqueous sodium phosphate dibasic (0.2 mL). In a separate vial was dissolved 3-maleimidopropionic acid, NHS ester (1.5 mg, 0.00548 mmol, 4.5 equiv) in tetrahydrofuran (0.6 mL). The NHS ester solution was added to the polymer solution over ~2 minutes at room temperature and the resulting solution was stirred for 75 minutes. The reaction was diluted with 4:1 water:tertahydrofuran (4 mL) and placed into a Amicon centrifuge membrane dialysis tube (30,000 mwco) and the combined with the retentate, which was frozen and placed on a lyophilizer. This resulted in 262 mgs (93%) B3 as a white powder.

Example 9. Preparation of Maleimide 6-Arm Conjugatable Polymer

A maleimide conjugatable 6-arm polymer (F4) having the following structure was synthesized as follows:

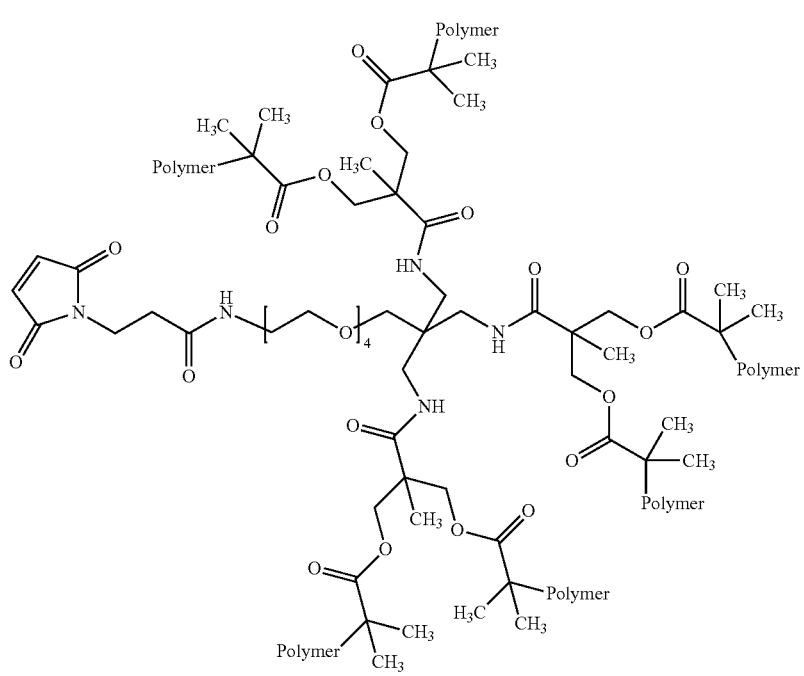

F4 into a 20 mL vial was placed Polymer ID No. 110 (Table 2) (502 mg, 0.00205 mmol, 1.0 equiv) and dissolved using water (4 mL). To this was added 0.5 M aqueous sodium phosphate dibasic (0.4 mL). In a separate vial was dissolved 3-maleimidopropionic acid, NHS ester (2.45 mg, 0.0092 mmol, 4.5 equiv) in tetrahydrofuran (1 mL). The NHS ester solution was added to the polymer solution over 2 minutes at room temperature and the resulting solution was stirred for 100 minutes. The reaction was diluted with 4:1 water:tertahydrofuran (4 mL) and placed evenly into 2 Amicon centrifuge membrane dialysis tubes (30,000 mwco) and the tubes placed into centrifuge (rpm 3000) for 30 minutes. The filtrate is removed for analysis while the retentate is diluted and mixed with 4:1 watentertahydrofuran (6 mL) and the tubes placed into centrifuge (rpm 3000) for 30 minutes. The filtrate is removed for analysis while the retentate is diluted and mixed with water (8 mL each), placed into centrifuge (rpm 3000) for 30 minutes. The filtrate is removed for analysis while the retentate is diluted and mixed with water (8 mL/tube). The centrifuge procedure repeated 3 more times, after which the retentate is removed and placed into a vial. The Amicon membrane tubes were rinsed with water (2×~2 mL each tube) and this combined with the retentate was frozen and placed on a lyophilizer. This resulted in 459 mgs (91%) Polymer F4 as a white powder.

Example 10. Preparation of 6-Arm Conjugatable Polymer

A maleimide conjugatable 6-arm polymer (S) having the following structure was synthesized as follows:

into a 20 mL vial was placed Polymer ID No. 120 (Table 2) (500 mg, 0.00091 mmol, 1.0 equiv) and dissolved using ethanol (4 mL) after stirring for 10 minutes. To this was added a 1% solution of 4-methylmorpholine in acetonitrile (0.030 mL, 0.00273 mmol, 3 equiv). In a separate vial was dissolved Product 176-55 (2.65 mg, 0.00455 mmol, 5 equiv) in acetonitrile (1 mL) and this solution was added to the polymer solution over ~1 minute at room temperature. An additional aliquot of acetonitrile (1 mL) was added and the resulting solution was stirred for 18 hours. The reaction was diluted with 0.1% aqueous trifluoroacetic acid (2 mL) (pH~6) followed by water (~14 mL), filtered through a syringe filter (Acrodisc Supor, PN 4612) and placed evenly into 3 Amicon centrifuge membrane dialysis tubes (30,000 mwco). The tubes were diluted and mixed with water (~5 mL each), placed into centrifuge (rpm 3000) for 30 minutes. The filtrate is removed for analysis while the retentate is diluted and mixed with water (~10 mL/tube). The centrifuge procedure repeated 5 more times, after which the retentate is removed and placed into a vial. The Amicon membrane tubes were rinsed with water (2×~2 mL each tube) and this combined with the retentate. The retentate solution was filtered through a syringe filter (Acrodisc Supor, PN 4612), frozen and placed on a lyophilizer. This resulted in 469 mgs (0.00085 mmol, 93%) Polymer S as a white powder.

Example 11. Preparation of Maleimide 9-Arm Conjugatable Polymer

A maleimide conjugatable 9-arm polymer (Q) having the following structure was synthesized as follows:

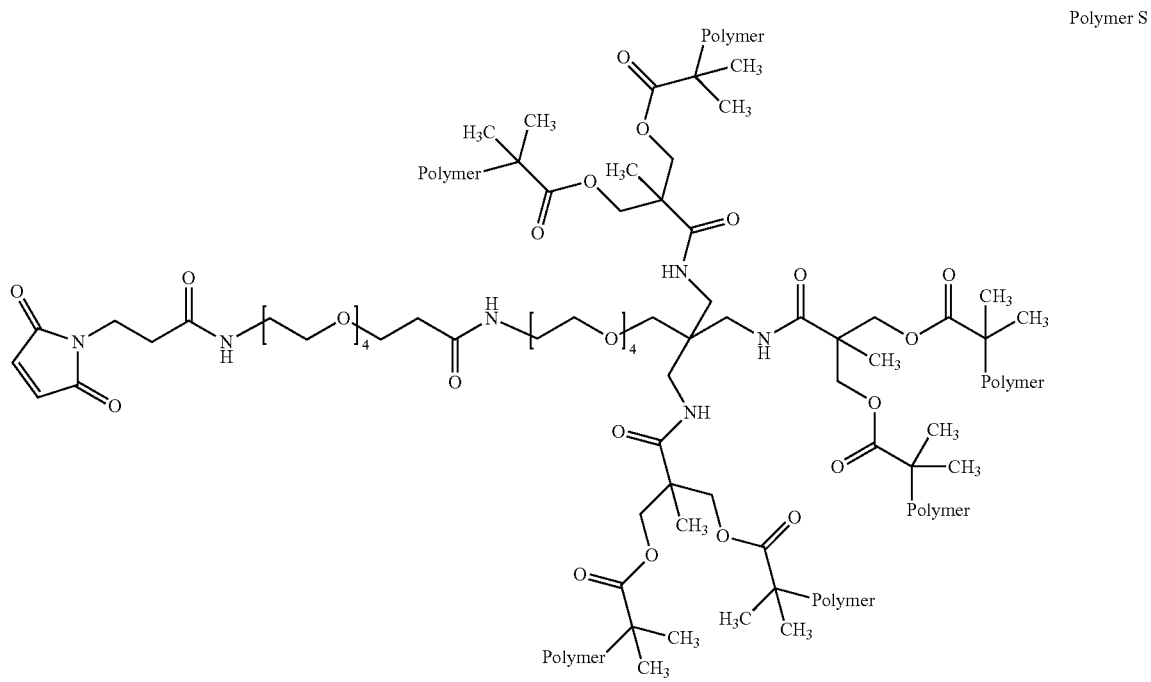

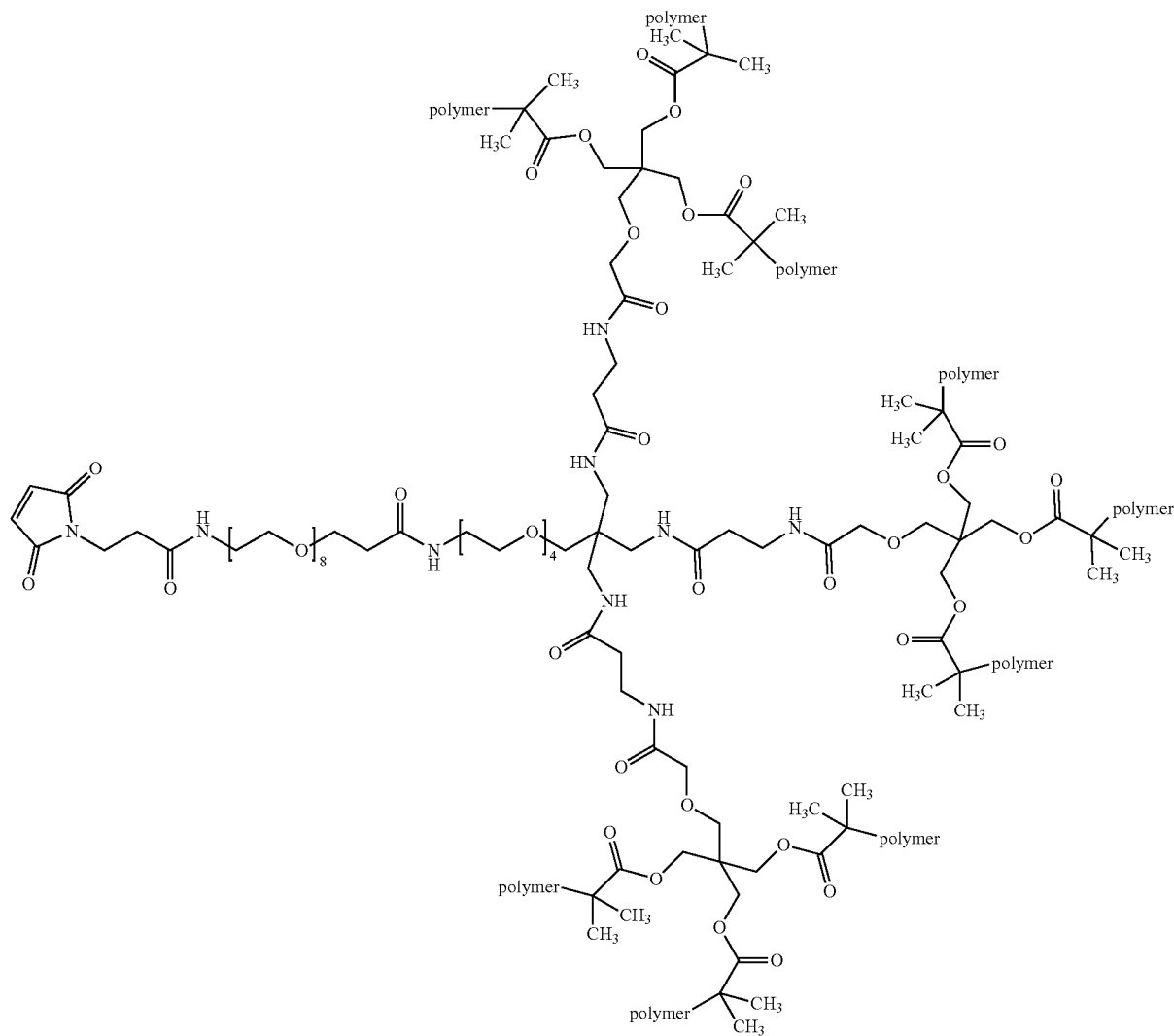

Polymer Q conjugateable polymer Q was prepared as follows: into a 20 mL vial was placed Polymer ID No. 160 (Table 2) (540 mg, 0.0007 mmol, 1.0 equiv) and dissolved using water (4 mL). To this was added 0.5 M aqueous sodium phosphate dibasic (0.4 mL). In a separate vial was dissolved 3-maleimidopropionic acid, NHS ester (0.93 mg, 0.0035 mmol, 5 equiv) in tetrahydrofuran (1 mL). The NHS ester solution was added to the polymer solution over ~2 minutes at room temperature and the resulting solution was stirred for 30 minutes. The reaction was diluted with water (~15 mL), filtered through a syringe filter (Acrodisc Supor, PN 4612) and placed evenly into 3 Amicon centrifuge membrane dialysis tubes (30,000 mwco). The tubes were diluted and mixed with water (~5 mL each), placed into centrifuge (rpm 3000) for 30 minutes. The filtrate is removed for analysis while the retentate is diluted and mixed with water (~10 mL/tube). The centrifuge procedure repeated 5 more times, after which the retentate is removed and placed into a vial. The Amicon membrane tubes were rinsed with water (2×~2 mL each tube) and this combined with the retentate. The retentate solution was filtered through a syringe filter (Acrodisc Supor, PN 4612), frozen and placed on a lyophilizer. This resulted in 508 mgs (94%) Polymer Q as a white powder.

Example 12. Preparation of Maleimide 9-Arm Conjugatable Polymer

A maleimide conjugatable 9-arm polymer (R) having the following structure was synthesized as follows:

Polymer R

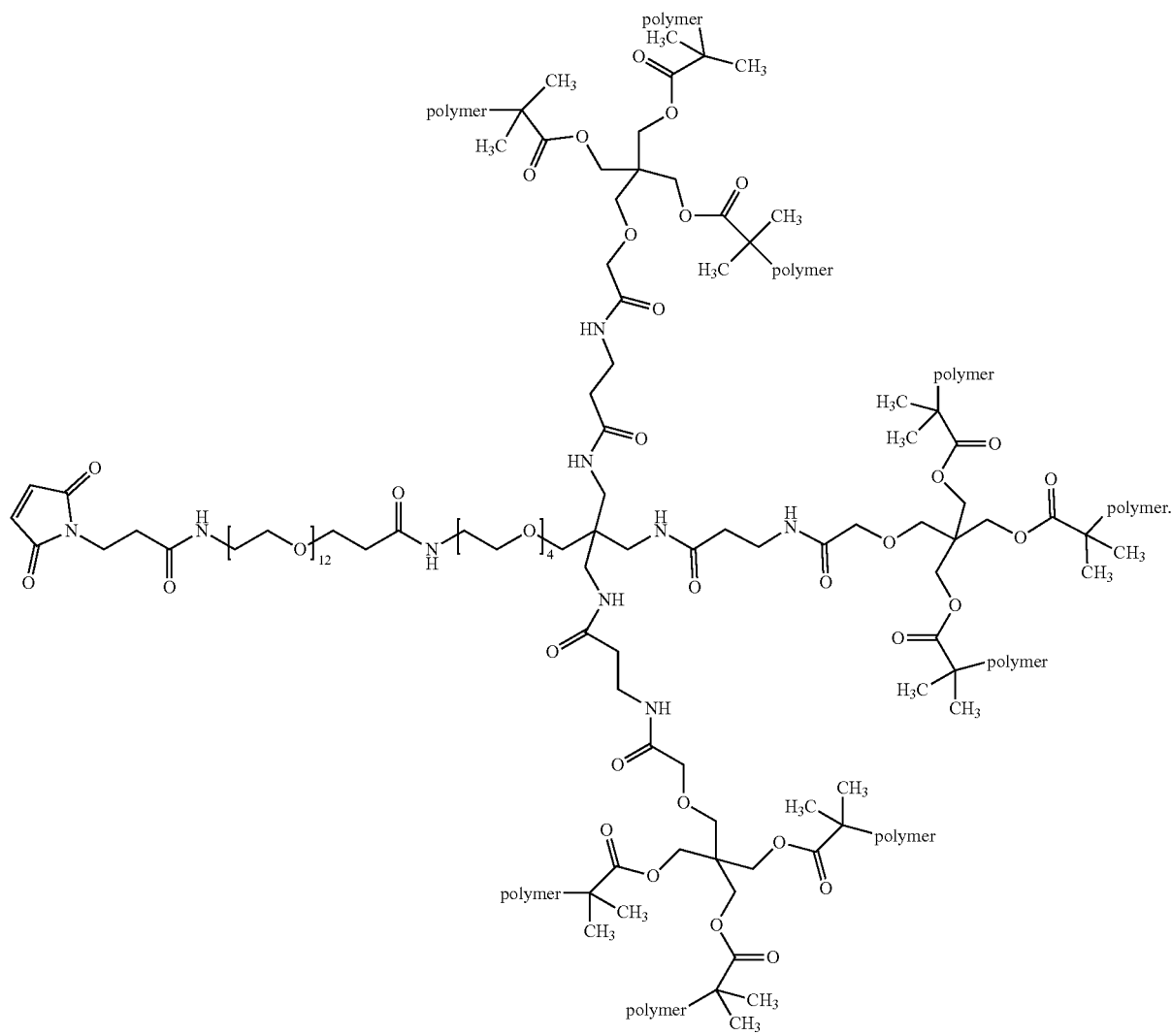

It was prepared using the same techniques as describe for Conjugateable polymer Q.

Example 13. Preparation of Wild-Type Factor VII for Conjugation

Mammalian expressed wild-type (FVIII-WT) is known to have all cysteine residues either oxidized to form disulfide linkages or, in the case of the free cysteines present in the B domain, blocked (capped) by metabolites from the media that prevent unpaired free cysteines from being available for conjugation using thiol-reactive polymers containing reactive groups such as maleimide or iodoacetamide. These capping moieties can be removed using reducing agents such as TCEP or DTT followed by removal of the reducing agent and protein refolding.

FVIII-WT was formulated into 50 mM MOPS pH7, 10 mM $CaCl_2$, 200 mM NaCl, 1% sucrose and 0.01% Tween80 at a concentration of 0.5 mg/mL. A 150× molar excess equivalent of TCEP solution was added and incubated at 4° C. for 1 hour. A desalting column of Sephadex G25 was used for TCEP removal. The G25 column was equilibrated with the formulation buffer and the TCEP reduced sample was loaded, and fractions collected were analyzed by SDS-PAGE. The fractions containing protein were pooled and incubated at 4° C. overnight to allow protein refolding (regeneration of disulfide pairs by oxidation), while unpaired cysteine remained in free sulfhydryl form (decapped). Alternatively, the TCEP removal was accomplished using an anion exchange (e.g. Q Sepharose FF) column where the TCEP reduced sample was diluted to lower the salt concentration and then loaded onto the QFF column, followed by a washing step using the low salt MOPS buffer and elution with a step gradient of NaCl. Under these conditions, the protein eluted at around 300 mM NaCl. The protein fractions were pooled for conjugation as described below. The ion exchange method for TCEP removal is preferred over the desalting column approach as it is more amenable to scale up.

The analysis of the TCEP treated form by SDS-PAGE analysis showed predominantly two bands: (1) a higher MW band migrating at around 180 kDa which represents the heavy chain plus B domain (HC-BD); and (2) a lower MW band migrating at about 80 kDa which represents the light chain (LC). The sample was also analyzed by gel filtration using a Superose 6 column. The column was equilibrated in 20 mM Tris pH7.5, 10 mM $CaCl_2$, 200 mM NaCl, 10% ethanol, 1% sucrose and 0.001% Tween80 followed by injecting different FVIII samples including: (1) TCEP treated and refolded FVIII-WT; and (2) original FVIII-WT for comparison. The elution profile of both samples at 280 nm each showed a predominant single peak at the expected retention time.

Example 14. Conjugation of FVIII-WT to High Molecular Weight Zwitterionic Polymers The unveiled free cysteine thiol in the TCEP treated form of FVIII-WT was used for conjugation to a variety of maleimide and iodo-acetamide functionalized polymers from above, varying in molecular weight, architecture, and linker length as shown in Table 4. The conjugation reaction mixtures contained FVIII-WT protein at about 0.5 mg/mL in 50 mM MOPS pH7, 10 mM $CaCl_2$, 200 mM NaCl, 0.01% Tween80 and 5-100× molar excess of the maleimide polymer dissolved in 20 mM Tris pH8, 200 mM NaCl, 10 mM $CaCl_2$, and 0.01% Tween80. The reactions proceeded at 4° C. overnight followed by analysis of the conjugation efficiency by SDS-PAGE under both non-reducing and reducing conditions. The results showed the disappearance of a single heavy chain-B domain (HC-BD) band but not truncated forms of the domain and the concomitant appearance of a high molecular weight band at the top of the gel indicating the presence of newly formed conjugate. The conjugation efficiency (calculated as the percentage of the remaining HC—B domain band compared with the no polymer control) of each reaction is shown in Table 4.

TABLE 4

Conjugation of functionalized Polymers to WT FVIII

| No. | Init. (Table 2) | "Snap on" moiety | PDI | Mp (kD) | Polymer Molar Excess (x) | Conj. Effic.* |
|---|---|---|---|---|---|---|
| 1 | B4 | Non-heat deprotect | 1.041 | 226.9 | 5x | − |
| 2 | B5 | Non-heat deprotect | 1.089 | 240.5 | 10x | + to ++ |
| 3 | B6 | Non-heat deprotect | 1.085 | 255.4 | 10x | + to + |
| 4 | B | maleimide-propanoyl linker | 1.072 | 269.3 | 10x | ++ |
| 5 | Fl | maleimide-propanoyl linker | 1.075 | 266.5 | 10x | + |
| 6 | Fl | maleimide-propanoyl linker | 1.088 | 558.8 | 50x | + to ++ |
| 7 | Fl | maleimide-propanoyl linker | 1.102 | 696.9 | 50x | + to ++ |
| 8 | L | maleimide-propanoyl linker | 1.082 | 531.7 | 50x | + to ++ |

TABLE 4-continued

Conjugation of functionalized Polymers to WT FVIII

| No. | Init. (Table 2) | "Snap on" moiety | PDI | Mp (kD) | Polymer Molar Excess (x) | Conj. Effic.* |
|---|---|---|---|---|---|---|
| 9 | L | maleimide-CH2CH2-C(O)-CH3 | 1.098 | 768.3 | 50x | + to ++ |
| 10 | Fl | maleimide-CH2CH2-C(O)-CH3 | 1.088 | 552.8 | 50x | + |
| 11 | Fl | maleimide-CH2CH2-C(O)-CH3 | 1.102 | 696.9 | 50x | + |
| 12 | L | maleimide-CH2-C(O)-NH-(CH2CH2O)$_d$-C(O)-CH3 | 1.082 | 531.7 | 50x | + |
| 13 | L | maleimide-CH2CH2-C(O)-CH3 | 1.098 | 768.3 | 50x | + |
| 14 | B5 | Non-heat deprotect | 1.089 | 240.5 | 50x, 100x | ++++ ++++ |
| 15 | Fl | maleimide-CH2CH2-C(O)-CH3 | 1.102 | 696.9 | 50x | +++ ++++ |
| 16 | L | maleimide-CH2-C(O)-NH-(CH2CH2O)$_d$-C(O)-CH3 | 1.098 | 768.3 | 50x | ++ +++ |
| 17 | P | maleimide-CH2CH2-C(O)-CH3 | 1.095 | 769.3 | 50x | +++ ++++ |
| 18 | O | maleimide-CH2CH2-C(O)-CH3 | 1.119 | 749.5 | 50x 100x | +++ ++++ |

*++++ = excellent; +++ = good; ++ = fair; + = low; − = none or undetectable.

| QC3228 (Conjugate concentration by OD280 peak area of the conjugate) | | | | | | | | | | | |
|---|---|---|---|---|---|---|---|---|---|---|---|
| Conjugate name | Conc. (mg/ml) | Activity (IU/ml) | Specific activity (IU/mg) | QC# | Note | PDI | Mn (kD) | Mp (kD) | Mw (kD) | Polymer used | Initiator |
| QC3228_R4370 | 1.81 | 3260.3 | 1801.3 | QC3191 | WT-OG1706-conjugate | 1.070 | 1299 | 1296 | 1389 | OG1466 | O |
| QC3228_R3961 | 3.70 | 8758.4 | 2367.1 | QC3191 | WT-OG1502-conjugate | 1.052 | 1175 | 1171 | 1236 | OG1465 | P |
| FVIII parent proteins | | | | | | | | | | | |
| OG1297_R3971 | 0.2 | 597.5 | 2987.5 | QC3237 | WT-Original stock | 1.110 | 289 | 304 | 320 | | |
| Polymer used | | | | | | | | | | | |
| OG1466_R3836_mean | | | | | Mean = | 1.066 | 764 | 792 | 815 | | |
| OG1465_R3835_mean | | | | | Mean = | 1.097 | 676 | 774 | 741 | | |

A conjugation reaction was performed using 1 mg of TCEP-treated FVIII-WT and a 50× molar excess of the conjugatable polymer used in no. 17 (Table 4) and the protocol described previously. A conjugation efficiency of >90% was determined using SDS-PAGE as before. The conjugate band was maintained under reducing conditions.

The conjugate was purified using cation exchange chromatography using MacroCap SP resin. The conjugation reaction was diluted 10× into 50 mM MOPS, pH7, 10 mM CaCl$_2$, 0.01% Tween80 and loaded onto 3 mL resin packed into a 5 mL drip column. Column flow was achieved by gravity and the unbound fraction collected. The column was chased and washed with a combined 21 column volume (CV) of wash buffer containing 20 mM NaCl. The bound protein was then eluted with wash buffer containing varying NaCl concentrations including 100, 150, 200, 250 and 500 mM NaCl. At least 5 CV of elution was collected for each NaCl concentration. The fractions were subjected to SDS-PAGE analysis to determine at which NaCl concentration protein was eluted. Preliminary analysis indicated that free protein eluted at 150 mM salt, and the conjugate eluted at 100 mM salt. This was confirmed by analytical gel filtration on a Superose 6 column which gave single peaks for conjugate and free protein. The conjugate pool was concentrated and sterile filtered using a 0.2 μm SpinX centrifuge filter to yield a final concentration (as it relates to protein) of 2.16 mg/mL with a final process yield of 40%.

The activity of the conjugate, determined using the COAMATIC Factor FVIII assay kit, was equivalent to the FVIII-WT.

Although the foregoing invention has been described in some detail by way of illustration and example, for purposes of clarity of understanding, certain changes and modifications can be practiced within the scope of the appended claims. In addition, each reference provided herein is incorporated by reference in its entirety for all purposes to the same extent as if each reference was individually incorporated by reference. To the extent the content of any citation, including website or accession number may change with time, the version in effect at the filing date of this application is meant. Unless otherwise apparent from the context any step, element, aspect, feature of embodiment can be used in combination with any other.

What is claimed is:

1. A compound having the following formula:

R1-R2-(R3)$_s$;

wherein s is 1-20;

R1 is selected from the group consisting of —NH$_2$, —OH, and —SH;

R2 is selected from the group consisting of unsubstituted alkyl, unsubstituted alkylene, unsubstituted alkoxy, carboxyalkyl, haloalkyl, cycloalkyl, cyclic alkyl ether, alkenyl, alkenylene, alkynyl, alkynylene, cycloalkylene, heterocycloalkyl, heterocycloalkylene, aryl, arylene, arylene-oxy, heteroaryl, amino, amido and a combination thereof; and R3 is

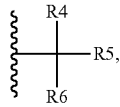

wherein R4, R5, and R6 are the same or different and are selected from the group consisting of:

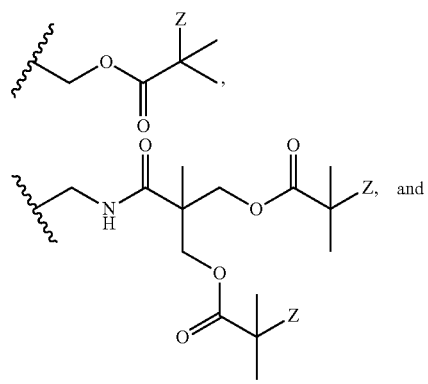

and wherein Z is —NCS, —F, —Cl, —Br, —I, or polymer, the polymer is synthesized with a monomer selected from the group consisting of:

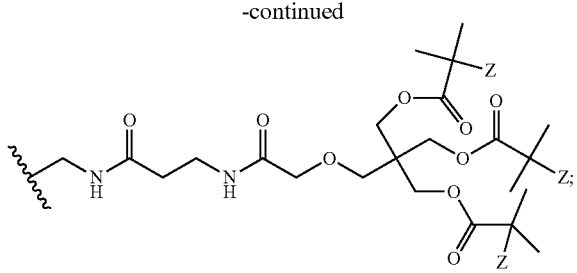

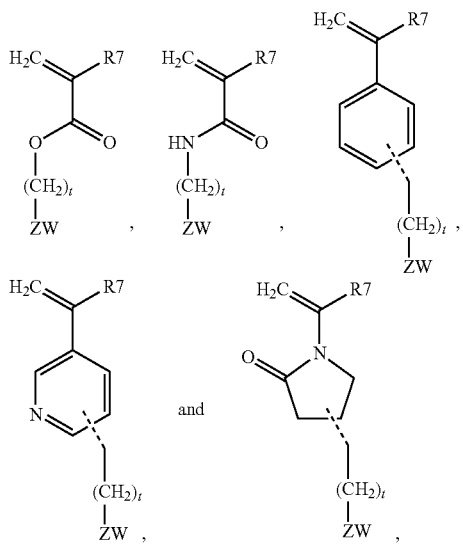

wherein

R7 is H or C$_{1-6}$ alkyl, ZW is a zwitterion, and t is 1 to 6.

2. The compound of claim 1, wherein R2 comprises a structure having the formula:

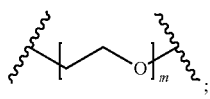

wherein m is an integer from 1 to 20.

3. The compound of claim 2, wherein R2 is:

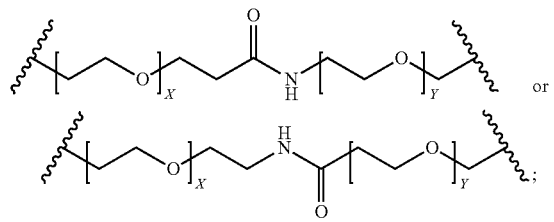

wherein X is an integer from 0 to 50, and Y is an integer from 1 to 50.

4. The compound of claim 1, wherein the zwitterion is phosphorylcholine.

5. The compound of claim 1, wherein Z is the polymer, and the monomer is 2-(methacryloyloxyethyl)-2'-(trimethylammoniumethyl) phosphate (MPC) or 2-(acryloyloxyethyl)-2'-(trimethylammoniumethyl) phosphate.

6. The compound of claim 5, wherein the monomer is 2-(methacryloyloxyethyl)-2'-(trimethylammoniumethyl) phosphate (MPC).

7. The compound according to claim 6, wherein R2 is:

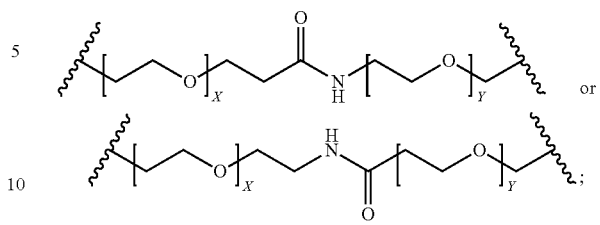

Y is an integer from 1 to 10; and X is 4, 8, or 12.

8. The compound according to claim 7, wherein Y is 4.

9. The compound of claim 1, wherein Z is —Br.

10. The compound according to claim 1, wherein the total molecular weight of the compound is about 500,000 to about 1,000,000 daltons.

11. The compound according to claim 10, wherein the total molecular weight of the compound is about 650,000 to about 850,000 daltons.

12. The compound according to claim 11, wherein the total molecular weight of the compound is about 750,000 daltons.

13. The compound of claim 1, wherein Z is —NCS, —F, —Cl, —Br, or —I.

14. The compound of claim 13 having the following formula:

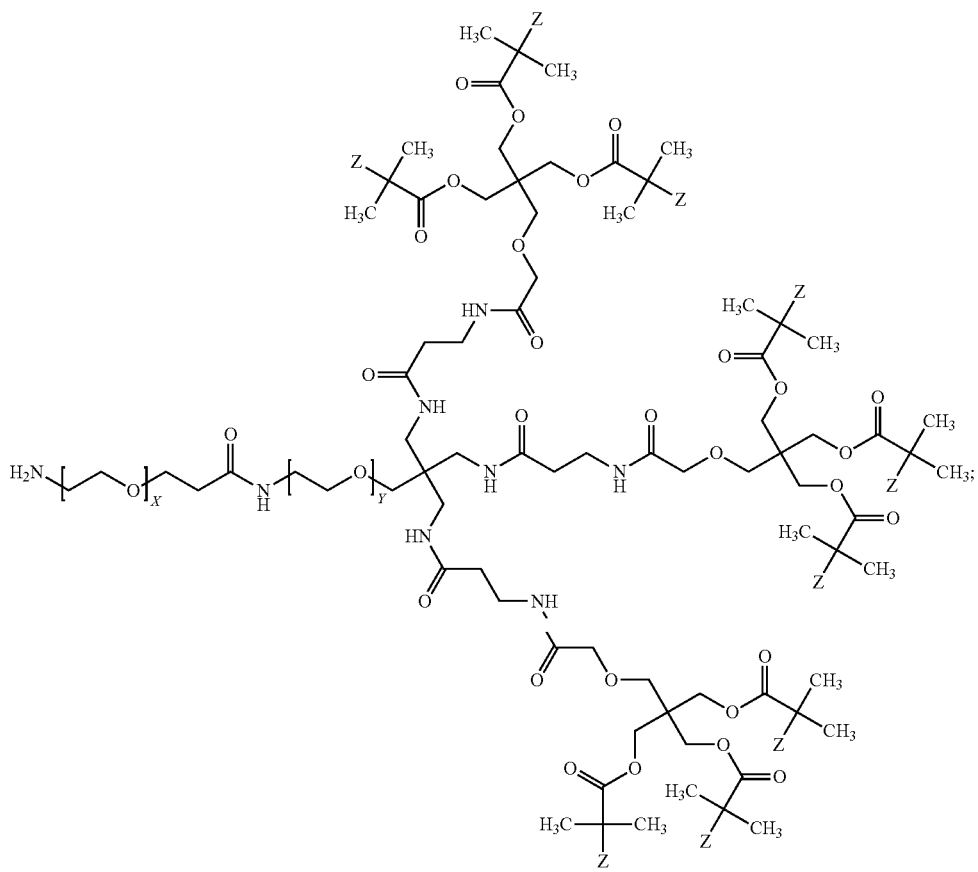

and
wherein Y is an integer from 1 to 50, and X is an integer from 0 to 50.

15. The compound of claim 1 having the following formula:

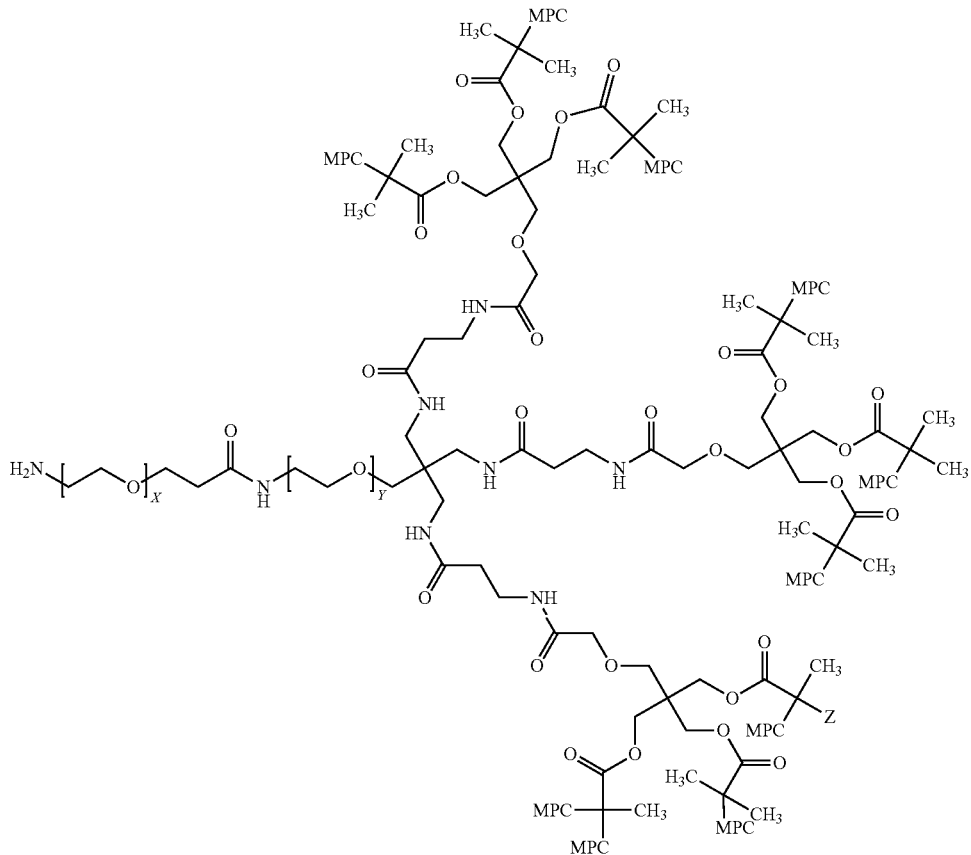

and
wherein Y is an integer from 1 to 50, X is an integer from 0 to 50, and MPC is polyMPC arm.

16. A method of synthesizing a linker-polymerized initiator comprising:

combining the compound of claim 13 with monomers selected from the group consisting of:

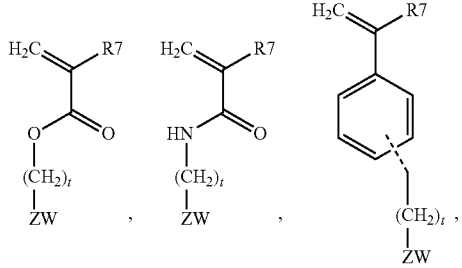

wherein R7 is H or $C_{1-6}$ alkyl, ZW is a zwitterion, and t is 1 to 6, thereby forming a polymerized initiator; and coupling a linker moiety comprising second and third reactive groups to the polymerized initiator to provide a linker-polymerized initiator having an unreacted reactive group.

17. The method of claim 16, wherein the linker moiety is
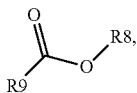
wherein:
R8 is
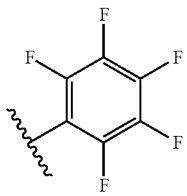 and ;
and
R9 is selected from the group consisting of:
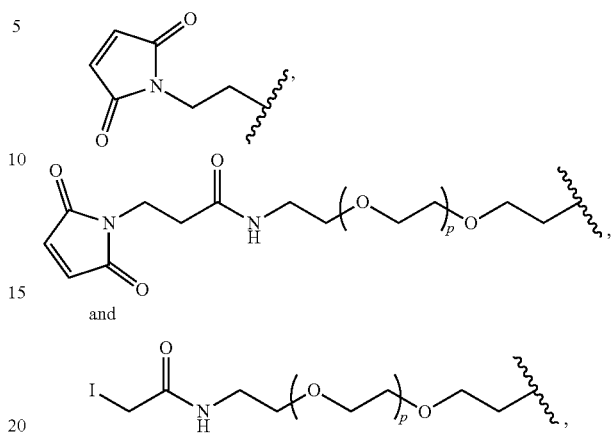
wherein P is an integer from 1 to 12.
18. The method of claim 16, wherein the compound is further represented by the following formula:
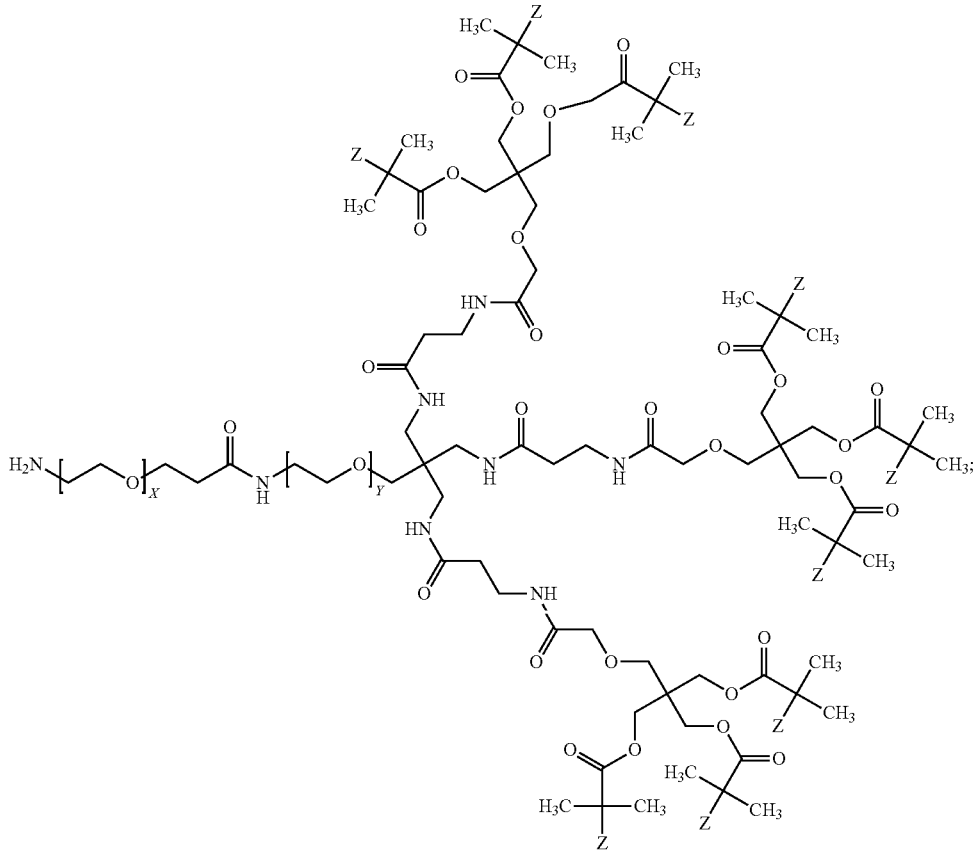

and
wherein Y is an integer from 1 to 50, X is an integer from 0 to 50 and Z is —NCS, —F, —Cl, —Br, or —I.
19. The method of claim 16, wherein the polymerized initiator has the following formula:
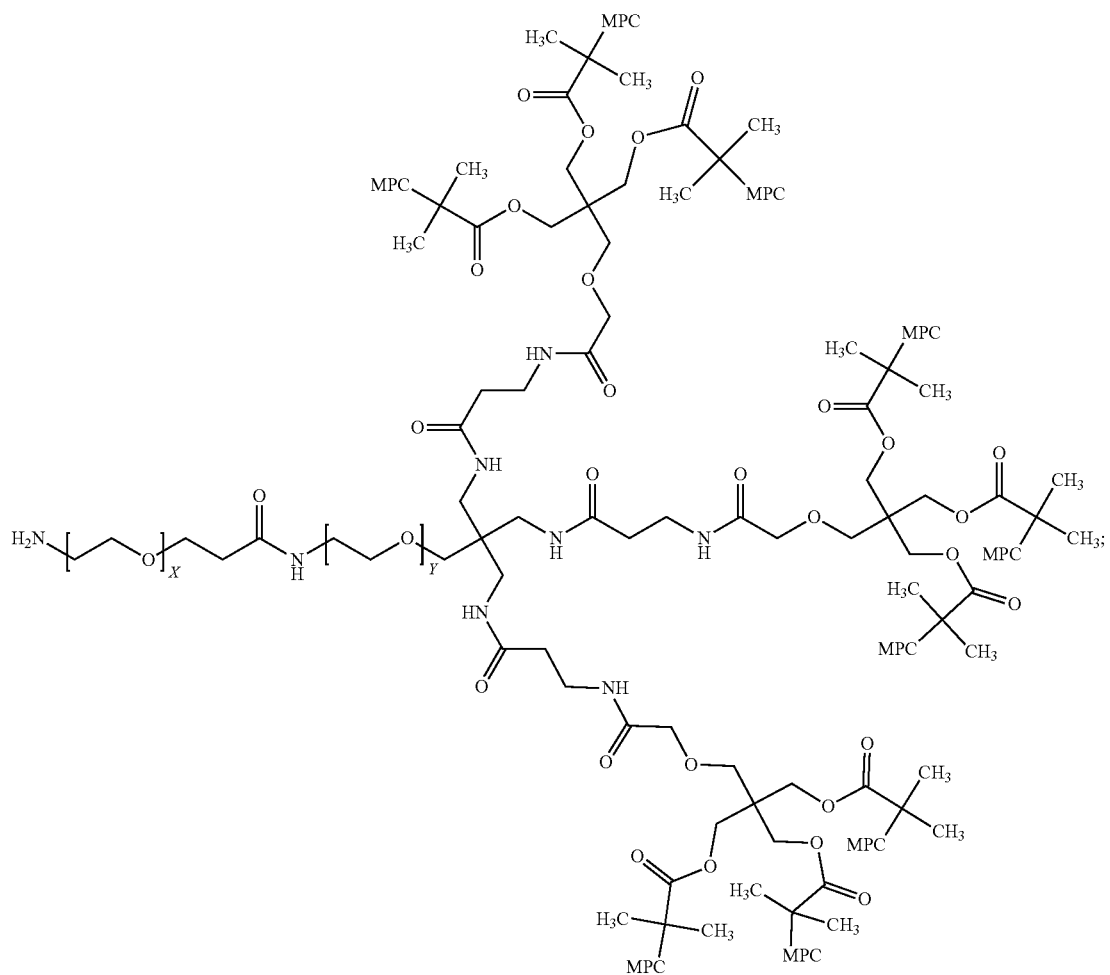
and
wherein Y is an integer from 1 to 50, X is an integer from 0 to 50, and MPC is polyMPC arm.
20. The method of claim 16, wherein the linker-polymerized initiator has the following formula:

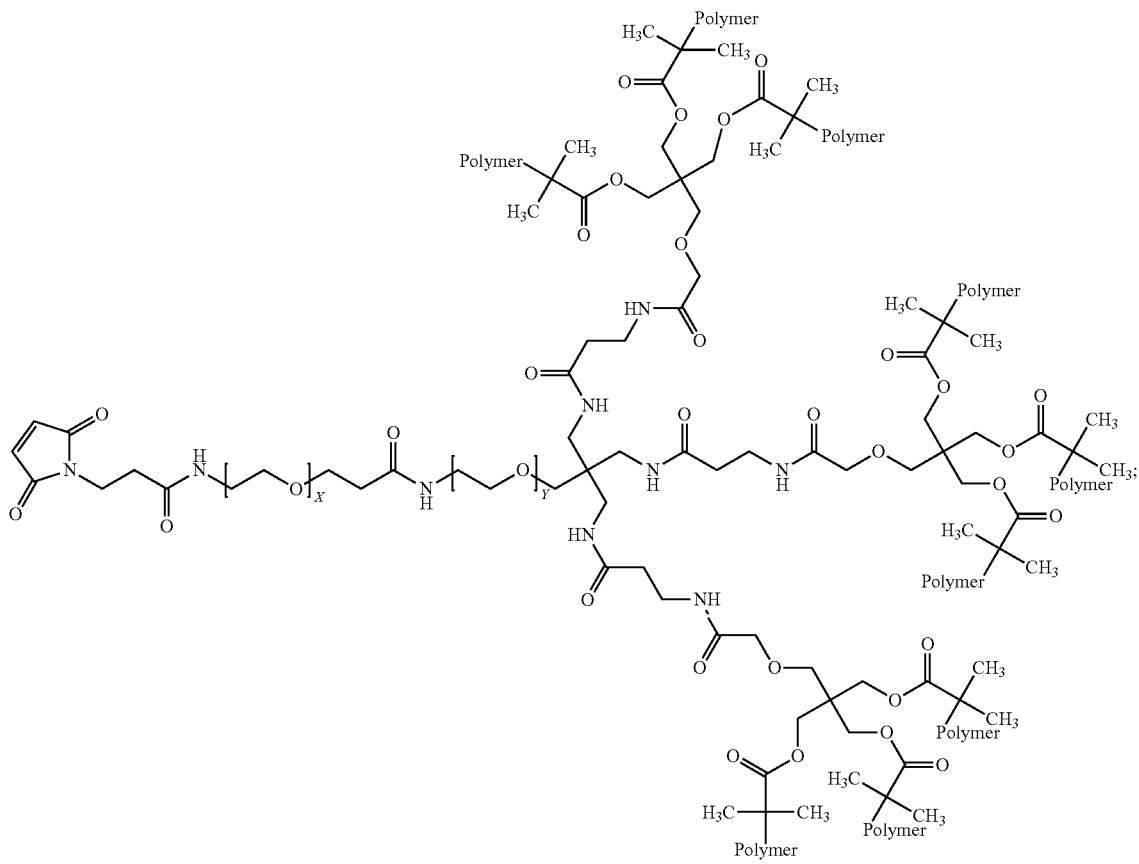
and
wherein Y is an integer from 1 to 50, X is an integer from 0 to 50, and polymer is synthesized with a monomer selected from the group consisting of:
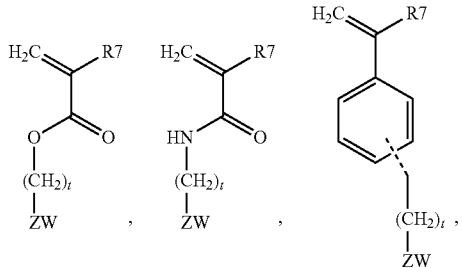
-continued
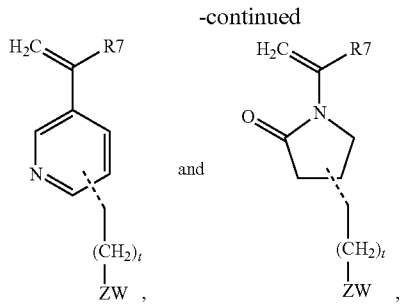
wherein R7 is H or $C_{1-6}$ alkyl, ZW is a zwitterion, and t is 1 to 6.
* * * * *

SEQUENCE LISTING

```
<160> NUMBER OF SEQ ID NOS: 1

<210> SEQ ID NO 1
<211> LENGTH: 2332
<212> TYPE: PRT
<213> ORGANISM: Homo sapiens

<400> SEQUENCE: 1

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95
```

```
Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
```

```
                515                 520                 525
Leu Thr Arg Tyr Tyr Ser Ser Phe Val Asn Met Glu Arg Asp Leu Ala
530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
                580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Thr Arg
                740                 745                 750

Gln Lys Gln Phe Asn Ala Thr Thr Ile Pro Glu Asn Asp Ile Glu Lys
        755                 760                 765

Thr Asp Pro Trp Phe Ala His Arg Thr Pro Met Pro Lys Ile Gln Asn
770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
                820                 825                 830

Glu Met Thr His Phe Arg Pro Gln Leu His His Ser Gly Asp Met Val
        835                 840                 845

Phe Thr Pro Glu Ser Gly Leu Gln Leu Arg Leu Asn Glu Lys Leu Gly
850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895

Gly Thr Asp Asn Thr Ser Ser Leu Gly Pro Pro Ser Met Pro Val His
                900                 905                 910

Tyr Asp Ser Gln Leu Asp Thr Thr Leu Phe Gly Lys Lys Ser Ser Pro
        915                 920                 925

Leu Thr Glu Ser Gly Gly Pro Leu Ser Leu Ser Glu Glu Asn Asn Asp
930                 935                 940
```

```
Ser Lys Leu Leu Glu Ser Gly Leu Met Asn Ser Gln Glu Ser Trp
945                 950                 955                 960

Gly Lys Asn Val Ser Ser Thr Glu Ser Gly Arg Leu Phe Lys Gly Lys
            965                 970                 975

Arg Ala His Gly Pro Ala Leu Leu Thr Lys Asp Asn Ala Leu Phe Lys
            980                 985                 990

Val Ser Ile Ser Leu Leu Lys Thr Asn Lys Thr Ser Asn Asn Ser Ala
            995                 1000                1005

Thr Asn Arg Lys Thr His Ile Asp Gly Pro Ser Leu Leu Ile Glu Asn
            1010                1015                1020

Ser Pro Ser Val Trp Gln Asn Ile Leu Glu Ser Asp Thr Glu Phe Lys
1025                1030                1035                1040

Lys Val Thr Pro Leu Ile His Asp Arg Met Leu Met Asp Lys Asn Ala
                1045                1050                1055

Thr Ala Leu Arg Leu Asn His Met Ser Asn Lys Thr Thr Ser Ser Lys
                1060                1065                1070

Asn Met Glu Met Val Gln Gln Lys Lys Glu Gly Pro Ile Pro Pro Asp
                1075                1080                1085

Ala Gln Asn Pro Asp Met Ser Phe Phe Lys Met Leu Phe Leu Pro Glu
1090                1095                1100

Ser Ala Arg Trp Ile Gln Arg Thr His Gly Lys Asn Ser Leu Asn Ser
1105                1110                1115                1120

Gly Gln Gly Pro Ser Pro Lys Gln Leu Val Ser Leu Gly Pro Glu Lys
                1125                1130                1135

Ser Val Glu Gly Gln Asn Phe Leu Ser Glu Lys Asn Lys Val Val Val
                1140                1145                1150

Gly Lys Gly Glu Phe Thr Lys Asp Val Gly Leu Lys Glu Met Val Phe
                1155                1160                1165

Pro Ser Ser Arg Asn Leu Phe Leu Thr Asn Leu Asp Asn Leu His Glu
                1170                1175                1180

Asn Asn Thr His Asn Gln Glu Lys Lys Ile Gln Glu Glu Ile Glu Lys
1185                1190                1195                1200

Lys Glu Thr Leu Ile Gln Glu Asn Val Val Leu Pro Gln Ile His Thr
                1205                1210                1215

Val Thr Gly Thr Lys Asn Phe Met Lys Asn Leu Phe Leu Leu Ser Thr
                1220                1225                1230

Arg Gln Asn Val Glu Gly Ser Tyr Asp Gly Ala Tyr Ala Pro Val Leu
                1235                1240                1245

Gln Asp Phe Arg Ser Leu Asn Asp Ser Thr Asn Arg Thr Lys Lys His
                1250                1255                1260

Thr Ala His Phe Ser Lys Lys Gly Glu Glu Asn Leu Glu Gly Leu
1265                1270                1275                1280

Gly Asn Gln Thr Lys Gln Ile Val Glu Lys Tyr Ala Cys Thr Thr Arg
                1285                1290                1295

Ile Ser Pro Asn Thr Ser Gln Gln Asn Phe Val Thr Gln Arg Ser Lys
                1300                1305                1310

Arg Ala Leu Lys Gln Phe Arg Leu Pro Leu Glu Glu Thr Glu Leu Glu
                1315                1320                1325

Lys Arg Ile Ile Val Asp Asp Thr Ser Thr Gln Trp Ser Lys Asn Met
                1330                1335                1340

Lys His Leu Thr Pro Ser Thr Leu Thr Gln Ile Asp Tyr Asn Glu Lys
1345                1350                1355                1360
```

```
Glu Lys Gly Ala Ile Thr Gln Ser Pro Leu Ser Asp Cys Leu Thr Arg
                1365                1370                1375

Ser His Ser Ile Pro Gln Ala Asn Arg Ser Pro Leu Pro Ile Ala Lys
                1380                1385                1390

Val Ser Ser Phe Pro Ser Ile Arg Pro Ile Tyr Leu Thr Arg Val Leu
                1395                1400                1405

Phe Gln Asp Asn Ser Ser His Leu Pro Ala Ala Ser Tyr Arg Lys Lys
                1410                1415                1420

Asp Ser Gly Val Gln Glu Ser Ser His Phe Leu Gln Gly Ala Lys Lys
1425                1430                1435                1440

Asn Asn Leu Ser Leu Ala Ile Leu Thr Leu Glu Met Thr Gly Asp Gln
                1445                1450                1455

Arg Glu Val Gly Ser Leu Gly Thr Ser Ala Thr Asn Ser Val Thr Tyr
                1460                1465                1470

Lys Lys Val Glu Asn Thr Val Leu Pro Lys Pro Asp Leu Pro Lys Thr
                1475                1480                1485

Ser Gly Lys Val Glu Leu Leu Pro Lys Val His Ile Tyr Gln Lys Asp
                1490                1495                1500

Leu Phe Pro Thr Glu Thr Ser Asn Gly Ser Pro Gly His Leu Asp Leu
1505                1510                1515                1520

Val Glu Gly Ser Leu Leu Gln Gly Thr Glu Gly Ala Ile Lys Trp Asn
                1525                1530                1535

Glu Ala Asn Arg Pro Gly Lys Val Pro Phe Leu Arg Val Ala Thr Glu
                1540                1545                1550

Ser Ser Ala Lys Thr Pro Ser Lys Leu Leu Asp Pro Leu Ala Trp Asp
                1555                1560                1565

Asn His Tyr Gly Thr Gln Ile Pro Lys Glu Glu Trp Lys Ser Gln Glu
                1570                1575                1580

Lys Ser Pro Glu Lys Thr Ala Phe Lys Lys Lys Asp Thr Ile Leu Ser
1585                1590                1595                1600

Leu Asn Ala Cys Glu Ser Asn His Ala Ile Ala Ala Ile Asn Glu Gly
                1605                1610                1615

Gln Asn Lys Pro Glu Ile Glu Val Thr Trp Ala Lys Gln Gly Arg Thr
                1620                1625                1630

Glu Arg Leu Cys Ser Gln Asn Pro Pro Val Leu Lys Arg His Gln Arg
                1635                1640                1645

Glu Ile Thr Arg Thr Thr Leu Gln Ser Asp Gln Glu Glu Ile Asp Tyr
                1650                1655                1660

Asp Asp Thr Ile Ser Val Glu Met Lys Lys Glu Asp Phe Asp Ile Tyr
1665                1670                1675                1680

Asp Glu Asp Glu Asn Gln Ser Pro Arg Ser Phe Gln Lys Lys Thr Arg
                1685                1690                1695

His Tyr Phe Ile Ala Ala Val Glu Arg Leu Trp Asp Tyr Gly Met Ser
                1700                1705                1710

Ser Ser Pro His Val Leu Arg Asn Arg Ala Gln Ser Gly Ser Val Pro
                1715                1720                1725

Gln Phe Lys Lys Val Val Phe Gln Glu Phe Thr Asp Gly Ser Phe Thr
                1730                1735                1740

Gln Pro Leu Tyr Arg Gly Glu Leu Asn Glu His Leu Gly Leu Leu Gly
1745                1750                1755                1760

Pro Tyr Ile Arg Ala Glu Val Glu Asp Asn Ile Met Val Thr Phe Arg
                1765                1770                1775

Asn Gln Ala Ser Arg Pro Tyr Ser Phe Tyr Ser Ser Leu Ile Ser Tyr
```

```
            1780              1785              1790
Glu Glu Asp Gln Arg Gln Gly Ala Glu Pro Arg Lys Asn Phe Val Lys
        1795              1800              1805

Pro Asn Glu Thr Lys Thr Tyr Phe Trp Lys Val Gln His His Met Ala
    1810              1815              1820

Pro Thr Lys Asp Glu Phe Asp Cys Lys Ala Trp Ala Tyr Phe Ser Asp
1825              1830              1835              1840

Val Asp Leu Glu Lys Asp Val His Ser Gly Leu Ile Gly Pro Leu Leu
            1845              1850              1855

Val Cys His Thr Asn Thr Leu Asn Pro Ala His Gly Arg Gln Val Thr
        1860              1865              1870

Val Gln Glu Phe Ala Leu Phe Phe Thr Ile Phe Asp Glu Thr Lys Ser
    1875              1880              1885

Trp Tyr Phe Thr Glu Asn Met Glu Arg Asn Cys Arg Ala Pro Cys Asn
        1890              1895              1900

Ile Gln Met Glu Asp Pro Thr Phe Lys Glu Asn Tyr Arg Phe His Ala
1905              1910              1915              1920

Ile Asn Gly Tyr Ile Met Asp Thr Leu Pro Gly Leu Val Met Ala Gln
            1925              1930              1935

Asp Gln Arg Ile Arg Trp Tyr Leu Leu Ser Met Gly Ser Asn Glu Asn
        1940              1945              1950

Ile His Ser Ile His Phe Ser Gly His Val Phe Thr Val Arg Lys Lys
        1955              1960              1965

Glu Glu Tyr Lys Met Ala Leu Tyr Asn Leu Tyr Pro Gly Val Phe Glu
    1970              1975              1980

Thr Val Glu Met Leu Pro Ser Lys Ala Gly Ile Trp Arg Val Glu Cys
1985              1990              1995              2000

Leu Ile Gly Glu His Leu His Ala Gly Met Ser Thr Leu Phe Leu Val
            2005              2010              2015

Tyr Ser Asn Lys Cys Gln Thr Pro Leu Gly Met Ala Ser Gly His Ile
        2020              2025              2030

Arg Asp Phe Gln Ile Thr Ala Ser Gly Gln Tyr Gly Gln Trp Ala Pro
        2035              2040              2045

Lys Leu Ala Arg Leu His Tyr Ser Gly Ser Ile Asn Ala Trp Ser Thr
    2050              2055              2060

Lys Glu Pro Phe Ser Trp Ile Lys Val Asp Leu Leu Ala Pro Met Ile
2065              2070              2075              2080

Ile His Gly Ile Lys Thr Gln Gly Ala Arg Gln Lys Phe Ser Ser Leu
            2085              2090              2095

Tyr Ile Ser Gln Phe Ile Ile Met Tyr Ser Leu Asp Gly Lys Lys Trp
        2100              2105              2110

Gln Thr Tyr Arg Gly Asn Ser Thr Gly Thr Leu Met Val Phe Phe Gly
        2115              2120              2125

Asn Val Asp Ser Ser Gly Ile Lys His Asn Ile Phe Asn Pro Pro Ile
    2130              2135              2140

Ile Ala Arg Tyr Ile Arg Leu His Pro Thr His Tyr Ser Ile Arg Ser
2145              2150              2155              2160

Thr Leu Arg Met Glu Leu Met Gly Cys Asp Leu Asn Ser Cys Ser Met
            2165              2170              2175

Pro Leu Gly Met Glu Ser Lys Ala Ile Ser Asp Ala Gln Ile Thr Ala
        2180              2185              2190

Ser Ser Tyr Phe Thr Asn Met Phe Ala Thr Trp Ser Pro Ser Lys Ala
        2195              2200              2205
```

```
Arg Leu His Leu Gln Gly Arg Ser Asn Ala Trp Arg Pro Gln Val Asn
    2210            2215                2220
Asn Pro Lys Glu Trp Leu Gln Val Asp Phe Gln Lys Thr Met Lys Val
2225            2230                2235            2240
Thr Gly Val Thr Thr Gln Gly Val Lys Ser Leu Leu Thr Ser Met Tyr
                2245            2250            2255
Val Lys Glu Phe Leu Ile Ser Ser Ser Gln Asp Gly His Gln Trp Thr
            2260            2265            2270
Leu Phe Phe Gln Asn Gly Lys Val Lys Val Phe Gln Gly Asn Gln Asp
        2275            2280            2285
Ser Phe Thr Pro Val Val Asn Ser Leu Asp Pro Pro Leu Leu Thr Arg
    2290            2295            2300
Tyr Leu Arg Ile His Pro Gln Ser Trp Val His Gln Ile Ala Leu Arg
2305            2310            2315            2320
Met Glu Val Leu Gly Cys Glu Ala Gln Asp Leu Tyr
                2325            2330
```